US009795282B2

(12) United States Patent
Sholev et al.

(10) Patent No.: US 9,795,282 B2
(45) Date of Patent: Oct. 24, 2017

(54) DEVICE AND METHOD FOR MANEUVERING ENDOSCOPE

(71) Applicant: M.S.T. MEDICAL SURGERY TECHNOLOGIES LTD., Yoqneam (IL)

(72) Inventors: Mordehai Sholev, Moshav Amikam (IL); Gal Atarot, Kfar Saba (IL); Shlomi Karvat, Moshav Ramat Zvi (IL)

(73) Assignee: M.S.T. MEDICAL SURGERY TECHNOLOGIES LTD, Yoqneam (IL)

( * ) Notice: Subject to any disclaimer, the term of this patent is extended or adjusted under 35 U.S.C. 154(b) by 215 days.

(21) Appl. No.: 14/154,225

(22) Filed: Jan. 14, 2014

(65) Prior Publication Data

US 2014/0221738 A1 Aug. 7, 2014

Related U.S. Application Data

(63) Continuation-in-part of application No. PCT/IL2012/000342, filed on Sep. 20, 2012.
(Continued)

(51) Int. Cl.
*A61B 1/00* (2006.01)
*A61B 1/01* (2006.01)
(Continued)

(52) U.S. Cl.
CPC ............ *A61B 1/01* (2013.01); *A61B 1/00149* (2013.01); *A61B 90/50* (2016.02);
(Continued)

(58) Field of Classification Search
CPC ......... A61B 1/0057; A61B 1/008; A61B 1/01; A61B 19/26; A61B 2019/265; A61B 2019/263; A61B 2019/2211
(Continued)

(56) References Cited

U.S. PATENT DOCUMENTS 4,559,928 A 12/1985 Takayama
4,756,204 A * 7/1988 Wittwer ............... B25J 19/0016
16/401
(Continued)

FOREIGN PATENT DOCUMENTS

AU 2007234510 A1 12/2007
AU 2013202775 A1 12/2013
(Continued)

OTHER PUBLICATIONS

Atarot et al., Manual Control System for Maneuvering an Endoscope, co-pending U.S. Appl. No. 14/380,082, filed Aug. 21, 2014, 118 pages.
(Continued)

*Primary Examiner* — Timothy J Neal

(57) ABSTRACT

Systems and methods for maneuvering an endoscope are disclosed. The system includes: at least one first pivoting support that is pivotally attached to the endoscope and that permits the endoscope to pivot around at least one first axis of rotation; at least one second pivoting support that is in communication with the at least one first pivoting support and that is adapted to rotate around at least one axis that is substantially orthogonal to said first axis so as to permit the endoscope to rotate around an insertion point into a body in at least two orthogonal axes; and at least one controller attached to either the first or the second pivoting. The controller is adapted to provide a constant dynamic equilibrium between said endoscope and at least one of the pivoting supports.

18 Claims, 46 Drawing Sheets

Related U.S. Application Data

(60) Provisional application No. 61/536,612, filed on Sep. 20, 2012, provisional application No. 61/752,474, filed on Jan. 15, 2013.

(51) Int. Cl.
  *A61B 1/04* (2006.01)
  *A61B 90/50* (2016.01)
  *A61B 34/30* (2016.01)

(52) U.S. Cl.
  CPC ... *A61B 2034/301* (2016.02); *A61B 2090/506* (2016.02); *A61B 2090/5025* (2016.02)

(58) Field of Classification Search
  USPC .................. 600/102, 104, 114, 146, 149
  See application file for complete search history.

(56) References Cited

U.S. PATENT DOCUMENTS

| | | | |
|---|---|---|---|
| 4,854,301 A | 8/1989 | Nakajima | |
| 4,955,891 A | 9/1990 | Carol | |
| 5,086,401 A * | 2/1992 | Glassman | A61B 19/2203 606/53 |
| 5,154,723 A | 10/1992 | Kubota et al. | |
| 5,201,742 A | 4/1993 | Hasson | |
| 5,211,165 A | 5/1993 | Dumoulin et al. | |
| 5,269,305 A | 12/1993 | Corol | |
| 5,313,306 A | 5/1994 | Kuban et al. | |
| 5,494,034 A | 2/1996 | Schlondorff et al. | |
| 5,553,198 A | 9/1996 | Wang et al. | |
| 5,571,072 A | 11/1996 | Kronner | |
| 5,572,999 A | 11/1996 | Funda et al. | |
| 5,749,362 A | 5/1998 | Funda et al. | |
| 5,820,623 A * | 10/1998 | Ng | A61B 19/22 318/568.11 |
| 5,836,869 A | 11/1998 | Kudo et al. | |
| 5,876,325 A | 3/1999 | Mizuno et al. | |
| 5,878,193 A | 3/1999 | Wang et al. | |
| 5,911,036 A | 6/1999 | Wright et al. | |
| 5,971,976 A | 10/1999 | Wang et al. | |
| 6,024,695 A | 2/2000 | Taylor et al. | |
| 6,100,501 A | 8/2000 | von der Heyde | |
| 6,106,511 A | 8/2000 | Jensen | |
| 6,179,776 B1 | 1/2001 | Adams et al. | |
| 6,192,267 B1 | 2/2001 | Scherninski et al. | |
| 6,368,332 B1 | 4/2002 | Salcudean et al. | |
| 6,387,044 B1 | 5/2002 | Tachibana et al. | |
| 6,451,027 B1 | 9/2002 | Cooper et al. | |
| 6,591,239 B1 | 7/2003 | McCall et al. | |
| 6,632,170 B1 | 10/2003 | Bohanan et al. | |
| 6,714,841 B1 | 3/2004 | Wright et al. | |
| 6,723,106 B1 | 4/2004 | Charles et al. | |
| 6,747,566 B2 | 6/2004 | Hou | |
| 6,785,358 B2 | 8/2004 | Johnson et al. | |
| 6,786,896 B1 | 9/2004 | Madhani et al. | |
| 6,837,883 B2 | 1/2005 | Moll et al. | |
| 6,850,794 B2 | 2/2005 | Shahidi | |
| 6,946,812 B1 | 9/2005 | Martin et al. | |
| 6,997,866 B2 | 2/2006 | Payandeh et al. | |
| 7,048,745 B2 | 5/2006 | Tierney et al. | |
| 7,087,049 B2 | 8/2006 | Nowlin et al. | |
| 7,286,992 B2 | 10/2007 | Sander et al. | |
| 7,313,430 B2 | 12/2007 | Urquhart et al. | |
| 7,319,897 B2 | 1/2008 | Leitner et al. | |
| 7,674,270 B2 | 3/2010 | Layer | |
| 7,833,152 B2 | 11/2010 | Chatenever et al. | |
| 8,058,969 B1 | 11/2011 | Lai et al. | |
| 8,079,950 B2 | 12/2011 | Stern et al. | |
| 8,100,133 B2 | 1/2012 | Mintz et al. | |
| 8,123,675 B2 | 2/2012 | Funda et al. | |
| 8,170,717 B2 | 5/2012 | Sutherland et al. | |
| 8,224,484 B2 | 7/2012 | Swarup et al. | |
| 8,256,319 B2 | 9/2012 | Cooper et al. | |
| 8,388,516 B2 | 3/2013 | Sholev | |
| 8,414,475 B2 | 4/2013 | Sholev | |
| 8,435,171 B2 | 5/2013 | Sholev | |
| 8,690,755 B2 | 4/2014 | Sholev | |
| 8,702,590 B2 | 4/2014 | Sholev | |
| 8,758,263 B1 | 6/2014 | Rahimian et al. | |
| 8,992,542 B2 | 3/2015 | Hagag et al. | |
| 9,002,518 B2 | 4/2015 | Manzo et al. | |
| 9,204,939 B2 | 12/2015 | Frimer et al. | |
| 9,295,379 B2 | 3/2016 | Sholev | |
| 9,504,456 B2 | 11/2016 | Frimer et al. | |
| 2002/0026096 A1 | 2/2002 | Motoki et al. | |
| 2002/0082612 A1 | 6/2002 | Moll et al. | |
| 2002/0091301 A1 | 7/2002 | Levin | |
| 2002/0097332 A1 | 7/2002 | Lee et al. | |
| 2002/0111713 A1 | 8/2002 | Wang et al. | |
| 2002/0133174 A1 | 9/2002 | Charles et al. | |
| 2002/0151795 A1 | 10/2002 | Palti | |
| 2002/0166403 A1 | 11/2002 | Choset et al. | |
| 2002/0167422 A1 | 11/2002 | Andre et al. | |
| 2003/0055410 A1 | 3/2003 | Evans et al. | |
| 2003/0062858 A1 | 4/2003 | Shimizu et al. | |
| 2003/0195389 A1 | 10/2003 | Motoki et al. | |
| 2003/0216833 A1 | 11/2003 | Mukai et al. | |
| 2003/0233102 A1 * | 12/2003 | Nakamura | A61B 17/3476 606/130 |
| 2004/0015053 A1 | 1/2004 | Bieger et al. | |
| 2004/0024387 A1 | 2/2004 | Payandeh et al. | |
| 2004/0089777 A1 | 5/2004 | Schilt et al. | |
| 2004/0111183 A1 | 6/2004 | Sutherland et al. | |
| 2004/0138524 A1 | 7/2004 | Ueda et al. | |
| 2004/0162564 A1 | 8/2004 | Charles et al. | |
| 2004/0204627 A1 | 10/2004 | Furukawa | |
| 2004/0239631 A1 | 12/2004 | Gresham | |
| 2005/0043718 A1 | 2/2005 | Madhani et al. | |
| 2005/0090711 A1 | 4/2005 | Fuchs et al. | |
| 2005/0119527 A1 | 6/2005 | Banik et al. | |
| 2005/0123189 A1 | 6/2005 | Bayer et al. | |
| 2005/0162383 A1 | 7/2005 | Rosenberg | |
| 2005/0171557 A1 | 8/2005 | Shoham | |
| 2005/0219552 A1 | 10/2005 | Ackerman et al. | |
| 2005/0272971 A1 | 12/2005 | Ohnishi et al. | |
| 2005/0273086 A1 | 12/2005 | Green et al. | |
| 2006/0100501 A1 | 5/2006 | Berkelman et al. | |
| 2006/0142657 A1 | 6/2006 | Quaid et al. | |
| 2006/0167440 A1 | 7/2006 | Cooper et al. | |
| 2006/0217206 A1 | 9/2006 | Thompson | |
| 2006/0281971 A1 | 12/2006 | Sauer et al. | |
| 2007/0005045 A1 | 1/2007 | Mintz et al. | |
| 2007/0013336 A1 | 1/2007 | Nowlin et al. | |
| 2007/0021713 A1 | 1/2007 | Kumar et al. | |
| 2007/0021752 A1 | 1/2007 | Rogers | |
| 2007/0088340 A1 | 4/2007 | Brock et al. | |
| 2007/0142701 A1 | 6/2007 | Goldberg et al. | |
| 2007/0142824 A1 | 6/2007 | Devengenzo et al. | |
| 2007/0142968 A1 | 6/2007 | Prisco et al. | |
| 2007/0156017 A1 | 7/2007 | Lamprecht et al. | |
| 2007/0265527 A1 | 11/2007 | Wohlgemuth | |
| 2007/0299427 A1 | 12/2007 | Yeung et al. | |
| 2008/0004603 A1 | 1/2008 | Larkin et al. | |
| 2008/0039256 A1 | 2/2008 | Jinno et al. | |
| 2008/0046122 A1 | 2/2008 | Manzo et al. | |
| 2008/0071140 A1 | 3/2008 | Gattani et al. | |
| 2008/0091066 A1 | 4/2008 | Sholev | |
| 2008/0091302 A1 | 4/2008 | Sholev | |
| 2008/0108872 A1 | 5/2008 | Glukhovsky et al. | |
| 2008/0114376 A1 | 5/2008 | Steinberg | |
| 2008/0154389 A1 | 6/2008 | Smith et al. | |
| 2008/0207997 A1 | 8/2008 | Higgins et al. | |
| 2008/0215181 A1 | 9/2008 | Smith et al. | |
| 2008/0234866 A1 | 9/2008 | Kishi et al. | |
| 2008/0262297 A1 | 10/2008 | Gilboa et al. | |
| 2008/0275452 A1 | 11/2008 | Lang et al. | |
| 2008/0300453 A1 | 12/2008 | Aoki et al. | |
| 2008/0312540 A1 | 12/2008 | Ntziachristos | |
| 2009/0018419 A1 | 1/2009 | Torch | |
| 2009/0043310 A1 | 2/2009 | Rasmussen | |
| 2009/0048611 A1 | 2/2009 | Funda et al. | |
| 2009/0062813 A1 | 3/2009 | Prisco et al. | |
| 2009/0088634 A1 | 4/2009 | Zhao et al. | |

(56) References Cited

U.S. PATENT DOCUMENTS

| | | |
|---|---|---|
| 2009/0088773 A1 | 4/2009 | Zhao et al. |
| 2009/0088774 A1 | 4/2009 | Swarup et al. |
| 2009/0088897 A1 | 4/2009 | Zhao et al. |
| 2009/0099520 A1 | 4/2009 | Millman et al. |
| 2009/0171373 A1 | 7/2009 | Farritor et al. |
| 2009/0177032 A1 | 7/2009 | Garibaldi et al. |
| 2009/0216114 A1 | 8/2009 | Gorges et al. |
| 2009/0240259 A1 | 9/2009 | Nelson et al. |
| 2009/0248037 A1 | 10/2009 | Prisco |
| 2009/0312101 A1 | 12/2009 | Pope |
| 2009/0312600 A1 | 12/2009 | Sholev |
| 2010/0022871 A1 | 1/2010 | De Beni et al. |
| 2010/0036198 A1 | 2/2010 | Tacchino et al. |
| 2010/0063630 A1 | 3/2010 | Sutherland et al. |
| 2010/0121149 A1 | 5/2010 | Sholev |
| 2010/0185211 A1 | 7/2010 | Herman et al. |
| 2010/0185212 A1 | 7/2010 | Sholev |
| 2010/0234857 A1 | 9/2010 | Itkowitz et al. |
| 2010/0274079 A1 | 10/2010 | Kim et al. |
| 2011/0069160 A1 | 3/2011 | Ning |
| 2011/0082587 A1 | 4/2011 | Ziaei et al. |
| 2011/0118748 A1 | 5/2011 | Itkowitz |
| 2011/0144659 A1 | 6/2011 | Sholev |
| 2011/0175989 A1 | 7/2011 | Islam |
| 2011/0177469 A1 | 7/2011 | Suter et al. |
| 2011/0257475 A1 | 10/2011 | Berkelman et al. |
| 2012/0020547 A1 | 1/2012 | Zhao et al. |
| 2012/0029277 A1 | 2/2012 | Sholev |
| 2012/0041263 A1 | 2/2012 | Sholev |
| 2012/0071893 A1 | 3/2012 | Smith et al. |
| 2012/0245415 A1 | 9/2012 | Emura et al. |
| 2013/0063580 A1 | 3/2013 | Ogawa et al. |
| 2013/0123804 A1 | 5/2013 | Sholev et al. |
| 2013/0204271 A1 | 8/2013 | Brisson et al. |
| 2014/0005489 A1 | 1/2014 | Charles |
| 2014/0052005 A1 | 2/2014 | Yokota |
| 2014/0066703 A1 | 3/2014 | Blumenkranz et al. |
| 2014/0142592 A1 | 5/2014 | Moon et al. |
| 2014/0163359 A1 | 6/2014 | Sholev et al. |
| 2014/0194896 A1 | 7/2014 | Frimer et al. |
| 2014/0221738 A1 | 8/2014 | Sholev et al. |
| 2014/0228632 A1 | 8/2014 | Sholev et al. |
| 2014/0378763 A1 | 12/2014 | Atarot et al. |
| 2015/0025549 A1 | 1/2015 | Kilroy et al. |
| 2015/0031953 A1 | 1/2015 | Atarot et al. |
| 2015/0238276 A1 | 8/2015 | Atarot et al. |
| 2015/0366433 A1 | 12/2015 | Atarot et al. |
| 2016/0007826 A1 | 1/2016 | Frimer et al. |
| 2016/0007827 A1 | 1/2016 | Frimer et al. |
| 2016/0007828 A1 | 1/2016 | Frimer et al. |
| 2016/0015473 A1 | 1/2016 | Frimer et al. |
| 2016/0051336 A1 | 2/2016 | Frimer et al. |
| 2016/0174817 A1 | 6/2016 | Frimer et al. |
| 2016/0174955 A1 | 6/2016 | Frimer et al. |
| 2016/0184031 A1 | 6/2016 | Sholev et al. |
| 2016/0242631 A1 | 8/2016 | Sholev |
| 2016/0270864 A1 | 9/2016 | Frimer et al. |
| 2016/0345802 A1 | 12/2016 | Tal Nir et al. |
| 2017/0027654 A1 | 2/2017 | Frimer et al. |
| 2017/0049521 A1 | 2/2017 | Sholev et al. |

FOREIGN PATENT DOCUMENTS

| | | |
|---|---|---|
| CN | 203042209 U | 7/2013 |
| EP | 1681029 A1 | 7/2006 |
| EP | 2246006 A2 | 4/2010 |
| EP | 2208463 A1 | 7/2010 |
| EP | 2246006 A2 | 11/2010 |
| EP | 2347785 A1 | 7/2011 |
| IL | 184664 A | 2/2015 |
| JP | 6063003 A | 3/1994 |
| KR | 20090123260 A | 12/2009 |
| WO | 1996009587 A1 | 3/1996 |
| WO | 2003007834 A1 | 1/2003 |
| WO | 2003094759 A1 | 11/2003 |
| WO | 2006039646 A2 | 4/2006 |
| WO | 2006111966 A2 | 10/2006 |
| WO | 2008035345 A2 | 3/2008 |
| WO | 2009004616 A2 | 1/2009 |
| WO | 2009010980 A1 | 1/2009 |
| WO | 2010122563 A1 | 10/2010 |
| WO | 2011088400 A2 | 7/2011 |
| WO | 2013027200 A2 | 2/2013 |
| WO | 2013027201 A2 | 2/2013 |
| WO | 2013027202 A2 | 2/2013 |
| WO | 2013027203 A1 | 2/2013 |
| WO | 2013042107 A1 | 3/2013 |
| WO | 2013128457 A1 | 9/2013 |
| WO | 2013132501 A1 | 9/2013 |
| WO | 2014049598 A1 | 4/2014 |
| WO | 2014108898 A1 | 7/2014 |
| WO | 2015151094 A1 | 10/2015 |
| WO | 2015151098 A3 | 12/2015 |
| WO | 2015189839 A1 | 12/2015 |
| WO | 2016005988 A1 | 1/2016 |

OTHER PUBLICATIONS

Atarot et al., Overall Endoscopic Control System, co-pending U.S. Appl. No. 14/380,086, filed Sep. 16, 2014, 79 pages.

Extended European Search Report issued by the European Patent Office dated Jan. 4, 2014 in corresponding European Application No. EP 14151130.3.

Arshak et al. "A Model for Estimating the Real-Time Positions of a moving Object in Wireless Telemetry Applications using RF Sensors.", Sensors Applications Symposium (SAS), 2007, IEEE Sensors Applications Symposium, San Diego, California, USA, Feb. 6-8, 2008, pp. 1-6.

Advisory Action issued by the USPTO for the U.S. Appl. No. 12/441,838, on Feb. 1, 2013.

Ex Parte Quayle Action issued by the USPTO for the U.S. Appl. No. 13/265,206, on Mar. 14, 2017.

Final Rejection Office Action issued by the USPTO for the U.S. Appl. No. 14/239,897, dated Jan. 26, 2017.

Final Rejection Office Action issued by the USPTO for the U.S. Appl. No. 15/086,194, dated Feb. 27, 2017.

Final Rejection Office Action issued by the USPTO for the U.S. Appl. No. 13/265,206, dated Mar. 16, 2016.

Final Rejection Office Action issued by the USPTO for the U.S. Appl. No. 13/736,118, dated May 9, 2016.

Final Rejection Office Action issued by the USPTO for the U.S. Appl. No. 12/667,420, dated Aug. 1, 2013.

International Preliminary Report on Patentability (Chapter I) for PCT/IL2012/000311, dated Jul. 14, 2015.

Final Rejection Office Action issued by the USPTO for the U.S. Appl. No. 12/441,838, dated Nov. 21, 2012.

Miscellaneous Office Action issued by the USPTO for the U.S. Appl. No. 13/265,206, dated Jun. 22, 2015.

International Preliminary Report on Patentability (Chapter I) for PCT/IL2007/001161, dated Apr. 7, 2009.

Non-Final Rejection Office Action issued by the USPTO for the U.S. Appl. No. 12/667,420, dated Jan. 23, 2013.

Non-Final Rejection Office Action issued by the USPTO for the U.S. Appl. No. 14/816,099, dated Jan. 26, 2017.

Non-Final Rejection Office Action issued by the USPTO for the U.S. Appl. No. 14/816,127, dated Jan. 26, 2017.

Non-Final Rejection Office Action issued by the USPTO for the U.S. Appl. No. 14/817,245, dated Feb. 8, 2017.

Non-Final Rejection Office Action issued by the USPTO for the U.S. Appl. No. 12/441,838, dated Feb. 13, 2012.

Non-Final Rejection Office Action issued by the USPTO for the U.S. Appl. No. 15/169,990, dated Feb. 24, 2017.

Non-Final Rejection Office Action issued by the USPTO for the U.S. Appl. No. 14/752,947, dated Mar. 18, 2016.

Non-Final Rejection Office Action issued by the USPTO for the U.S. Appl. No. 14/150,939, dated Apr. 17, 2015.

Non-Final Rejection Office Action issued by the USPTO for the U.S. Appl. No. 14/239,897, dated Apr. 26, 2016.

(56) References Cited

OTHER PUBLICATIONS

Non-Final Rejection Office Action issued by the USPTO for the U.S. Appl. No. 14/752,949, dated Jun. 7, 2015.
Non-Final Rejection Office Action issued by the USPTO for the U.S. Appl. No. 12/652,131, dated Jun. 15, 2012.
Non-Final Rejection Office Action issued by the USPTO for the U.S. Appl. No. 14/753,902, dated Jun. 16, 2016.
Non-Final Rejection Office Action issued by the USPTO for the U.S. Appl. No. 13/265,206, dated Aug. 13, 2014.
Non-Final Rejection Office Action issued by the USPTO for the U.S. Appl. No. 13/736,118, dated Aug. 13, 2015.
Non-Final Rejection Office Action issued by the USPTO for the U.S. Appl. No. 15/086,194, dated Aug. 19, 2016.
Non-Final Rejection Office Action issued by the USPTO for the U.S. Appl. No. 14/817,223, dated Oct. 7, 2016.
Final Rejection Office Action issued by the USPTO for the U.S. Appl. No. 12/441,838, dated Nov. 12, 2013.
Non-Final Rejection Office Action issued by the USPTO for the U.S. Appl. No. 14/239,997, dated Nov. 16, 2016.
Non-Final Rejection Office Action issued by the USPTO for the U.S. Appl. No. 13/736,118, dated Nov. 18, 2014.
Non-Final Rejection Office Action issued by the USPTO for the U.S. Appl. No. 14/813,170, dated Dec. 9, 2016.
Non-Final Rejection Office Action issued by the USPTO for the U.S. Appl. No. 12/441,838, dated Aug. 16, 2013.
Restriction Requirement Office Action issued by the USPTO for the U.S. Appl. No. 13/736,118, dated Apr. 17, 2014.
Restriction Requirement Office Action issued by the USPTO for the U.S. Appl. No. 14/239,997, dated May 16, 2016.
International Preliminary Report on Patentability (Chapter I) for PCT/IL2013/050806, dated Mar. 31, 2015.
Restriction Requirement Office Action issued by the USPTO for the U.S. Appl. No. 14/380,082, dated Sep. 26, 2016.
Restriction Requirement Office Action issued by the USPTO for the U.S. Appl. No. 12/667,420, dated Nov. 27, 2012.
Restriction Requirement Office Action issued by the USPTO for the U.S. Appl. No. 13/265,206, dated Dec. 2, 2013.
International Preliminary Report on Patentability (Chapter I) for PCT/IL2012/000342, dated Mar. 25, 2014.
Extended European Search Report issued by the EPO for the European Application No. 10766746.1, dated Jan. 17, 2014.
Extended European Search Report issued by the EPO for the European Application No. 140150541.2, dated Aug. 22, 2014.
International Preliminary Report on Patentability (Chapter I) for PCT/IL2008/000902, dated Jan. 5, 2010.
International Preliminary Report on Patentability (Chapter I) for PCT/IL2015/050718, dated Jan. 10, 2017.
International Preliminary Report on Patentability (Chapter I) for PCT/IL2012/000310, dated Feb. 25, 2014.
International Preliminary Report on Patentability (Chapter I) for PCT/IL2012/000312, dated Feb. 25, 2014.
International Preliminary Report on Patentability (Chapter I) for PCT/IL2014/050022, dated Jul. 14, 2015.
International Preliminary Report on Patentability (Chapter I) for PCT/IL2013/050183, dated Sep. 2, 2014.
International Preliminary Report on Patentability (Chapter I) for PCT/IL2013/050216, dated Sep. 9, 2014.
International Preliminary Report on Patentability (Chapter I) for PCT/IL2015/050345, dated Oct. 4, 2016.
International Preliminary Report on Patentability (Chapter I) for PCT/IL2015/050349, dated Oct. 4, 2016.
International Preliminary Report on Patentability (Chapter I) for PCT/IL2006/000478, dated Oct. 23, 2007.
International Preliminary Report on Patentability (Chapter I) for PCT/IL2010/000330, dated Oct. 25, 2011.
International Preliminary Report on Patentability (Chapter II) for PCT/IL2015/050579, dated Jun. 2, 2016.
International Preliminary Report on Patentability (Chapter II) for PCT/IL2008/000994, dated Jun. 10, 2009.
International Search Report for PCT/IL2012/000312, dated Jan. 8, 2013.
International Search Report for PCT/IL2013/050806, dated Feb. 10, 2014.
International Search Report for PCT/IL2012/000311, dated Feb. 13, 2013.
International Search Report for PCT/IL2012/000342, dated Feb. 25, 2013.
International Search Report for PCT/IL2012/000310, dated Feb. 28, 2013.
International Search Report for PCT/IL2008/000902, dated Mar. 2, 2009.
International Search Report for PCT/IL2014/050022, dated May 12, 2014.
International Search Report for PCT/IL2013/050183, dated Jun. 28, 2013.
International Search Report for PCT/IL2010/000330, dated Aug. 10, 2010.
International Search Report for PCT/IL2013/050216, dated Aug. 20, 2013.
International Search Report for PCT/IL2015/050345, dated Sep. 2, 2015.
International Search Report for PCT/IL2006/000478, dated Sep. 5, 2007.
International Search Report for PCT/IL2007/001161, dated Sep. 12, 2008.
International Search Report for PCT/IL2015/050579, dated Nov. 2, 2015.
International Search Report for PCT/IL2015/050349, dated Nov. 4, 2015.
International Search Report for PCT/IL2012/000309 dated Feb. 7, 2013.
International Search Report for PCT/IL2015/050718, dated Nov. 10, 2015.
International Search Report for PCT/IL2008/000994, dated Dec. 1, 2008.
Response dated Jan. 9, 2015, to Non-Final Rejection Office Action issued by the USPTO for the U.S. Appl. No. 13/265,206, dated Aug. 13, 2014.
Response dated Jan. 10, 2013, to Final Rejection Office Action issued by the USPTO for the U.S. Appl. No. 12/441,838, dated Nov. 21, 2012.
Response dated Feb. 3, 2014, to Restriction Requirement Office Action issued by the USPTO for the U.S. Appl. No. 13/265,206, dated Dec. 2, 2013.
Response dated Dec. 16, 2012, to Non-Final Rejection Office Action issued by the USPTO for the U.S. Appl. No. 12/652,131, dated Jun. 15, 2012.
Response dated Feb. 8, 2017, to Non-Final Rejection Office Action issued by the USPTO for the U.S. Appl. No. 15/086,194, dated Aug. 19, 2016.
Response dated Feb. 21, 2013, to Advisory Action issued by the USPTO for the U.S. Appl. No. 12/441,838, dated Feb. 21, 2013.
Response dated Mar. 31, 2016, to Final Rejection Office Action issued by the USPTO for the U.S. Appl. No. 13/265,206, dated Mar. 16, 2016.
Response dated Apr. 3, 2013, to Non-Final Rejection Office Action issued by the USPTO for the U.S. Appl. No. 12/667,420, dated Jan. 23, 2013.
Response dated Apr. 21, 2015, to Non-Final Rejection Office Action issued by the USPTO for the U.S. Appl. No. 13/736,118, dated Nov. 18, 2014.
Response dated May 14, 2012, to Non-Final Rejection Office Action issued by the USPTO for the U.S. Appl. No. 12/441,838, dated Feb. 13, 2012.
Response dated Jun. 1, 2016, to Non-Final Rejection Office Action issued by the USPTO for the U.S. Appl. No. 14/752,947, dated Mar. 18, 2016.
Response dated Jun. 21, 2015, to Non-Final Rejection Office Action issued by the USPTO for the U.S. Appl. No. 14/150,939, dated Apr. 17, 2015.

(56) References Cited

OTHER PUBLICATIONS

Response dated Jul. 14, 2014, to Restriction Requirement Office Action issued by the USPTO for the U.S. Appl. No. 13/736,118, dated Apr. 17, 2014.
Response dated Aug. 6, 2015, to Miscellaneous Office Action issued by the USPTO for the U.S. Appl. No. 13/265,206, dated Jun. 22, 2015.
Response dated Aug. 6, 2015, to Restriction Requirement Office Action issued by the USPTO for the U.S. Appl. No. 14/239,997, dated May 16, 2016.
Response dated Sep. 10, 2013, to Final Rejection Office Action issued by the USPTO for the U.S. Appl. No. 12/667,420, dated Aug. 1, 2013.
Response dated Oct. 10, 2013, to Non-Final Rejection Office Action issued by the USPTO for the U.S. Appl. No. 12/441,838, dated Aug. 16, 2013.
Response dated Oct. 10, 2016, to Non-Final Rejection Office Action issued by the USPTO for the U.S. Appl. No. 14/239,897, dated Apr. 26, 2016.
Response dated Nov. 8, 2016, to Final Rejection Office Action issued by the USPTO for the U.S. Appl. No. 13/736,118, dated May 9, 2016.
Response dated Nov. 24, 2016, to Non-Final Rejection Office Action issued by the USPTO for the U.S. Appl. No. 14/753,902, dated Jun. 7, 2015.
Response dated Nov. 24, 2016, to Non-Final Rejection Office Action issued by the USPTO for the U.S. Appl. No. 14/752,949, dated Jun. 7, 2015.
Response dated Dec. 28, 2012, to Restriction Requirement Office Action issued by the USPTO for the U.S. Appl. No. 12/667,420, dated Nov. 27, 2012.
Response dated Dec. 31, 2015, to Non-Final Rejection Office Action issued by the USPTO for the U.S. Appl. No. 13/736,118, dated Aug. 13, 2015.
Response dated Nov. 19, 2013, to Non-Final Rejection Office Action issued by the USPTO for the U.S. Appl. No. 12/441,838, dated Nov. 12, 2013.
Non-Final Rejection Office Action issued for U.S. Appl. No. 11/874,576, dated Apr. 26, 2016.
Written Opinion of International Search Authority for PCT/IL2012/000312, dated Jan. 8, 2013.
Written Opinion of International Search Authority for PCT/IL2013/050806, dated Feb. 10, 2014.
Written Opinion of International Search Authority for PCT/IL2012/000311, dated Feb. 13, 2013.
Written Opinion of International Search Authority for PCT/IL2012/000342, dated Feb. 25, 2013.
Written Opinion of International Search Authority for PCT/IL2012/000310, dated Feb. 28, 2013.
Written Opinion of International Search Authority for PCT/IL2008/000902, dated Mar. 2, 2009.
Written Opinion of International Search Authority for PCT/IL2014/050022, dated May 12, 2014.
Written Opinion of International Search Authority for PCT/IL2013/050183, dated Jun. 28, 2013.
Written Opinion of International Search Authority for PCT/IL2010/000330, dated Aug. 10, 2010.
Written Opinion of International Search Authority for PCT/IL2013/050216, dated Aug. 20, 2013.
Written Opinion of International Search Authority for PCT/IL2015/050345, dated Sep. 2, 2015.
Written Opinion of International Search Authority for PCT/IL2006/000478, dated Sep. 5, 2007.
Written Opinion of International Search Authority for PCT/IL2007/001161, dated Sep. 12, 2008.
Written Opinion of International Search Authority for PCT/IL2015/050579, dated Nov. 2, 2015.
Written Opinion of International Search Authority for PCT/IL2015/050349, dated Nov. 4, 2015.
Written Opinion of International Search Authority for PCT/IL2015/050718, dated Nov. 10, 2015.
Written Opinion of International Search Authority for PCT/IL2008/000994, dated Dec. 1, 2008.
Corresponding U.S. Appl. No. 15/129,925, filed Sep. 28, 2016 (not published yet).
Corresponding U.S. Appl. No. 15/317,121, filed Dec. 8, 2016 (not published yet).
Corresponding U.S. Appl. No. 15/322,452, filed Dec. 28, 2016 (not published yet).
Corresponding U.S. Appl. No. 15/393,286, filed Dec. 29, 2016 (not published yet).
Non-Final Rejection Office Action issued for U.S. Appl. No. 13/223,767, dated Jun. 14, 2012.
Response to Non-Final Rejection Office Action issued for U.S. Appl. No. 13/223,767, dated Jun. 14, 2012, as submitted on Sep. 13, 2012.
Requirement for Restriction/Election Office Action issued for U.S. Appl. No. 11/874,576, dated Dec. 31, 2009.
Response to Requirement for Restriction/Election Office Action issued for U.S. Appl. No. 11/874,576, dated Dec. 31, 2009, as submitted on Feb. 26, 2010.
Non-Final Rejection Office Action issued for U.S. Appl. No. 11/874,576, dated Apr. 19, 2010.
Response to Non-Final Rejection Office Action issued for U.S. Appl. No. 11/874,576, dated Apr. 19, 2010, as submitted on Oct. 19, 2010.
Final Rejection Office Action issued for U.S. Appl. No. 11/874,576, dated Jan. 4, 2011.
Response to Final Rejection Office Action issued for U.S. Appl. No. 11/874,576, dated Jan. 4, 2011, as submitted on Apr. 4, 2011.
Non-Final Rejection Office Action issued for U.S. Appl. No. 11/874,576, dated Apr. 13, 2012.
Response to Non-Final Rejection Office Action issued for U.S. Appl. No. 11/874,576, dated Apr. 13, 2012, as submitted on May 3, 2012.
Requirement for Restriction/Election Office Action issued for U.S. Appl. No. 11/874,534, dated Aug. 17, 2012.
Response to Requirement for Restriction/Election Office Action issued for U.S. Appl. No. 11/874,534, dated Aug. 17, 2012, as submitted on Dec. 16, 2012.
Written Opinion of International Search Authority for PCT/IL2012/000309, dated Feb. 7, 2013.
International Preliminary Report on Patentability (Chapter I) for PCT/IL2012/000309, dated Feb. 25, 2014.
Response to Requirement for Restriction/Election Office Action issued for U.S. Appl. No. 14/380,082, dated Sep. 26, 2016, as submitted on Mar. 22, 2017.
Response to Non-Final Rejection Office Action issued for U.S. Appl. No. 14/239,897 dated Oct. 7, 2016, as submitted on Mar. 23, 2017.

* cited by examiner

DEVICE AND METHOD FOR MANEUVERING ENDOSCOPE

FIELD OF THE INVENTION

The present invention generally relates to means and methods for simply maneuvering an endoscope by an endoscope user. Moreover, this present invention discloses a compact configuration of devices used for different actions upon the endoscope.

BACKGROUND OF THE INVENTION

In laparoscopic surgery, the surgeon performs the operation through small holes using long instruments and observing the internal anatomy with an endoscope camera. The endoscope is conventionally held by a camera assistant since the surgeon must perform the operation using both hands. The surgeon's performance is largely dependent on the camera's position relative to the instruments and on a stable image shown by the monitor; also the picture shown must be in the right orientation. The main problem is the difficulty for the assistant in keeping the endoscope in the right spatial position, holding the endoscope steadily, and keeping the scene in the right orientation. To overcome these problems, several new technologies have been developed, using robots to hold the endoscope while the surgeon performs the procedure, e.g., Lapman, Endoassist, etc. But these technologies are expensive, difficult to install, uncomfortable to use, limit the dexterity of the surgeon and have physical dimension much bigger that all the operating tools. Relative to the required action, they also move in big increments with several arms moving. Another robot, LER, (which was developed by the TIMC-GMCAO Laboratory) is described in US. Patent application No. 200/6100501. It consists of a compact camera-holder robot that rests directly on the patient's abdomen and an electronic box containing the electricity supply and robot controllers. LER has relatively small dimensions but has a 110 mm diameter base ring that must be attached, or be very close to, the patient's skin. This ring occupies space over the patient's body, affecting the surgeon's activities: limiting the surgeon's choice of where to place other trocars, changing the surgeon's usual way of making the procedure, sometimes forcing the setup process to be as long as 40 minutes. Also the LER has only 3 degrees of freedom and has no ability to control the orientation of the picture shown to surgeon (the LER cannot rotate the endoscope around its longitudinal axis).

Laparoscopic surgery is becoming increasingly popular with patients because the scars are smaller and their period of recovery is shorter. Laparoscopic surgery requires special training for the surgeon or gynecologist and the theatre nursing staff. The equipment is often expensive and is not available in all hospitals. During laparoscopic surgery, it is often required to shift the spatial placement of the endoscope in order to present the surgeon with an optimal view. Conventional laparoscopic surgery makes use of either human assistants that manually shift the instrumentation or alternatively robotic automated assistants (such as JP patent No. 06063003).

However, even the improved technologies still limit the dexterity of the surgeon and fail to provide four degrees of freedom. Another disadvantage of those technologies is the lack of ability to control the spatial position of an endoscope tube to any orientation during the laparoscopic surgery, such that the surgeon reaches any desired area within the working envelope in the body being operated on.

Therefore, there is still a long felt need for a camera holder that would allow holding and controlling the endoscope steady without limiting the dexterity of the surgeon and that will provide four degrees of freedom. Furthermore, there is still a long felt need for a camera holder that will provide the ability to control the spatial position of an endoscope tube to any orientation during the laparoscopic surgery, such that the surgeon reaches any desired area within the working envelope in operated body, without putting pressure on the penetration point where the endoscope enters the body.

SUMMARY OF THE INVENTION

It is an object of the invention to disclose a system for maneuvering an endoscope, comprising:

a. at least one first pivoting support adapted to be pivotally attached to the endoscope; the pivoting support adapted to enable the endoscope to pivot around at least one first axis of rotation;

b. at least one second pivoting support in communication with the at least one first pivoting support, the second pivoting support adapted to rotate around at least one axis being substantially orthogonal to the first axis of rotation independently of the first pivoting support; thereby enabling the endoscope to rotate around an insertion point into a body of a subject in at least two orthogonal axes;

c. at least one controller attached to either the first pivoting support or the second pivoting support, wherein the controller is adapted to provide a constant dynamic equilibrium between the endoscope and at least one of the first pivoting support or the second pivoting support.

It is another object of the invention to disclose the system as defined above, wherein at least one of the pivoting supports is adapted to moderate the pivoting of the endoscope around either the first axis of rotation or the second axis of rotation.

It is another object of the invention to disclose the system as defined above, wherein the system additionally comprises at least one connecting means adapted to connect the endoscope to at least one of the pivoting supports.

It is another object of the invention to disclose the system as defined above, wherein at least one of the pivoting supports is adapted to constantly apply a counter torque to oppose the torque induced by the endoscope and the connecting means.

It is another object of the invention to disclose the system as defined above, wherein the counter torque varies as the torque varies such that there is provided a constant dynamic equilibrium between the endoscope and at least one of the first pivoting support and the second pivoting support.

It is another object of the invention to disclose the system as defined above, wherein the first pivoting support is adapted to enable the endoscope to pivot around one first axis of rotation and the second pivoting support is adapted to enable the endoscope to pivot around a second and third axis of rotation, each of the first axis of rotation, the second axis of rotation and the third axis of rotation being substantially perpendicular to the other two axes of rotation.

It is another object of the invention to disclose the system as defined above, wherein the controller additionally comprises a damping mechanism adapted to prevent oscillation of the system.

It is another object of the invention to disclose the system as defined above, wherein the controller comprises at least one of an active mechanism and a passive mechanism to provide the dynamic equilibrium.

It is another object of the invention to disclose the system as defined above, wherein the controller comprises at least one selected from a group consisting of a motor and a spring.

It is another object of the invention to disclose the system as defined above, wherein the torque applied by the controller increases as the angle between the vertical and the endoscope increases.

It is another object of the invention to disclose the system as defined above, wherein activation of the control is at least one of a group consisting of: the control is activated at all times, the control is activated when the endoscope's angle is greater than a predetermined value, and the control is activated when the torque on the endoscope is greater than a predetermined value.

It is another object of the invention to disclose the system as defined above, wherein the system additionally comprises an automatic assistant in communication with the endoscope.

It is another object of the invention to disclose the system as defined above, wherein the automatic assistant is adapted to maneuver the endoscope.

It is another object of the invention to disclose the system as defined above, wherein the system additionally comprises an alignment mechanism.

It is another object of the invention to disclose the system as defined above, wherein the alignment mechanism is adapted to instruct the automatic assistant to align the endoscope.

It is another object of the invention to disclose the system as defined above, additionally comprising:
a. a first mechanism, comprising:
   i. at least one first transmission means 101; first transmission means 101 defines a first plane; first transmission means 101 is characterized by a first axis of rotation; the first axis of rotation is substantially orthogonal to the first plane;
   ii. at least one second transmission means 102; second transmission means 102 defines a second plane; the second transmission means is characterized by a second axis of rotation 141; second axis of rotation 141 is substantially orthogonal to the second plane; second transmission means 102 is rotatably connected to first transmission means 101; where the first plane is substantially orthogonal to second plane; and
   iii. at least one first means 106 adapted to rotate first transmission means 101 around the first axis of rotation;
   where first transmission means 101 transmits rotation to second transmission means 102; and,
b. a second mechanism, comprising:
   i. at least one third transmission means 103; third transmission means 103 defines a third plane; third transmission means 103 is characterized by a third axis of rotation; the third axis of rotation is substantially orthogonal to the third plane;
   ii. at least one fourth transmission means 104; fourth transmission means 104 defines a fourth plane; fourth transmission means 104 defines a fourth axis of rotation; the fourth axis of rotation is substantially orthogonal to fourth plane; fourth transmission means 104 is rotatably connected to third transmission means 103; where the fourth plane is substantially orthogonal to the third plane;
   iii. at least one fifth transmission means 105; fifth transmission means 105 defines a fifth plane; fifth transmission means 105 defines a fifth axis of rotation 142; fifth axis of rotation 142 is substantially orthogonal to the fifth plane; fifth transmission means 105 is rotatably connected to fourth transmission means 104; where the fifth plane is substantially orthogonal to the fourth plane;
   iv. at least one second means 107 adapted to rotate third transmission means 103 around the third axis of rotation;
   where third transmission means 103 transmits rotation to fourth transmission means 104;
   where fourth transmission means 104 transmits rotation to fifth transmission means 105.
wherein the first mechanism and the second mechanism are adapted to rotate the endoscope around at least one second axis of rotation 141 being substantially orthogonal to the second plane; and around at least one fifth axis of rotation 142 being substantially orthogonal to the fifth plane, such that second axis of rotation 141 and fifth axis of rotation 142 are positioned at an angle A relative to each other.

It is another object of the invention to disclose the system as defined above, wherein angle A between second axis of rotation 141 and fifth axis of rotation 142 is in the range of about 0 degrees to about 180 degrees.

It is another object of the invention to disclose the system as defined above, additionally comprising at least one zoom mechanism 115, adapted to maneuver the endoscope along its main longitudinal axis.

It is another object of the invention to disclose the system as defined above, wherein the zoom mechanism comprises:
a. at least one first coupling means clasped to the endoscope;
b. at least one first connecting means reversibly coupled to the endoscope at a first coupling position;
c. at least one second connecting means reversibly coupled to the first coupling means at a second coupling position;
wherein the coupling between the first connecting means, the second connecting means and the endoscope enables the endoscope to (i) pivot around the main longitudinal axis of the endoscope; and, (ii) to move along the longitudinal axis of the same.

It is another object of the invention to disclose the system as defined above, wherein the clasping enables reversible reciprocating movement along the main longitudinal axis of the endoscope.

It is another object of the invention to disclose the system as defined above, wherein the first connecting means and the second connecting means are connected to one another via joints.

It is another object of the invention to disclose the system as defined above, wherein the zoom mechanism additionally comprises m coupling means adapted to couple the first connecting means to the second connecting means; where m is an integer greater than or equal to one.

It is another object of the invention to disclose the system as defined above, wherein the m coupling means are rotatably coupled to each other.

It is another object of the invention to disclose the system as defined above, wherein the m coupling means are selected from a group consisting of joints, rods, other zoom mechanisms and any combination thereof.

It is another object of the invention to disclose the system as defined above, wherein the coupling of the endoscope to at least one of a group consisting of the first connecting means and the second connecting means is obtained by means selected from a group consisting of mechanical means, magnetic means and any combination thereof.

It is another object of the invention to disclose the system as defined above, wherein the mechanical means are selected from a group consisting of a clip, a fastening element, tape, adhesive tape, a snap fastener, a button and any combination thereof.

It is another object of the invention to disclose the system as defined above, wherein the magnetic means comprise a magnetic device, the magnetic device comprising at least one magnet and at least one selected from a group consisting of: a ferromagnet and a paramagnet.

It is another object of the invention to disclose the system as defined above, wherein the zoom mechanism is operable by at least one motor.

It is another object of the invention to disclose the system as defined above, where the third mechanism comprises a plurality of q joints, at least one of which is coupled to the pivoting support, and at least one of which is coupled to the second mechanism; where q is an integer greater than or equal to one.

It is another object of the invention to disclose the system as defined above, wherein the system is characterized by at least two configurations: an automatic configuration, in which the system is motorized; and a manual configuration in which the system is maneuvered manually by the endoscope user via a manual control mechanism, preferably a joystick, and wherein the system can be additionally characterized by a third configuration, a wholly manual configuration, in which a human endoscope assistant maneuvers the endoscope.

It is another object of the invention to disclose the system as defined above, wherein either one of the first or second pivoting supports (113 and 114) is a gimbal.

It is another object of the invention to disclose the system as defined above, wherein first transmission means 101, second transmission means 102, third transmission means 103, fourth transmission means 104, and fifth transmission means 105 are selected from a group consisting of gearwheels, wheels, crown gears, bevel gears, spur gears, belts, and any combination thereof.

It is another object of the invention to disclose the system as defined above, wherein the system comprises attaching means adapted to reversibly couple the system to a hospital bed, the attaching means selected from a group consisting of mechanical means, magnetic means and any combination thereof.

It is another object of the invention to disclose the system as defined above, wherein the mechanical means is selected from a group consisting of a clip, a fastening element, tape, adhesive tape, a snap fastener, a button and any combination thereof.

It is another object of the invention to disclose the system as defined above, wherein the magnetic means comprises a magnetic device, the magnetic device comprising at least one magnet and at least one selected from a group consisting of: a ferromagnet and a paramagnet;

where the magnetic is attached to at least one member of a group consisting of: a hospital bed, the system, and any combination thereof, and the member of the group consisting of a ferromagnet and a paramagnet is attached to at least one member of a group consisting of: a hospital bed, the system, and any combination thereof.

It is another object of the invention to disclose the system as defined above, wherein a rotation in the second plane defines an angle $\theta$.

It is another object of the invention to disclose the system as defined above, wherein the angle $\theta$ varies between about 0 and about 360 degrees, preferably between about 0 and about 160 degrees, when the system is in the automatic configuration or in the manual configuration.

It is another object of the invention to disclose the system as defined above, wherein a rotation in the fifth plane defines an angle kv.

It is another object of the invention to disclose the system as defined above, wherein the angle w varies between about 0 and about 360 degrees, preferably between about 0 and about 140 degrees, when system is in its automatic configuration or in its manual configuration.

It is another object of the invention to disclose the system as defined above, wherein the system additionally comprises a quick release handle adapted to disassemble the endoscope from the system when the system is in either its automatic configuration or its manual configuration.

It is another object of the invention to disclose the system as defined above, wherein the first mechanism additionally comprises locking means adapted to maintain in a predetermined orientation upon power failure at least one selected from a group consisting of: the first transmission means, the second transmission means and any combination thereof and to prevent any rotational movement of the same upon power failure.

It is another object of the invention to disclose the system as defined above, wherein the second mechanism additionally comprises locking means adapted to maintain in a predetermined orientation upon power failure at least one selected from a group consisting of: the third transmission means, the fourth transmission means, the fifth transmission means, and any combination thereof and to prevent any rotational movement of the same upon power failure.

It is another object of the invention to disclose the system as defined above, additionally comprising at least one manual override system (MOS), adapted upon activation of the same to switch reversibly between a manual configuration, in which the endoscope is moved manually by the operator and an automatic configuration, in which the endoscope is moved automatically by the system.

It is another object of the invention to disclose the system as defined above, additionally comprising at least one joystick, in communication with the endoscope.

It is another object of the invention to disclose the system as defined above, additionally comprising activation means adapted to activate at least one of a group consisting of the system, the joystick and any combination thereof.

It is another object of the invention to disclose the system as defined above, wherein the activation means is adapted to be worn by the MOS operator.

It is another object of the invention to disclose the system as defined above, adapted to be worn by the joystick user.

It is another object of the invention to disclose the system as defined above, wherein the activation means is selected from a group consisting of a pressable button, a rotatable knob, a knob, and any combination thereof.

It is another object of the invention to disclose the system as defined above, wherein the MOS enables rotation in the angles $\psi$ and $\theta$.

It is another object of the invention to disclose the system as defined above, wherein, when the joystick is moved in direction $\alpha$, the endoscope moves in angular direction $\theta$ and when the joystick is moved in direction $\beta$, the endoscope moves in angular direction $\psi$.

It is another object of the invention to disclose the system as defined above, wherein movement of the joystick in a direction selected from a group consisting of $\alpha$, $\beta$ and any combination thereof is proportional to movement of the endoscope in a direction selected from a group consisting of $\psi$, $\theta$ and any combination thereof.

It is another object of the invention to disclose the system as defined above, wherein the MOS additionally comprises means for controlling the endoscope's motion, adapted to moderate angular velocity in the θ and ψ directions.

It is another object of the invention to disclose the system as defined above, wherein the MOS additionally comprises n sensors, where n is an integer greater than or equal to one.

It is another object of the invention to disclose the system as defined above, wherein the sensors are selected from of a group consisting of motion sensors, heat sensors, electric sensors, sound sensors, pressure sensors, optical sensors and any combination thereof.

It is another object of the invention to disclose the system as defined above, wherein the sensors are activated in at least one selected from a group consisting of: in case of power failure and when the system is connected to power.

It is another object of the invention to disclose the system as defined above, wherein the motion sensors detect motion of the joystick.

It is another object of the invention to disclose the system as defined above, wherein the motion detection of the joystick is used to deactivate the motion of the endoscope if the motion's speed is above a predetermined threshold.

It is another object of the invention to disclose the system as defined above, wherein the joystick is characterized by an external surface.

It is another object of the invention to disclose the system as defined above, wherein the motion sensors detect motion upon the external surface.

It is another object of the invention to disclose the system as defined above, wherein the motion upon the external surface is used to operate the endoscope according to the motion upon the external surface.

It is another object of the invention to disclose the system as defined above, wherein the motion upon the external surface deactivates of the motion of the endoscope if the motion's speed is above a predetermined threshold.

It is another object of the invention to disclose the system as defined above, wherein the heat sensors are adapted to sense temperature in the range of about 35 to about 42 degrees.

It is another object of the invention to disclose the system as defined above, wherein the heat sensors enable activation of the MOS when the heat sensors sense a temperature is in the range of about 35 to about 42 degrees.

It is another object of the invention to disclose the system as defined above, wherein the heat sensors are adapted to provide a thermal image, where the heat sensors are coupled to a processing unit adapted to provide the endoscope user with the thermal image.

It is another object of the invention to disclose the system as defined above, wherein the processing unit enables the activation of the MOS upon analysis of the image and detection of a human hand.

It is another object of the invention to disclose the system as defined above, wherein the electric sensors are adapted to sense at least one of a group consisting of: power failure, connection to power, and electrical conductivity of a human body.

It is another object of the invention to disclose the system as defined above, wherein the the processing unit enables the activation of the MOS upon sensing the human body's conductivity by the electric sensors.

It is another object of the invention to disclose the system as defined above, wherein the sound sensors are adapted to sense predetermined sound patterns.

It is another object of the invention to disclose the system as defined above, wherein the sound sensors are used to operate the endoscope according to the predetermined sound patterns.

It is another object of the invention to disclose the system as defined above, wherein the optical sensors are adapted to sense visual changes according to predetermined visual patterns.

It is another object of the invention to disclose the system as defined above wherein the optical sensors are used to operate the endoscope according to the predetermined visual patterns.

It is another object of the invention to disclose the system as defined above, wherein the pressure sensors are adapted to sense pressure applied to the MOS.

It is another object of the invention to disclose the system as defined above, wherein the MOS is activated upon at least one condition selected from a group consisting of: analysis of the thermal image by the processing unit and detection of human hand, the electric sensors sense human body conductivity, the sound sensors sense predetermined sound patterns, and according to predetermined visual patterns detected by the optical sensors.

It is another object of the invention to disclose the system as defined above, wherein the MOS is adapted to change its activation state in a manner selected from at least one of a group consisting of: when the pressure sensed by the pressure sensors is above a predetermined threshold the MOS is activated, and when the pressure sensed by the pressure sensors is below a predetermined threshold, the MOS is de-activated.

It is another object of the invention to disclose the system as defined above, additionally comprising a surgical tracking system for assisting an operator to perform a laparoscopic surgery of a human body, the surgical tracking system comprising:

a. at least one endoscope adapted to acquire real-time images of a surgical environment within the human body;

b. a maneuvering subsystem adapted to control the spatial position of the endoscope during laparoscopic surgery; and, c. a tracking subsystem in communication with the maneuvering subsystem, adapted to control the maneuvering subsystem so as to direct and modify the spatial position of the endoscope to a region of interest;

wherein the tracking subsystem comprises a data processor; the data processor is adapted to perform real-time image processing of the surgical environment and to instruct the maneuvering subsystem to modify the spatial position of the endoscope according to input received from a maneuvering function f(t); the maneuvering function f(t) is adapted to (a) receive input from at least two instructing functions $g_i(t)$, where i is 1, . . . , n and n≥2; where t is time; i and n are integers; and, to (b) output instructions to the maneuvering subsystem based on the input from the at least two instructing functions $g_i(t)$, so as to spatially position the endoscope to the region of interest.

It is another object of the invention to disclose the system as defined above, wherein each of the instructing functions $g_i(t)$ is provided with $a_i(t)$ where is an integer greater than or equal to 1; where $a_i(t)$ are weighting functions of each $g_i(t)$, and n is the total number of instruction functions.

It is another object of the invention to disclose the system as defined above, wherein the weighting functions ai(t) are time-varying functions, wherein the value of which is determined by the operators.

It is another object of the invention to disclose the system as defined above, wherein each of the instructing functions $g_i(t)$ is selected from a group consisting of: most used tool function, right tool function, left tool function, field of view function, no fly zone function, proximity function, collision prevention function, preferred volume zone function, preferred tool function, tool detection function, movement detection function, organ detection function, operator input function, prediction function, past statistical analysis function, tagged tool function, and any combination thereof.

It is another object of the invention to disclose the system as defined above, wherein the most used tool function comprises a communicable database counting the amount of movement of each surgical tool located within the surgical environment; the most used tool function is adapted to output instructions to the tracking subsystem to instruct the maneuvering system to direct the endoscope to constantly position the endoscope to track the movement of the most moved surgical tool.

It is another object of the invention to disclose the system as defined above, wherein the right tool function is adapted to detect surgical tool positioned to right of the endoscope and to output instructions to the tracking subsystem to instruct the maneuvering system to constantly direct the endoscope on the right tool and to track the right tool.

It is another object of the invention to disclose the system as defined above, wherein the left tool function is adapted to detect surgical tool positioned to left of the endoscope and to output instructions to the tracking subsystem to instruct the maneuvering system to constantly direct the endoscope on the left tool and to track the left tool.

It is another object of the invention to disclose the system as defined above, wherein the field of view function comprises a communicable database comprising n 3D spatial positions; n is an integer greater than or equal to 2; the combination of all of the n 3D spatial positions provides a predetermined field of view; the field of view function is adapted to output instructions to the tracking subsystem to instruct the maneuvering system to direct the endoscope to at least one 3D spatial position substantially within the n 3D spatial positions so as to maintain a constant field of view.

It is another object of the invention to disclose the system as defined above, wherein the no fly zone function comprises a communicable database comprising n 3D spatial positions; n is an integer greater than or equal to 2; the n 3D spatial positions define a predetermined volume within the surgical environment; the no fly zone function is adapted to output instructions to the tracking subsystem to instruct the maneuvering system to direct the endoscope to at least one 3D spatial position substantially different from all the n 3D spatial positions.

It is another object of the invention to disclose the system as defined above, wherein the proximity function is adapted to define a predetermined distance between at least two surgical tools; and to output instructions to the tracking subsystem to instruct the maneuvering system to direct the endoscope to the two surgical tools if the distance between the two surgical tools is less than the predetermined distance.

It is another object of the invention to disclose the system as defined above, wherein the proximity function is adapted to define a predetermined angle between at least three surgical tools; and to output instructions to the tracking subsystem to instruct the maneuvering system to direct the endoscope to the three surgical tools if the angle between the three surgical tools is less than or greater than the predetermined angle.

It is another object of the invention to disclose the system as defined above, wherein the collision prevention function is adapted to define a predetermined distance between the at least one surgical tool and an anatomical element within the surgical environment; and to output instructions to the tracking subsystem to instruct the maneuvering system to direct the endoscope to the surgical tool and the anatomical element within the surgical environment if the distance between the at least one surgical tool and the anatomical element is less than the predetermined distance.

It is another object of the invention to disclose the system as defined above, wherein the preferred volume zone function comprises communicable database comprising n 3D spatial positions; n is an integer greater than or equal to 2; the n 3D spatial positions provide the preferred volume zone; the preferred volume zone function is adapted to output instructions to the tracking subsystem to instruct the maneuvering system to direct the endoscope to the preferred volume zone.

It is another object of the invention to disclose the system as defined above, wherein the preferred tool function comprises a communicable database, the database stores a preferred tool; the preferred tool function is adapted to output instructions to the tracking subsystem to instruct the maneuvering system to constantly direct the endoscope to the preferred tool, such that the endoscope constantly tracks the preferred tool.

It is another object of the invention to disclose the system as defined above, wherein the tool detection function is adapted to detect surgical tools in the surgical environment and to output instruction to the tracking subsystem to instruct the maneuvering system to direct the endoscope on the detected surgical tools.

It is another object of the invention to disclose the system as defined above, wherein the movement detection function comprises a communicable database comprising the real-time 3D spatial positions of each of the surgical tool in the surgical environment; is adapted to detect movement of the at least one surgical tool when a change in at least one of the 3D spatial positions is received, and is adapted to output instructions to the tracking subsystem to instruct the maneuvering system to direct the endoscope on the moved surgical tool.

It is another object of the invention to disclose the system as defined above, wherein the organ detection function is adapted to detect organs in the surgical environment and to output instructions to the tracking subsystem to instruct the maneuvering system to direct the endoscope on the detected organs.

It is another object of the invention to disclose the system as defined above, wherein the anatomical element is selected from a group consisting of tissue, organ, another surgical tool and any combination thereof.

It is another object of the invention to disclose the system as defined above, wherein the operator input function comprises a communicable database; the communicable database is adapted to receive an input from the operator of the system; the input comprising n 3D spatial positions; n is an integer greater than or equal to 2; and to output instructions to the tracking subsystem to instruct the maneuvering system to direct the endoscope to the at least one 3D spatial position received.

It is another object of the invention to disclose the system as defined above, wherein the prediction function comprises a communicable database storing each 3D spatial position of each surgical tool within the surgical environment, such that each movement of each surgical tool is stored; the prediction function is adapted to (a) to predict the future 3D spatial position of each of the surgical tools; and (b) to output instructions to the tracking subsystem to instruct the maneuvering system to direct the endoscope to the future 3D spatial position.

It is another object of the invention to disclose the system as defined above, wherein the past statistical analysis function comprises a communicable database storing each 3D spatial position of each of surgical tool within the surgical environment, such that each movement of each surgical tool is stored; the past statistical analysis function is adapted to (a) statistically analyze the 3D spatial positions of each of the surgical tools; and, (b) to predict the future 3D spatial position of each of the surgical tools; and (c) to output instructions to the tracking subsystem to instruct the maneuvering system to direct the endoscope to the future 3D spatial position.

It is another object of the invention to disclose the system as defined above, wherein the tagged tool function comprises means adapted to tag at least one surgical tool within the surgical environment and to output instructions to the tracking subsystem to instruct the maneuvering system to constantly direct the endoscope to the tagged surgical tool.

It is another object of the invention to disclose the system as defined above, wherein the means are adapted to apply a continuing tag to the at least one surgical tool within the surgical environment.

It is another object of the invention to disclose the system as defined above, wherein the means are adapted to re-tag the at least one of the surgical tools until a desired tool is selected.

It is another object of the invention to disclose the system as defined above, additionally comprising means adapted to toggle between the surgical tools.

It is another object of the invention to disclose the system as defined above, wherein toggling is performed manually or automatically.

It is another object of the invention to disclose the system as defined above, wherein the image processing is obtained by at least one algorithm selected from a group consisting of: image stabilization algorithm, image improvement algorithm, image compilation algorithm, image enhancement algorithm, image detection algorithm, image classification algorithm, image correlation with the cardiac cycle of the human body, image correlation with the respiratory cycle of the human body, smoke detection algorithm, vapor detection algorithm, algorithm for reducing steam from the endoscope and any combination thereof.

It is another object of the invention to disclose the system as defined above, wherein the endoscope comprises an image acquisition device selected from a group consisting of: a camera, a video camera, an electromagnetic sensor, a computer tomography imaging device, a fluoroscopic imaging device, an ultrasound imaging device, and any combination thereof.

It is another object of the invention to disclose the system as defined above, additionally comprising a display adapted to accept input from or provide output to the operator regarding operation of the system.

It is another object of the invention to disclose the system as defined above, wherein the display is used for visualizing the region of interest by the operator.

It is another object of the invention to disclose the system as defined above, wherein the display is adapted to output the acquired real-time images of a surgical environment with augmented reality elements.

It is another object of the invention to disclose the system as defined above, wherein the image processing algorithm is adapted to analyze 2D or 3D representation rendered from the real-time images of the surgical environment.

It is another object of the invention to disclose the system as defined above, wherein the data processor is further adapted to operate a pattern recognition algorithm for assisting the operation of the instructing functions $g_i(t)$.

It is another object of the invention to disclose the system as defined above, additionally comprising at least one location estimating means for locating the position of at least one surgical tool in the surgical environment.

It is another object of the invention to disclose the system as defined above, wherein the at least one location estimating means is an interface subsystem between a surgeon and the at least one surgical tool, the interface subsystem comprising:
a. at least one array comprising N regular or pattern light sources, where N is a positive integer;
b. at least one array comprising M cameras, where M is a positive integer;
c. optional optical markers and means for attaching at least one the optical marker to the at least one surgical tool; and,
d. a computerized algorithm operable via the controller, the computerized algorithm adapted to record images received by each camera of each of the M cameras and to calculate therefrom the position of each of the tools, and further adapted to provide automatically the results of the calculation to the human operator of the interface.

It is another object of the invention to disclose the system as defined above, additionally comprising a surgical controlling system, comprising:
a. at least one surgical tool adapted to be inserted into a surgical environment of a human body for assisting a surgical procedure;
b. at least one location estimating means adapted to locate in real-time the 3D spatial position of the at least one surgical tool at any given time t;
c. at least one movement detection means communicable with a movement's database and with the location estimating means; the movement's database is adapted to store the 3D spatial position of the at least one surgical tool at time $t_f$ and at time $t_0$; where $t_f > t_0$; the movement detection means is adapted to detect movement of the at least one surgical tool if the 3D spatial position of the at least one surgical tool at time $t_f$ is different from the 3D spatial position of the at least one surgical tool at time $t_0$; and,
d. a controller having a processing means communicable with a controller's database, the controller adapted to control the spatial position of the at least one surgical tool; the controller's database is in communication with the movement detection means;
wherein the controller's database is adapted to store a predetermined set of rules according to which ALLOWED and RESTRICTED movements of the at least one surgical tool are determined, such that each detected movement by the movement detection means of the at least one surgical tool is determined as either an ALLOWED movement or as a RESTRICTED movement according to the predetermined set of rules.

It is another object of the invention to disclose the system as defined above, wherein the predetermined set of rules comprises at least one rule selected from a group consisting of: most used tool rule, right tool rule, left tool rule, field of view rule, no fly zone rule, route rule, proximity rule; collision prevention rule, preferred volume zone rule, preferred tool rule, movement detection rule, operator input rule, environment rule, history-based rule, tool-dependent ALLOWED and RESTRICTED movements rule, tagged tool rule and any combination thereof.

It is another object of the invention to disclose the system as defined above, wherein the most used tool rule comprises a communicable database counting the amount of movement of each of the surgical tools; the most used tool rule is adapted to constantly position the endoscope to track the movement of the most moved surgical tool.

It is another object of the invention to disclose the system as defined above, wherein the right tool rule is adapted to determine the ALLOWED movement of the endoscope according to the movement of the surgical tool positioned to right of the endoscope; further wherein the left tool rule is adapted to determine the ALLOWED movement of the endoscope according to the movement of the surgical tool positioned to left of the endoscope.

It is another object of the invention to disclose the system as defined above, wherein the field of view rule comprises a communicable database comprising n 3D spatial positions; n is an integer greater than or equal to 2; the combination of all of the n 3D spatial positions provides a predetermined field of view; the field of view rule is adapted to determine the ALLOWED movement of the endoscope within the n 3D spatial positions so as to maintain a constant field of view, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the invention to disclose the system as defined above, wherein the no fly zone rule comprises a communicable database comprising n 3D spatial positions; n is an integer greater than or equal to 2; the n 3D spatial positions define a predetermined volume within the surgical environment; the no fly zone rule is adapted to determine the RESTRICTED movement if the movement is within the no fly zone and ALLOWED movement if the movement is outside the no fly zone, such that the RESTRICTED movements are movements in which the at least one of the surgical tool is located substantially in at least one of the n 3D spatial positions, and the ALLOWED movements are movements in which the location of the at least one surgical tool is substantially different from the n 3D spatial positions.

It is another object of the invention to disclose the system as defined above, wherein the route rule comprises a communicable database storing at least one predefined route in which the at least one surgical tool is adapted to move within the surgical environment; the predefined route comprises n 3D spatial positions of the at least one surgical tool; n is an integer greater than or equal to 2; the ALLOWED movements are movements in which the at least one surgical tool is located substantially in at least one of the n 3D spatial positions of the predefined route, and the RESTRICTED movements are movements in which the location of the at least one surgical tool is substantially different from the n 3D spatial positions of the predefined route.

It is another object of the invention to disclose the system as defined above, wherein the proximity rule is adapted to define a predetermined distance between at least two surgical tools; the ALLOWED movements are movements which are within the range or out of the range of the predetermined distance, and the RESTRICTED movements which are out of the range or within the range of the predetermined distance.

It is another object of the invention to disclose the system as defined above, wherein the proximity rule is adapted to define a predetermined angle between at least three surgical tools; the ALLOWED movements are movements which are within the range or out of the range of the predetermined angle, and the RESTRICTED movements which are out of the range or within the range of the predetermined angle.

It is another object of the invention to disclose the system as defined above, wherein the collision prevention rule is adapted to define a predetermined distance between the at least one surgical tool and an anatomical element within the surgical environment; the ALLOWED movements are movements which are in a range that is larger than the predetermined distance, and the RESTRICTED movements are movements which are in a range that is smaller than the predetermined distance.

It is another object of the invention to disclose the system as defined above, wherein the anatomical element is selected from a group consisting of tissue, organ, another surgical tool and any combination thereof.

It is another object of the invention to disclose the system as defined above, wherein the preferred volume zone rule comprises a communicable database comprising n 3D spatial positions; n is an integer greater than or equal to 2; the n 3D spatial positions provides the preferred volume zone; the preferred volume zone rule is adapted to determine the ALLOWED movement of the endoscope within the n 3D spatial positions and RESTRICTED movement of the endoscope outside the n 3D spatial positions, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the invention to disclose the system as defined above, wherein the preferred tool rule comprises a communicable database, the database stores a preferred tool; the preferred tool rule is adapted to determine the ALLOWED movement of the endoscope to constantly track the movement of the preferred tool.

It is another object of the invention to disclose the system as defined above, wherein the movement detection rule comprises a communicable database comprising the real-time 3D spatial positions of each of the at least one surgical tools; the movement detection rule is adapted to detect movement of the at least one surgical tool when a change in the 3D spatial positions is received, such that the ALLOWED movements are movements in which the endoscope is re-directed to focus on the moving surgical tool.

It is another object of the invention to disclose the system as defined above, wherein the operator input rule comprises a communicable database; the communicable database is adapted to receive an input from the operator of the system regarding the ALLOWED and RESTRICTED movements of the at least one surgical tool.

It is another object of the invention to disclose the system as defined above, wherein the input comprises n 3D spatial positions; n is an integer greater than or equal to 2; wherein at least one of which is defined as ALLOWED location and at least one of which is defined as RESTRICTED location, such that the ALLOWED movements are movements in which the at least one surgical tool is located substantially in at least one of the n 3D spatial positions, and the RESTRICTED movements are movements in which the location of the at least one surgical tool is substantially different from the n 3D spatial positions.

It is another object of the invention to disclose the system as defined above, wherein the input comprises at least one rule according to which ALLOWED and RESTRICTED movements of the at least one surgical tool are determined, such that the spatial position of the at least one surgical tool is controlled by the controller according to the ALLOWED and RESTRICTED movements.

It is another object of the invention to disclose the system as defined above, wherein the predetermined set of rules comprises at least one rule selected from a group consisting of: most used tool, right tool rule, left tool rule, field of view rule, no fly zone rule, route rule, environment rule, operator input rule, proximity rule; collision prevention rule, preferred volume zone rule, preferred tool rule, movement detection rule, history-based rule, tool-dependent ALLOWED and RESTRICTED movements rule, and any combination thereof.

It is another object of the invention to disclose the system as defined above, wherein the operator input rule converts an ALLOWED movement to a RESTRICTED movement and a RESTRICTED movement to an ALLOWED movement.

It is another object of the invention to disclose the system as defined above, wherein the environment rule comprises a communicable database; the communicable database is adapted to receive at least one real-time image of the surgical environment and is adapted to perform real-time image processing of the same and to determine the 3D spatial position of hazards or obstacles in the surgical environment; the environment rule is adapted to determine the ALLOWED and RESTRICTED movements according to the hazards or obstacles in the surgical environment, such that the RESTRICTED movements are movements in which the at least one surgical tool is located substantially in at least one of the 3D spatial positions of hazards or obstacles, and the ALLOWED movements are movements in which the location of the at least one surgical tool is substantially different from the 3D spatial positions of hazards or obstacles.

It is another object of the invention to disclose the system as defined above, wherein the hazards or obstacles in the surgical environment are selected from a group consisting of tissue, a surgical tool, an organ, an endoscope and any combination thereof.

It is another object of the invention to disclose the system as defined above, wherein the history-based rule comprises a communicable database storing each 3D spatial position of each of the at least one surgical tools, such that each movement of each surgical tool is stored; the history-based rule is adapted to determine the ALLOWED and RESTRICTED movements according to historical movements of the at least one surgical tool, such that the ALLOWED movements are movements in which the at least one surgical tool is located substantially in at least one of the 3D spatial positions comprised within at least one historical movement, and the RESTRICTED movements are movements in which the location of the at least one surgical tool is substantially different from the 3D spatial positions comprised within the historical movements.

It is another object of the invention to disclose the system as defined above, wherein s tool-dependent allowed and RESTRICTED movements rule comprises a communicable database; the communicable database is adapted to store predetermined characteristics of at least one of the surgical tools; the tool-dependent ALLOWED and RESTRICTED movements rule is adapted to determine the ALLOWED and RESTRICTED movements according to the predetermined characteristics of the surgical tool; such that allowed movements are movements of the endoscope which tracks the surgical tool having the predetermined characteristics.

It is another object of the invention to disclose the system as defined above, wherein the predetermined characteristics of the surgical tool are selected from a group consisting of: physical dimensions, structure, weight, sharpness, and any combination thereof.

It is another object of the invention to disclose the system as defined above, wherein the tagged tool rule comprises means adapted to tag at least one surgical tool within the surgical environment and to determine the ALLOWED movement of the endoscope to constantly track the movement of the tagged surgical tool.

It is another object of the invention to disclose the system as defined above, wherein at least one of the following is being held true (a) the system additionally comprises an endoscope; the endoscope is adapted to provide at least one real-time image of the surgical environment; (b) at least one of the surgical tools is an endoscope adapted to provide the at least one real-time image of the surgical environment.

It is another object of the invention to disclose the system as defined above, wherein the controller's database comprises n 3D spatial positions; n is an integer greater than or equal to 2; the combination of all of the n 3D spatial positions provides a predetermined field of view; the field of view rule is adapted to relocate the endoscope if movement of at least one of the surgical tools has been detected by the detection means, such that the field of view is maintained.

It is another object of the invention to disclose the system as defined above, wherein the system additionally comprises a maneuvering subsystem communicable with the controller, the maneuvering subsystem is adapted to spatially reposition the at least one surgical tool during a surgery according to the predetermined set of rules; further wherein the system is adapted to alert the physician of the RESTRICTED movement of the at least one surgical tool.

It is another object of the invention to disclose the system as defined above, wherein the alert is selected from a group consisting of audio signaling, voice signaling, light signaling, flashing signaling and any combination thereof.

It is another object of the invention to disclose the system as defined above, wherein the ALLOWED movement is permitted by the controller and the RESTRICTED movement is denied by the controller.

It is another object of the invention to disclose the system as defined above, additionally comprising a maneuvering subsystem communicable with the controller, the maneuvering subsystem is adapted to spatially reposition the at least one surgical tool during a surgery according to the predetermined set of rules, such that if the movement of the at least one surgical tool is a RESTRICTED movement, the maneuvering subsystem prevents the movement.

It is another object of the invention to disclose the system as defined above, wherein the at least one location estimating means comprises at least one endoscope adapted to acquire real-time images of the surgical environment within the human body; and at least one surgical instrument spatial location software adapted to receive the real-time images of the surgical environment and to estimate the 3D spatial position of the at least one surgical tool.

It is another object of the invention to disclose the system as defined above, wherein the at least one location estimating means comprises (a) at least one element selected from a group consisting of optical imaging means, radio frequency transmitting and receiving means, at least one mark on the at least one surgical tool and any combination thereof; and (b) at least one surgical instrument spatial location software adapted to estimate the 3D spatial position of the at least one surgical tool by means of the element.

It is another object of the invention to disclose the system as defined above, wherein the at least one location estimating means is an interface subsystem between a surgeon and the at least one surgical tool, the interface subsystem comprises:
a. at least one array comprising N regular or pattern light sources, where N is a positive integer;
b. at least one array comprising M cameras, where M is a positive integer;
c. none or more optical markers and means for attaching the optical markers to the at least one surgical tool; and;
d. a computerized algorithm operable via the controller, the computerized algorithm adapted to record images received by each camera of each of the M cameras and to calculate therefrom the position of each of the tools, and further adapted to provide automatically the results of the calculation to a human operator of the interface.

It is another object of the invention to disclose a method for maneuvering an endoscope, the method comprising steps of:
a. providing a system comprising:
  i. at least one first pivoting support adapted to be pivotally attached to the endoscope; the pivoting support adapted to enable the endoscope to pivot around at least one first axis of rotation;
  ii. at least one second pivoting support in communication with the at least one first pivoting support, the second pivoting support adapted to rotate around at least one axis being substantially orthogonal to the first axis of rotation independently of the first pivoting support; thereby enabling the endoscope to rotate around an insertion point into a body of a subject in at least two orthogonal axes;
  iii. at least one controller attached to either the first pivoting support or the second pivoting support
b. pivotally attaching the at least one first pivoting support to the endoscope;
c. positioning the at least one second pivoting support such that at least one axis of rotation of the at least one second pivoting support is substantially orthogonal to at least one axis of rotation of the at least one the first pivoting support;
d. attaching the at least one controller to at least one of the at least one first pivoting support and the at least one second pivoting support;
e. maneuvering the endoscope about the penetration point, thereby enabling maneuvering of the endoscope while maintaining alignment of the endoscope about the penetration point.

It is another object of the invention to disclose the method as defined above, additionally comprising steps of adapting at least one of the pivoting supports to moderate the pivoting of the endoscope around either the first axis of rotation or the second axis of rotation.

It is another object of the invention to disclose the method as defined above, additionally comprising steps of providing at least one connecting means in connection with the endoscope and at least one of the pivoting supports.

It is another object of the invention to disclose the method as defined above, additionally comprising steps of adapting at least one of the pivoting supports to constantly apply a counter torque to oppose the torque induced by the endoscope and the connecting means.

It is another object of the invention to disclose the method as defined above, additionally comprising steps of varying the counter torque as the torque varies, thereby enabling a constant dynamic equilibrium between the endoscope and at least one of the first pivoting support and the second pivoting support.

It is another object of the invention to disclose the method as defined above, additionally comprising steps of adapting the first pivoting support to enable the endoscope to pivot around one first axis of rotation and adapting the second pivoting support to enable the endoscope to pivot around a second and third axis of rotation, each of the first axis of rotation, the second axis of rotation and the third axis of rotation being substantially perpendicular to the other two axes of rotation.

It is another object of the invention to disclose the method as defined above, additionally comprising steps of providing the controller with a damping mechanism adapted to prevent oscillation of the system.

It is another object of the invention to disclose the method as defined above, additionally comprising steps of providing the controller with at least one of an active mechanism and a passive mechanism to provide the dynamic equilibrium.

It is another object of the invention to disclose the method as defined above, additionally comprising steps of providing the controller with at least one of a group consisting of: a motor and a spring mechanism to provide the dynamic equilibrium.

It is another object of the invention to disclose the method as defined above, additionally comprising steps of increasing the torque applied by the controller as the angle between the vertical and the endoscope increases.

It is another object of the invention to disclose the method as defined above, additionally comprising steps of enabling the control to be activated by at least one of a group consisting of: the control is activated at all times, the control is activated when the endoscope's angle is greater than a predetermined value, and the control is activated when the torque on the endoscope is greater than a predetermined value.

It is another object of the invention to disclose the method as defined above, additionally comprising steps of providing the system with automatic assistance in communication with the endoscope.

It is another object of the invention to disclose the method as defined above, additionally comprising steps of adapting the automatic assistance to maneuver the endoscope.

It is another object of the invention to disclose the method as defined above, additionally comprising steps of providing the system with an alignment mechanism.

It is another object of the invention to disclose the method as defined above, additionally comprising steps of adapting the alignment mechanism to instruct the automatic assistance to align the endoscope.

It is another object of the invention to disclose the method as defined above, additionally comprising steps of:
a. providing a system comprising:
  i. a first mechanism, comprising:
    a) at least one first transmission means 101; first transmission means 101 defines a first plane; first transmission means 101 is characterized by a first axis of rotation; the first axis of rotation is substantially orthogonal to the first plane;
    b) at least one second transmission means 102; second transmission means 102 defines a second plane; second transmission means 102 defines a second axis of rotation; the second axis of rotation is substantially orthogonal to the second plane; second transmission means 102 is rotatably connected to first transmission means 101; where the first plane is substantially orthogonal to second plane; and c) at least one first means 106 adapted to rotate first transmission means 101 around the first axis of rotation;

ii. a second mechanism, comprising:

a) at least one third transmission means 103; third transmission means 103 defines a third plane; third transmission means 103 is characterized by a third axis of rotation; the third axis of rotation is substantially orthogonal to the third plane;

b) at least one fourth transmission means 104; fourth transmission means 104 defines a fourth plane; fourth transmission means 104 defines a fourth axis of rotation; the fourth axis of rotation is substantially orthogonal to the fourth plane; the fourth transmission means 104 is rotatably connected to third transmission means 103; the fourth plane is substantially orthogonal to the third plane;

c) at least one fifth transmission means 105; fifth transmission means 105 defines a fifth plane; fifth transmission means 105 defines a fifth axis of rotation; the fifth axis of rotation is substantially orthogonal to the fifth plane; fifth transmission means 105 is rotatably connected to fourth transmission means 104; the fifth plane is substantially orthogonal to the fourth plane;

d) at least one second means 107 adapted to rotate third transmission means 103 around the third axis of rotation;

b. positioning first transmission means 101 orthogonal to second transmission means 102; the positioning enables transmission of rotation between first transmission means 101 and second transmission means 102;

c. positioning third transmission means 103 orthogonal to fourth transmission means 104; the positioning enables transmission of rotation between third transmission means 103 and fourth transmission means 104.

d. positioning fourth transmission means 104 orthogonal to fifth transmission means 105; the positioning enables transmission of rotation between fourth transmission means 104 and fifth transmission means 105.

e. coupling second transmission means 102 to the endoscope and fifth transmission means 105 to the endoscope; the coupling enables rotation of the endoscope proportional to rotation of second transmission means 102 and fifth transmission means 105; and, f. maneuvering the endoscope in at least two degrees of freedom (DOF); maneuvering of the endoscope in the at least two degrees of freedom are in second axis of rotation 141 and in fifth axis of rotation 142;

wherein maneuvering in a first DOF of the at least two DOF is performed by a step of rotating first transmission means 101 thereby transmitting rotation to the endoscope; wherein maneuvering in a second DOF of at least two DOF is performed by a step of rotating third transmission means 103 thereby transmitting rotation to the endoscope.

It is another object of the invention to disclose the method as defined above, additionally comprising steps of defining an angle A between second axis of rotation 141 and fifth axis of rotation 142; angle A is in the range of about 0 degrees to about 180 degrees.

It is another object of the invention to disclose the method as defined above, additionally comprising steps of a. providing at least one zoom mechanism 115; and b. maneuvering the endoscope along the main longitudinal axis of the same.

It is another object of the invention to disclose the method as defined above, additionally comprising steps of providing the zoom mechanism with:

a. at least one first coupling means clasped to the endoscope, b. at least one first connecting means reversibly coupled to the endoscope at a first coupling position;

c. at least one second connecting means reversibly coupled to the first coupling means at a second coupling position;

wherein the coupling between the first connecting means, the second connecting means and the endoscope enables the first and the second connecting means (i) to pivot around the main longitudinal axis of the endoscope; and (ii) to move along the longitudinal axis of the same.

It is another object of the invention to disclose the method as defined above, additionally comprising steps of enabling the first coupling means clasped to the endoscope to move with a reversible reciprocating movement along the main longitudinal axis of the endoscope.

It is another object of the invention to disclose the method as defined above, additionally comprising steps of connecting the first connecting means and the second connecting means to one another via joints.

It is another object of the invention to disclose the method as defined above, additionally comprising steps of providing the zoom mechanism with m coupling means adapted to couple the first connecting means to the second connecting means; where m is an integer larger or equal to one.

It is another object of the invention to disclose the method as defined above, additionally comprising steps of rotatably coupling the m coupling means to each other.

It is another object of the invention to disclose the method as defined above, additionally comprising steps of selecting the m coupling means from a group consisting of: joints, rods, other zoom mechanisms and any combination thereof.

It is another object of the invention to disclose the method as defined above, additionally comprising steps of selecting the coupling means from a group consisting of mechanical means, magnetic means and any combination thereof.

It is another object of the invention to disclose the method as defined above, additionally comprising steps of selecting the mechanical means from a group consisting of a clip, a fastening element, tape, adhesive tape, a snap fastener, a button and any combination thereof.

It is another object of the invention to disclose the method as defined above, additionally comprising steps of operating the zoom mechanism by at least one motor.

It is another object of the invention to disclose the method as defined above, additionally comprising steps of selecting the pivoting support to be a gimbal.

It is another object of the invention to disclose the method as defined above, additionally comprising steps of providing the third mechanism with a plurality of q joints, at least one of which is coupled to the pivoting support, and at least one of which is coupled to the second mechanism; where q is an integer greater than or equal to one.

It is another object of the invention to disclose the method as defined above, additionally comprising steps of characterizing the system by at least two configurations: an automatic configuration, in which the system is motorized; and a manual configuration in which the system is maneuvered manually by the endoscope user via a manual control mechanism, preferably a joystick, and wherein the system can be additionally characterized by a third configuration, a wholly manual configuration, in which a human endoscope assistant maneuvers the endoscope.

It is another object of the invention to disclose the method as defined above, additionally comprising steps of selecting at least one of the first and second pivoting supports (113 and 114) to be a gimbal.

It is another object of the invention to disclose the method as defined above, additionally comprising steps of a. selecting first transmission means 101, second transmission means 102, third transmission means 103, fourth transmission means 104, and fifth transmission means 105 from a group consisting of gearwheels, wheels, crown gears, bevel gears, spur gears, belts, and any combinations thereof and b. providing the system with attaching means adapted to reversibly couple the system to a hospital bed, the attaching means selected from a group consisting of mechanical means, magnetic means and any combination thereof.

It is another object of the invention to disclose the method as defined above, additionally comprising steps of selecting the mechanical means from a group consisting of a clip, a fastening element, tape, adhesive tape, a snap fastener, a button and any combination thereof.

It is another object of the invention to disclose the method as defined above, additionally comprising steps of providing, as the magnetic means, a magnetic device comprising at least one magnet and at least one selected from a group consisting of a ferromagnet and a paramagnet; where the magnet is attached to any member of a group consisting of: a hospital bed, the system, and any combination thereof, and at least one selected from a group consisting of a ferromagnet and a paramagnet is attached to at least one member of a group consisting of: a hospital bed, the system, and any combination thereof.

It is another object of the invention to disclose the method as defined above, additionally comprising steps of defining an angle $\theta$ for rotation in the second plane, the angle $\theta$ to vary between about 0 and about 360 degrees, preferably between about 0 and about 160 degrees, when the system is in its automatic configuration or in its manual configuration.

It is another object of the invention to disclose the method as defined above, additionally comprising steps of defining an angle $\psi$ for rotation in the fifth plane, the angle $\psi$ to vary between about 0 and about 360 degrees, preferably between about 0 and about 140 degrees, when the system is in its automatic configuration or in its manual configuration.

It is another object of the invention to disclose the method as defined above, additionally comprising steps of additionally providing the system with a quick release handle adapted to disassemble the endoscope from the system when the system is in its automatic configuration or in its manual configuration.

It is another object of the invention to disclose the method as defined above, additionally comprising steps of providing the first mechanism with locking means adapted to maintain in a predetermined orientation upon power failure at least one selected from a group consisting of: the first transmission means, the second transmission means and any combination thereof; and to prevent any rotational movement of the same upon power failure.

It is another object of the invention to disclose the method as defined above, additionally comprising steps of providing the second mechanism additionally with locking means adapted to maintain in a predetermined orientation upon power failure at least one selected from a group consisting of: the third transmission means, the fourth transmission means, the fifth transmission means, and any combination thereof and to prevent any rotational movement of the same upon power failure.

It is another object of the invention to disclose the method as defined above, additionally comprising steps of providing at least one manual override system (MOS), adapted upon activation of the same to switch reversibly between a manual configuration, in which the endoscope is moved manually by the operator and an automatic configuration, in which the endoscope is moved automatically by the system and optionally additionally comprising steps of enabling the same to switch reversibly to a third configuration, in which the endoscope is moved wholly manually by an endoscope assistant.

It is another object of the invention to disclose the method as defined above, additionally comprising steps of providing at least one joystick, in communication with the endoscope.

It is another object of the invention to disclose the method as defined above, additionally comprising steps of providing activation means adapted to activate at least one of a group consisting of the system, the joystick and any combination thereof.

It is another object of the invention to disclose the method as defined above, additionally comprising steps of enabling the joystick to be worn by the joystick user.

It is another object of the invention to disclose the method as defined above, additionally comprising steps of enabling the activation means to be worn by the MOS user.

It is another object of the invention to disclose the method as defined above, additionally comprising steps of selecting the activation means from a group consisting of a pressable button, a rotatable knob, a knob, and any combination thereof.

It is another object of the invention to disclose the method as defined above, additionally comprising steps of enabling the MOS to rotate in the angles $\psi$ and $\theta$.

It is another object of the invention to disclose the method as defined above, additionally comprising steps of defining angles $\alpha$ and $\beta$ such that the endoscope moves in angular direction $\theta$ when the joystick is moved in direction $\alpha$, and the endoscope moves in angular direction $\psi$ when the joystick is moved in direction $\beta$.

It is another object of the invention to disclose the method as defined above, wherein movement of the joystick in a direction selected from a group consisting of $\alpha$, $\beta$ and any combination thereof, is proportional to movement of the endoscope in angular directions $\psi$, $\theta$ and any combination thereof.

It is another object of the invention to disclose the method as defined above, additionally comprising steps of providing the MOS with means for controlling the endoscope motion, adapted to moderate angular velocity in the $\theta$ and $\psi$ directions.

It is another object of the invention to disclose the method as defined above, additionally comprising steps of providing the MOS with n sensors, where n is an integer greater than or equal to one.

It is another object of the invention to disclose the method as defined above, additionally comprising steps of selecting the sensors from of a group consisting of: motion sensors, heat sensors, electric sensors, sound sensors, pressure sensors, optical sensors and any combination thereof.

It is another object of the invention to disclose the method as defined above, additionally comprising steps selected from at least one of the following: activating the n sensors in case of power failure and activating the n sensors when the system is connected to power.

It is another object of the invention to disclose the method as defined above, additionally comprising steps of detecting the motion of the joystick with motion sensors.

It is another object of the invention to disclose the method as defined above, additionally comprising steps of using the motion detection of the joystick for deactivation of the motion of the endoscope if the motion's speed is above a predetermined threshold.

It is another object of the invention to disclose the method as defined above, additionally comprising steps of characterizing the joystick by an external surface.

It is another object of the invention to disclose the method as defined above, additionally comprising steps of operating the motion sensors to detect motion upon the external surface.

It is another object of the invention to disclose the method as defined above, additionally comprising steps of operating the endoscope according to the motion upon the external surface.

It is another object of the invention to disclose the method as defined above, additionally comprising steps of deactivation of the motion of the endoscope when the motion's speed along the joystick is above a predetermined threshold.

It is another object of the invention to disclose the method as defined above, additionally comprising steps of adapting the heat sensors to sense temperatures in the range of about 35 to about 42 degrees.

It is another object of the invention to disclose the method as defined above, additionally comprising steps of enabling the activation of the MOS when the heat sensors sense that the temperature is in the range of about 35 to about 42 degrees.

It is another object of the invention to disclose the method as defined above, additionally comprising steps of adapting the heat sensors to provide at least one thermal image, where the heat sensors are coupled to a processing unit adapted to provide the endoscope user with the thermal image.

It is another object of the invention to disclose the method as defined above, additionally comprising steps of enabling the activation of the MOS when the heat sensors sense temperature is in the range of about 35 to about 42 degrees.

It is another object of the invention to disclose the method as defined above, additionally comprising steps of adapting the electric sensors to sense at least one of a group consisting of: power failure, connection to power and electrical conductivity of human body.

It is another object of the invention to disclose the method as defined above, additionally comprising steps of enabling the activation of the MOS upon sensing the human body's conductivity by the electric sensors.

It is another object of the invention to disclose the method as defined above, additionally comprising steps of adapting the sound sensors to sense predetermined sound patterns.

It is another object of the invention to disclose the method as defined above, additionally comprising steps of operating the endoscope according to predetermined sound patterns sensed by the sound sensors.

It is another object of the invention to disclose the method as defined above, additionally comprising steps of adapting the optical sensors to sense visual changes according to predetermined visual patterns.

It is another object of the invention to disclose the method as defined above, additionally comprising steps of operating the endoscope according to predetermined visual patterns detected by the sensors.

It is another object of the invention to disclose the method as defined above, additionally comprising steps of adapting the pressure sensors to sense pressure applied to the MOS.

It is another object of the invention to disclose the method as defined above, additionally comprising steps selected from at least one of a group consisting of: activating the MOS when the pressure sensed by the pressure sensors is above a predetermined threshold and de-activating the MOS when the pressure sensed by the pressure sensors is below a predetermined threshold.

It is another object of the invention to disclose the method as defined above, additionally comprising steps of enabling the activation of the MOS upon at least one condition selected from a group consisting of: analysis of the thermal image by the processing unit and detection of a human hand, the electric sensors sense the human body conductivity, the sound sensors sense the predetermined sound patterns, and according to the predetermined visual patterns detected by the optical sensors.

It is another object of the invention to disclose the method as defined above, additionally comprising steps of altering the activation state of the MOS under at least one condition selected from a group consisting of: when the pressure sensed by the pressure sensors is above a predetermined threshold the MOS is activated, and when the pressure sensed by the pressure sensors is below a predetermined threshold, the MOS is de-activated.

It is another object of the invention to disclose the method as defined above, additionally comprising steps of adapting the endoscope to acquire real-time images of a surgical environment within the human body.

It is another object of the invention to disclose the method as defined above, additionally comprising a step of providing a surgical tracking system (STS) for assisting an operator to perform laparoscopic surgery on a human body; the STS comprising steps of:

a. providing a surgical tracking system, comprising: (i) at least one endoscope adapted to acquire real-time images of a surgical environment within the human body; (ii) a maneuvering subsystem in communication with the endoscope; and, (iii) a tracking subsystem in communication with the maneuvering subsystem, the tracking subsystem comprises a data processor;

b. performing real-time image processing of the surgical environment; and c. controlling the maneuvering system via the tracking subsystem, thereby directing and modifying the spatial position of the endoscope to a region of interest according to input received from a maneuvering function f(t);

wherein the maneuvering function f(t) is adapted to (a) receive input from at least two instructing functions $g_i(t)$, where i is 1, . . . , n and n≥2; where t is time; i and n are integers; and, to (b) output instructions to the maneuvering subsystem based on the input from the at least two instructing functions $g_i(t)$, so as to spatially position the endoscope to the region of interest.

It is another object of the invention to disclose the method as defined above, wherein each of the instructing functions $g_i(t)$ is provided with ai(t) where i is an integer greater than or equal to 1; where $a_i(t)$ are weighting functions of each $g_i(t)$, and n is the total number of instruction functions.

It is another object of the invention to disclose the method as defined above, wherein the weighting functions $a_1(t)$ are time-varying functions, wherein the value of which is determined by the operators.

It is another object of the invention to disclose the method as defined above, wherein each of the instructing functions $g_i(t)$ is selected from a group consisting of: most used tool function, right tool function, left tool function, field of view function, no fly zone function, proximity function, collision prevention function, preferred volume zone function, preferred tool function, tool detection function, movement detection function, organ detection function, operator input function, prediction function, past statistical analysis function, tagged tool function and any combination thereof.

It is another object of the invention to disclose the method as defined above, wherein the most used tool function comprises a communicable database counting the amount of movement of each surgical tool located within the surgical environment; the most used tool function is adapted to output instructions to the tracking subsystem to instruct the maneuvering system to direct the endoscope to constantly position the endoscope to track the movement of the most moved surgical tool.

It is another object of the invention to disclose the method as defined above, wherein the right tool function is adapted to detect surgical tool positioned to right of the endoscope and to output instructions to the tracking subsystem to instruct the maneuvering system to constantly direct the endoscope on the right tool and to track the right tool.

It is another object of the invention to disclose the method as defined above, wherein the left tool function is adapted to detect surgical tool positioned to left of the endoscope and to output instructions to the tracking subsystem to instruct the maneuvering system to constantly direct the endoscope on the left tool and to track the left tool.

It is another object of the invention to disclose the method as defined above, wherein the field of view function comprises a communicable database comprising n 3D spatial positions; n is an integer greater than or equal to 2; the combination of all of the n 3D spatial positions provides a predetermined field of view; the field of view function is adapted to output instructions to the tracking subsystem to instruct the maneuvering system to direct the endoscope to at least one 3D spatial position substantially within the n 3D spatial positions so as to maintain a constant field of view.

It is another object of the invention to disclose the method as defined above, wherein controller's database comprises n 3D spatial positions; n is an integer greater than or equal to 2; the combination of all of the n 3D spatial positions provides a predetermined field of view; the field of view rule is adapted to relocate the endoscope if movement of at least one of the surgical tools has been detected by the detection means, such that the field of view is maintained.

It is another object of the invention to disclose the method as defined above, wherein the no fly zone function comprises a communicable database comprising n 3D spatial positions; n is an integer greater than or equal to 2; the n 3D spatial positions define a predetermined volume within the surgical environment; the no fly zone function is adapted to output instructions to the tracking subsystem to instruct the maneuvering system to direct the endoscope to at least one 3D spatial position substantially different from all the n 3D spatial positions.

It is another object of the invention to disclose the method as defined above, wherein the proximity function is adapted to define a predetermined distance between at least two surgical tools; and to output instructions to the tracking subsystem to instruct the maneuvering system to direct the endoscope to the two surgical tools if the distance between the two surgical tools is less than the predetermined distance.

It is another object of the invention to disclose the method as defined above, wherein the proximity function is adapted to define a predetermined angle between at least three surgical tools; and to output instructions to the tracking subsystem to instruct the maneuvering system to direct the endoscope to the three surgical tools if the angle between the surgical tools is less than or greater than the predetermined angle.

It is another object of the invention to disclose the method as defined above, wherein the collision prevention function is adapted to define a predetermined distance between the at least one surgical tool and an anatomical element within the surgical environment; and to output instructions to the tracking subsystem to instruct the maneuvering system to direct the endoscope to the surgical tool and the anatomical element within the surgical environment if the distance between the at least one surgical tool and an anatomical element is less than the predetermined distance.

It is another object of the invention to disclose the method as defined above, wherein the anatomical element is selected from a group consisting of tissue, organ, another surgical tool and any combination thereof.

It is another object of the invention to disclose the method as defined above, wherein the preferred volume zone function comprises a communicable database comprising n 3D spatial positions; n is an integer greater than or equal to 2; the n 3D spatial positions provide the preferred volume zone; the preferred volume zone function is adapted to output instructions to the tracking subsystem to instruct the maneuvering system to direct the endoscope to the preferred volume zone.

It is another object of the invention to disclose the method as defined above, wherein the preferred tool function comprises a communicable database, the database stores a preferred tool; the preferred tool function is adapted to output instructions to the tracking subsystem to instruct the maneuvering system to constantly direct the endoscope to the preferred tool, such that the endoscope constantly tracks the preferred tool.

It is another object of the invention to disclose the method as defined above, wherein the tool detection function is adapted to detect surgical tools in the surgical environment and to output instructions to the tracking subsystem to instruct the maneuvering system to direct the endoscope on the detected surgical tools.

It is another object of the invention to disclose the method as defined above, wherein the movement detection function comprises a communicable database comprising real-time 3D spatial positions of each surgical tool in the surgical environment; and to detect movement of at least one surgical tool when a change in the 3D spatial positions is received, and to output instructions to the tracking subsystem to instruct the maneuvering system to direct the endoscope on the moved surgical tool.

It is another object of the invention to disclose the method as defined above, wherein the organ detection function is adapted to detect at least one organ in the surgical environment and to output instructions to the tracking subsystem to instruct the maneuvering system to direct the endoscope on the detected organs.

It is another object of the invention to disclose the method as defined above, wherein the operator input function comprises a communicable database; the communicable database is adapted to receive an input from the operator of the system; the input comprising n 3D spatial positions; n is an integer greater than or equal to 2; and to output instructions to the tracking subsystem to instruct the maneuvering system to direct the endoscope to the at least one 3D spatial position received from the operator.

It is another object of the invention to disclose the method as defined above, wherein the prediction function comprises a communicable database storing each 3D spatial position of each surgical tool within the surgical environment, such that each movement of each surgical tool is stored; the prediction function is adapted to (a) to predict the future 3D spatial position of each of the surgical tools; and (b) to output instructions to the tracking subsystem to instruct the maneuvering system to direct the endoscope to the future 3D spatial position.

It is another object of the invention to disclose the method as defined above, wherein the past statistical analysis function comprises a communicable database storing each 3D spatial position of each surgical tool within the surgical environment, such that each movement of each surgical tool is stored; the past statistical analysis function is adapted to (a) statistically analyze the 3D spatial positions of each of the surgical tools; and, (b) to predict future 3D spatial positions of each of the surgical tools; and (c) to output instructions to the tracking subsystem to instruct the maneuvering system to direct the endoscope to at least one future 3D spatial position.

It is another object of the invention to disclose the method as defined above, wherein the tagged tool function comprises tagging means adapted to tag at least one surgical tool within the surgical environment and to output instructions to the tracking subsystem to instruct the maneuvering system to constantly direct the endoscope to the tagged surgical tool.

It is another object of the invention to disclose the method as defined above, wherein the tagging means are adapted to apply a continuing tag to the at least one of surgical tool within the surgical environment.

It is another object of the invention to disclose the method as defined above, wherein means are adapted to re-tag at least one of the surgical tools until a desired tool is selected.

It is another object of the invention to disclose the method as defined above, additionally comprising a step of providing means adapted to toggle between surgical tools.

It is another object of the invention to disclose the method as defined above, wherein the toggling is performed manually or automatically.

It is another object of the invention to disclose the method as defined above, wherein the image processing is obtained by at least one algorithm selected from a group consisting of: image stabilization algorithm, image improvement algorithm, image compilation algorithm, image enhancement algorithm, image detection algorithm, image classification algorithm, image correlation with the cardiac cycle or the respiratory cycle of the human body, smoke detection algorithm, vapor detection algorithm, algorithm to reduce steam from the endoscope and any combination thereof.

It is another object of the invention to disclose the method as defined above, wherein the endoscope comprises an image acquisition device selected from a group consisting of: a camera, a video camera, an electromagnetic sensor, a computer tomography imaging device, a fluoroscopic imaging device, an ultrasound imaging device, and any combination thereof.

It is another object of the invention to disclose the method as defined above, additionally comprising steps of providing a display adapted to accept input from or provide output to the operator regarding the operation of the system.

It is another object of the invention to disclose the method as defined above, wherein the display is used for visualizing the region of interest by the operator.

It is another object of the invention to disclose the method as defined above, wherein the display is adapted to output the acquired real-time images of a surgical environment with augmented reality elements.

It is another object of the invention to disclose the method as defined above, wherein the image processing algorithm is adapted to analyze 2D or 3D representations rendered from real-time images of the surgical environment.

It is another object of the invention to disclose the method as defined above, wherein the data processor is further adapted to operate a pattern recognition algorithm for assisting the operation of the instructing functions $g_i(t)$.

It is another object of the invention to disclose the method as defined above, additionally comprising a step of preliminarily tagging at least one of the surgical tools.

It is another object of the invention to disclose the method as defined above, additionally comprising step of applying a continuing tag to at least one of the surgical tools.

It is another object of the invention to disclose the method as defined above, additionally comprising a step of re-tagging the at least one of the surgical tools until a desired tool is selected.

It is another object of the invention to disclose the method as defined above, additionally comprising a step of toggling between the surgical tools.

It is another object of the invention to disclose the method as defined above, wherein the toggling is performed manually or automatically.

It is another object of the invention to disclose the method as defined above, additionally comprising a step of locating the 3D position of at least one surgical tool in the surgical environment.

It is another object of the invention to disclose the method as defined above, wherein the step of locating the 3D position of the at least one surgical tool is provided by at least one location estimating means; the at least one location estimating means is an interface subsystem between a surgeon and the at least one surgical tool, the interface subsystem comprising:
a. at least one array comprising N regular or pattern light sources, where N is a positive integer;
b. at least one array comprising M cameras, where M is a positive integer;
c. none or more optical markers and means for attaching the optical marker to the at least one surgical tool; and
d. a computerized algorithm operable via the controller, the computerized algorithm adapted to record images received by each of the M cameras and to calculate therefrom the position of each of the tools, and further adapted to provide automatically the results of the calculation to the human operator of the interface.

It is another object of the invention to disclose the method as defined above, additionally comprising a step of providing a surgical controlling system (SCS) for assisting an operator to perform laparoscopic surgery on a human body; the SCS comprising steps of:
a. providing a surgical controlling system, comprising: (i) at least one surgical tool; (ii) at least one location estimating means; (iii) at least one movement detection means; and (iv) a controller having a processing means communicable with the controller's database;
b. inserting the at least one surgical tool into a surgical environment of a human body;
c. estimating in real-time the location of the at least one surgical tool within the surgical environment at any given time t; and,
d. detecting that there is movement of the at least one surgical tool when the 3D spatial position of the at least one surgical tool at time $t_f$ is different from the 3D spatial position of the at least one surgical tool at time $t_0$;

e. controlling the spatial position of the at least one surgical tool within the surgical environment by means of the controller;

wherein the step of controlling is performed by storing a predetermined set of rules in a controller's database; the predetermined set of rules comprises ALLOWED and RESTRICTED movements of the at least one surgical tool, such that each detected movement by the movement detection means of the at least one surgical tool is determined as either an ALLOWED movement or as a RESTRICTED movement according to the predetermined set of rules.

It is another object of the invention to disclose the method as defined above, additionally comprising steps of selecting the predetermined set of rules from a group consisting of: most used tool, right tool rule, left tool rule, field of view rule, no fly zone rule, route rule, proximity rule; collision prevention rule, preferred volume zone rule, preferred tool rule, movement detection rule, operator input rule, environment rule, history-based rule, tool-dependent ALLOWED and RESTRICTED movements rule, tagged tool rule and any combination thereof.

It is another object of the invention to disclose the method as defined above, wherein the most used tool rule comprises a database counting the amount of movement of each of the surgical tools; the most used tool rule is adapted to constantly position the endoscope to track the movement of the most moved surgical tool.

It is another object of the invention to disclose the method as defined above, wherein the right tool rule is adapted to determine the ALLOWED movement of the endoscope according to the movement of the surgical tool positioned to right of the endoscope; further wherein the left tool rule is adapted to determine the ALLOWED movement of the endoscope according to the movement of the surgical tool positioned to left of the endoscope.

It is another object of the invention to disclose the method as defined above, wherein the field of view rule comprises n 3D spatial positions; n is an integer greater than or equal to 2; the combination of all of the n 3D spatial positions provides a predetermined field of view; the field of view rule is adapted to determine the ALLOWED movement of the endoscope within the n 3D spatial positions so as to maintain a constant field of view, such that the ALLOWED movements are movements in which the endoscope is located substantially in at least one of the n 3D spatial positions, and the RESTRICTED movements are movements in which the location of the endoscope is substantially different from the n 3D spatial positions.

It is another object of the invention to disclose the method as defined above, wherein the no fly zone rule comprises n 3D spatial positions; n is an integer greater than or equal to 2; the n 3D spatial positions define a predetermined volume within the surgical environment; the no fly zone rule is adapted to determine a RESTRICTED movement if the movement is within said no fly zone and an ALLOWED movement if the movement is outside the no fly zone, such that RESTRICTED movements are movements in which the at least one surgical tool is located substantially in at least one of the n 3D spatial positions, and ALLOWED movements are movements in which the location of the at least one surgical tool is substantially different from the n 3D spatial positions.

It is another object of the invention to disclose the method as defined above, wherein the route rule comprises a communicable database storing predefined route in which the at least one surgical tool is adapted to move within the surgical environment; the predefined route comprises n 3D spatial positions of the at least one surgical tool; n is an integer greater than or equal to 2; the ALLOWED movements are movements in which the at least one surgical tool is located substantially in at least one of the n 3D spatial positions of the predefined route, and the RESTRICTED movements are movements in which the location of the at least one surgical tool is substantially different from the n 3D spatial positions of the predefined route.

It is another object of the invention to disclose the method as defined above, wherein the proximity rule is adapted to define a predetermined distance between at least two surgical tools; ALLOWED movements are movements which are within the range or out of the range of the predetermined distance, and RESTRICTED movements which are out of the range or within the range of the predetermined distance.

It is another object of the invention to disclose the method as defined above, wherein the proximity rule is adapted to define a predetermined angle between at least three surgical tools; ALLOWED movements are movements which are within the range or out of the range of the predetermined angle, and RESTRICTED movements which are out of the range or within the range of the predetermined angle.

It is another object of the invention to disclose the method as defined above, wherein the collision prevention rule is adapted to define a predetermined distance between the at least one surgical tool and an anatomical element within the surgical environment; ALLOWED movements are movements which are in a range that is larger than the predetermined distance, and RESTRICTED movements are movements which are in a range that is smaller than the predetermined distance.

It is another object of the invention to disclose the method as defined above, wherein the anatomical element is selected from a group consisting of tissue, organ, another surgical tool and any combination thereof.

It is another object of the invention to disclose the method as defined above, wherein the preferred volume zone rule comprises a communicable database comprising n 3D spatial positions; n is an integer greater than or equal to 2; the n 3D spatial positions provides the preferred volume zone; the preferred volume zone rule is adapted to determine ALLOWED movement of the endoscope within the n 3D spatial positions and RESTRICTED movement of the endoscope outside the n 3D spatial positions, such that ALLOWED movements are movements in which the endoscope is located substantially in at least one of the n 3D spatial positions, and RESTRICTED movements are movements in which the location of the endoscope is substantially different from the n 3D spatial positions.

It is another object of the invention to disclose the method as defined above, wherein the preferred tool rule comprises a communicable database, the database stores a preferred tool; the preferred tool rule is adapted to determine ALLOWED movement of the endoscope to constantly track the movement of the preferred tool.

It is another object of the invention to disclose the method as defined above, wherein the movement detection rule comprises a communicable database comprising the real-time 3D spatial positions of each of the surgical tools; and the movement detection rule detects movement of the at least one surgical tool when a change in the 3D spatial position is received, such that the ALLOWED movements are movements in which the endoscope is directed to focus on the moving surgical tool.

It is another object of the invention to disclose the method as defined above, wherein the operator input rule comprises a communicable database; the communicable database is adapted to receive an input from the operator of the system regarding ALLOWED and RESTRICTED movements of the at least one surgical tool.

It is another object of the invention to disclose the method as defined above, wherein the input comprises n 3D spatial positions; n is an integer greater than or equal to 2; wherein at least one of which is defined as an ALLOWED location and at least one of which is defined as a RESTRICTED location, such that ALLOWED movements are movements in which the at least one surgical tool is located substantially in at least one of the n 3D spatial positions, and RESTRICTED movements are movements in which the location of the at least one surgical tool is substantially different from the n 3D spatial positions.

It is another object of the invention to disclose the method as defined above, wherein said input comprises at least one predetermined rule according to which ALLOWED and RESTRICTED movements of said at least one surgical tool are determined, such that the spatial position of said at least one surgical tool is controlled by said controller according to said ALLOWED and RESTRICTED movements.

It is another object of the invention to disclose the method as defined above, wherein said predetermined rule is selected from a group consisting of: most used tool, right tool rule, left tool rule, field of view rule, no fly zone rule, route rule, proximity rule; collision prevention rule, preferred volume zone rule, preferred tool rule, movement detection rule, operator input rule, environment rule, history-based rule, tool-dependent ALLOWED and RESTRICTED movements rule, tagged tool rule and any combination thereof.

It is another object of the invention to disclose the method as defined above, wherein said environment rule comprises a communicable database; said communicable database is adapted to received at least one real-time image of said surgical environment and is adapted to perform real-time image processing of the same and to determine the 3D spatial position of hazards or obstacles in said surgical environment; said environmental rule is adapted to determine said ALLOWED and RESTRICTED movements according to said hazards or obstacles in said surgical environment, such that said RESTRICTED movements are movements in which said at least one surgical tool is located substantially in at least one of said 3D spatial positions of said hazards or obstacles, and said ALLOWED movements are movements in which the location of said at least one surgical tool is substantially different from said 3D spatial positions of said hazards or obstacles.

It is another object of the invention to disclose the method as defined above, wherein said hazards or obstacles in said surgical environment are selected from a group consisting of tissue, a surgical tool, an organ, an endoscope and any combination thereof.

It is another object of the invention to disclose the method as defined above, wherein said history-based rule comprises a communicable database storing each 3D spatial position of each of said surgical tools, such that each movement of each surgical tool is stored; said history-based rule is adapted to determine said ALLOWED and RESTRICTED movements according to historical movements of said at least one surgical tool, such that said ALLOWED movements are movements in which said at least one surgical tool is located substantially in at least one of said 3D spatial positions, and said RESTRICTED movements are movements in which the location of said at least one surgical tool is substantially different from said n 3D spatial positions.

It is another object of the invention to disclose the method as defined above, wherein said tool-dependent allowed and RESTRICTED movements rule comprises a communicable database; said communicable database is adapted to store predetermined characteristics of at least one of said surgical tools; said tool-dependent allowed and RESTRICTED movements rule is adapted to determine said ALLOWED and RESTRICTED movements according to said predetermined characteristics of said surgical tool.

It is another object of the invention to disclose the method as defined above, wherein said predetermined characteristics of said surgical tool are selected from a group consisting of: physical dimensions, structure, weight, sharpness, and any combination thereof.

It is another object of the invention to disclose the method as defined above, wherein said tagged tool rule comprises means adapted to tag at least one surgical tool within said surgical environment and to determine said ALLOWED movement of said endoscope to constantly track the movement of said tagged surgical tool.

It is another object of the invention to disclose the method as defined above, wherein said operator input rule converts said ALLOWED movement to said RESTRICTED movement and said RESTRICTED movement to said ALLOWED movement.

It is another object of the invention to disclose the method as defined above, wherein at least one of the following is being held true (a) said system additionally comprises an endoscope; said endoscope is adapted to provide real-time image of said surgical environment; (b) at least one of said surgical tools is an endoscope adapted to provide real-time image of said surgical environment.

It is another object of the invention to disclose the method as defined above, wherein said controller's database comprises n 3D spatial positions; n is an integer greater than or equal to 2; the combination of all of said n 3D spatial positions provides a predetermined field of view; said field of view rule is adapted to relocate said endoscope if movement of at least one of said surgical tools has been detected by said detection means, such that said field of view is maintained.

It is another object of the invention to disclose the method as defined above, additionally comprising a step of alerting said physician of a RESTRICTED movement of said at least one surgical tool.

It is another object of the invention to disclose the method as defined above, wherein said step of alerting is performed by at least one selected from a group consisting of an audio signal, a voice signal, a light signal, a flashing signal and any combination thereof.

It is another object of the invention to disclose the method as defined above, wherein said ALLOWED movement is permitted by said controller and said RESTRICTED movement is denied by said controller.

It is another object of the invention to disclose the method as defined above, additionally comprising steps of providing a maneuvering subsystem communicable with said controller, said maneuvering subsystem is adapted to spatially reposition said at least one surgical tool during surgery according to said predetermined set of rules, such that if said movement of said at least one surgical tool is a RESTRICTED movement, said maneuvering subsystem prevents said movement.

It is another object of the invention to disclose the method as defined above, wherein said at least one location estimating means comprises at least one endoscope adapted to acquire real-time images of a surgical environment within said human body; and at least one surgical instrument spatial location software adapted to receive said real-time images of said surgical environment and to estimate said 3D spatial position of said at least one surgical tool.

It is another object of the invention to disclose the method as defined above, wherein said at least one location estimating means comprises (a) at least one element selected from a group consisting of optical imaging means, radio frequency transmitting and receiving means, at least one mark on said at least one surgical tool and any combination thereof; and (b) at least one surgical instrument spatial location software adapted to estimate said 3D spatial position of said at least one surgical tool by means of said element.

It is another object of the invention to disclose the method as defined above, wherein said at least one location estimating means is an interface subsystem between a surgeon and said at least one surgical tool, the interface subsystem comprising:

a. at least one array comprising N regular or pattern light sources, where N is a positive integer;
b. at least one array comprising M cameras, where M is a positive integer;
c. none or more optical markers and means for attaching said optical marker to said at least one surgical tool; and,
d. a computerized algorithm operable via the controller, said computerized algorithm adapted to record images received by each of the M cameras and to calculate therefrom the position of each of the tools, and further adapted to provide automatically the results of the calculation to the human operator of the interface.

BRIEF DESCRIPTION OF THE FIGURES

In order to understand the invention and to see how it may be implemented in practice, a few preferred embodiments will now be described, by way of non-limiting example only, with reference to be accompanying drawings, in which
FIGS. 18-21 show different configurations for the motors of a system for maneuvering an endoscope;

DETAILED DESCRIPTION OF THE INVENTION

Figure 1:
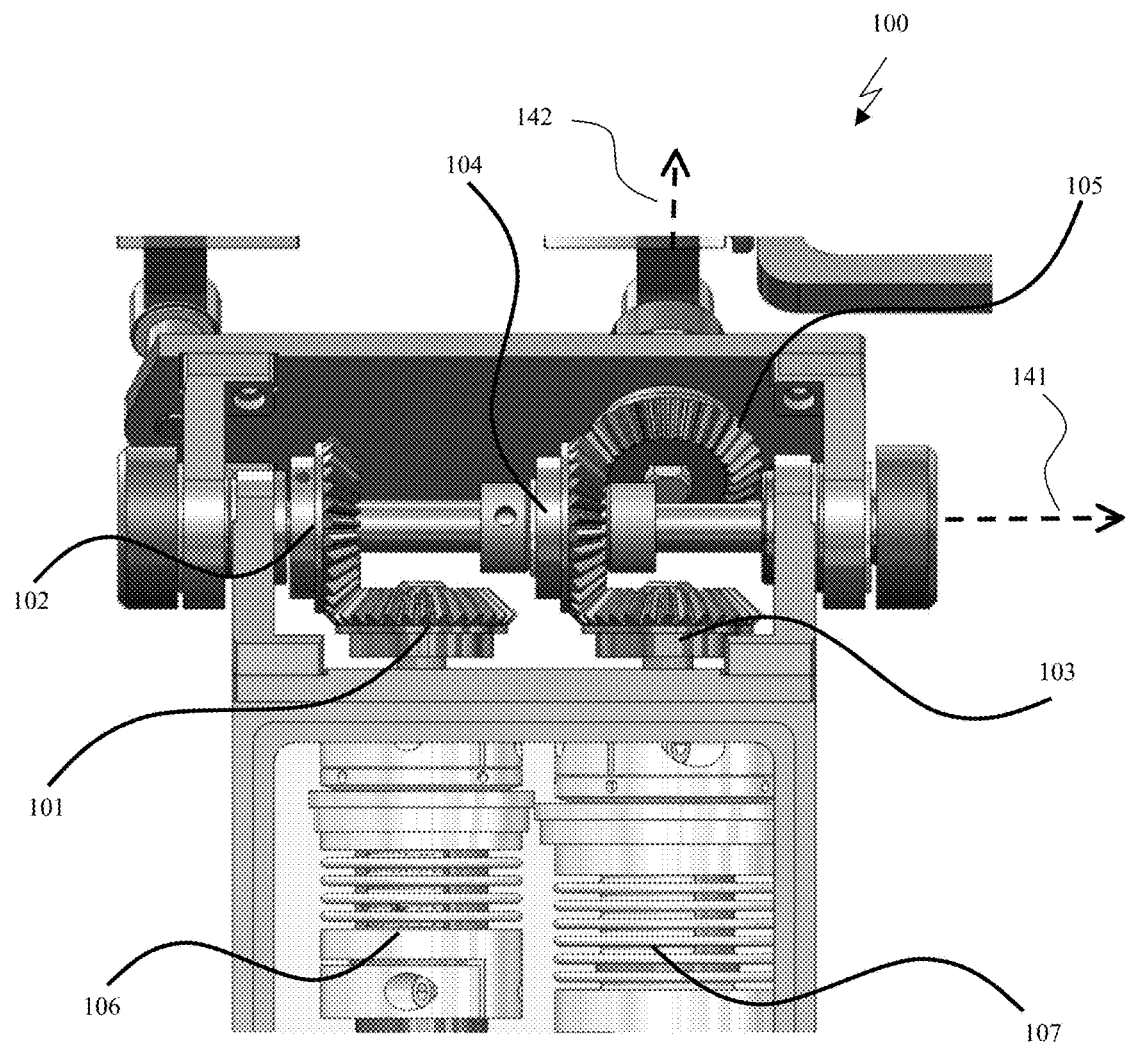
FIG. 1 presents a system for maneuvering an endoscope.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways.

Also, it is to be understood that the phraseology and terminology employed herein is for the purpose of description and should not be regarded as limiting.

A system for maneuvering an endoscope, comprising:
a. at least one first pivoting support adapted to be pivotally attached to the endoscope; the pivoting support adapted to enable the endoscope to pivot around at least one first axis of rotation;
b. at least one second pivoting support in communication with the at least one first pivoting support, the second pivoting support adapted to rotate around at least one axis being substantially orthogonal to the first axis of rotation independently of the first pivoting support; thereby enabling the endoscope to rotate around an insertion point into a body of a subject in at least two orthogonal axes;
c. at least one controller attached to either the first pivoting support or the second pivoting support, wherein the controller is adapted to provide a constant dynamic equilibrium between the endoscope and at least one of the first pivoting support or the second pivoting support.

The present invention discloses the system further comprising:
a. a first mechanism, comprising:
 i. at least one first transmission means; the first transmission means defines a first plane and is characterized by a first axis of rotation which is substantially orthogonal to the first plane;
 ii. at least one second transmission means; the second transmission means defines a second plane and second axis of rotation; the second axis of rotation is substantially orthogonal to the second plane; and the second transmission means is rotatably connected to the first transmission means; where the first plane is substantially orthogonal to the second plane; and
 iii. at least one first means adapted to rotate the first transmission means around the first axis of rotation; where the first transmission means transmits rotation to the second transmission means; and,
b. a second mechanism, comprising:
 i. at least one third transmission means which defines a third plane and is characterized by a third axis of rotation; the third axis of rotation is substantially orthogonal to the third plane;
 ii. at least one fourth transmission means which defines a fourth plane and s fourth axis of rotation; the fourth axis of rotation is substantially orthogonal to the fourth plane; and the fourth transmission means is rotatably connected to the third transmission means; where the fourth plane is substantially orthogonal to the third plane;
 iii. at least one fifth transmission means which defines a fifth plane and a fifth axis of rotation; the fifth axis of rotation is substantially orthogonal to the fifth plane; the fifth transmission means is rotatably connected to the fourth transmission means and is substantially orthogonal to the fourth plane;
 iv. at least one second means adapted to rotate the third transmission means around the third axis of rotation; where the third transmission means transmits rotation to the fourth transmission means; the fourth transmission means transmits rotation to the fifth transmission means, wherein the first mechanism and the second mechanism are adapted to rotate the endoscope around at least one second axis of rotation substantially orthogonal to the second plane; and around at least one fifth axis of rotation substantially orthogonal to the fifth plane, such that the second axis of rotation and the fifth axis of rotation are positioned at an angle A relative to each other.

The present invention additionally provides a method for maneuvering an endoscope comprising steps of:
a. providing a system comprising:
 i. a first mechanism, comprising:
  a) at least one first transmission means which defines a first plane; and is characterized by a first axis of rotation; the first axis of rotation is substantially orthogonal to the first plane;
  b) at least one second transmission means which defines a second plane and a second axis of rotation; the second axis of rotation is substantially orthogonal to the second plane; the second transmission means is rotatably connected to the first transmission means and the first plane is substantially orthogonal to the second plane; and
  c) at least one first means adapted to rotate the first transmission means around the first axis of rotation;
 ii a second mechanism, comprising:
  a) at least one third transmission means which defines a third plane; the third transmission means is characterized by a third axis of rotation; the third axis of rotation is substantially orthogonal to the third plane;
  b) at least one fourth transmission means which defines a fourth plane and a fourth axis of rotation; the fourth axis of rotation is substantially orthogonal to the fourth plane; the fourth transmission means is rotatably connected to the third transmission means such that the fourth plane is substantially orthogonal to the third plane;
  c) at least one fifth transmission means which defines a fifth plane and a fifth axis of rotation; the fifth axis of rotation is substantially orthogonal to the fifth plane; the fifth transmission means is rotatably connected to the fourth transmission means such that the fifth plane is substantially orthogonal to the fourth plane; and
  d) at least one second means adapted to rotate the third transmission means around the third axis of rotation;
b. positioning the first transmission means orthogonal to the second transmission means; where this positioning enables transmission of rotation between the first transmission means and the second transmission means;
c. positioning the third transmission means orthogonal to the fourth transmission means; where this positioning enables transmission of rotation between the third transmission means and the fourth transmission means;
d. positioning the fourth transmission means orthogonal to the fifth transmission means; where this positioning enables transmission of rotation between the fourth transmission means and the fifth transmission means;
e. coupling the second transmission means to the endoscope and the fifth transmission means to the endoscope; where the coupling enables rotation of the endoscope proportional to the rotation of the second transmission means and to the fifth transmission means; and
f. maneuvering the endoscope in at least two degrees of freedom (DOF);
wherein maneuvering in a first DOF of the at least two DOFs is performed by a step of rotating the first transmission means thereby transmitting rotation to the endoscope; wherein maneuvering in a second DOF of the at least two DOFs is performed by a step of rotating the third transmission means thereby transmitting rotation to the endoscope.

The term 'endoscope' refers hereinafter to any means adapted for looking inside the body for medical reasons. This may be any instrument used to examine the interior of a hollow organ or cavity of the body. The endoscope may also refer to any kind of a laparascope.

The term 'spatial position' refers hereinafter to a predetermined spatial location and/or orientation of an object (e.g., the spatial location of the endoscope, the angular orientation of the endoscope, and any combination thereof).

The term "degrees of freedom" (DOF) refers hereinafter to a set of independent displacements that specify completely the displaced position of the endoscope or laparoscope as defined above. In three dimensional space, there are six DOFs, three DOFs of linear displacement and three rotational DOFs, namely, moving up and down, moving left and right, moving forward and backward, tilting up and down, turning left and right, tilting side to side. According to some embodiments, the present invention refers to a system essentially comprising means for at least seven DOF selected from any of those that will be described hereinafter.

The term "about" refers hereinafter to a range of +−25% of the discussed quantity.

The term "operator" refers hereinafter to a user of the system. Examples of operators are the surgeon, the operating medical assistant, the surgeon's colleagues, etc.

The term 'automated assistant' refers hereinafter to any mechanical device (including but not limited to a robotic device) that can maneuver and control the position of a surgical or endoscopic instrument, and that can in addition be adapted to receive commands from a remote source.

The term 'provide' refers hereinafter to any process (visual, tactile, or auditory) by which an instrument, computer, controller, or any other mechanical or electronic device can report the results of a calculation or other operation to a human operator.

The term 'automatic' or 'automatically' refers to any process or action that proceeds without the necessity of direct intervention or action on the part of a human being.

The term 'manual' or 'manually' refers to any process or action necessitating direct intervention or action on the part of a human being. For a non-limiting example, an endoscope moved by a motor is under manual control when a human operator instructs the motor as to the movements of the endoscope. Such instructions can be, for example, via a movements of a joystick or via voice commands.

The term 'wholly manual' or 'wholly manually' refers to any process or action where the process or action is carried out by a human being without mechanical intervention or assistance. For example, an endoscope assistant can provide wholly manual control of an endoscope, maneuvering it directly and without mechanical assistance in response to, for example, voice commands by a physician.

The term 'motor' refers hereinafter to anything that produces or imparts motion. A motor includes, but is not limited to, an engine, an electric motor, an induction motor, a reciprocating engine, a Wankel engine, a hydraulic engine, devices employing shape memory alloys, and traction engines.

The term 'transmission means' refers hereinafter to anything that transmits movement from a motor to an object to be moved. Transmission means include, but are not limited to, gears, pulleys, gearwheels, wheels, crown gears, bevel gears, spur gears, belts, and any combination thereof.

The term 'dynamic equilibrium' refers hereinafter to maintaining the endoscope in a condition such that it the only effective torque on it is the torque deliberately applied by the system in order to rotate it. Any torques induced by the weight of the endoscope head are counterbalanced by opposing torques. Said opposing torques can be applied by springs, motors, counterweights or any other means known in the art.

The term 'counter torque' refers hereinafter to any torque applied to the endoscope and the connecting means adapted to connect the endoscope to at least one of the pivoting supports which counteracts the torques caused by the endoscope and the connecting means.

The term 'damping mechanism' refers hereinafter to any mechanism which does at least one of the following: reduces oscillatory motion of the endoscope head; and reduces acceleration of the endoscope head, especially at the beginning and the end of the motion.

The term 'passive mechanism' refers hereinafter to a mechanism which depends only on the physical properties of the mechanism itself in order to operate. A non-limiting example of a passive mechanism is a spring.

The term 'active mechanism' refers hereinafter to a mechanism which requires external input, such as, but not limited to, a source of power, input from sensors or a control mechanism in order to operate. An active mechanism can have more flexibility than a passive mechanism but can also be more prone to unwanted side-effects such as oscillation. A non-limiting example of an active mechanism is a motor.

The term 'the vertical' refers hereinafter to the direction which is parallel to the direction of the acceleration due to gravity and points away from the earth.

The term 'angle between the vertical and the endoscope' refers hereinafter to the angle between the vertical and the longitudinal axis of the endoscope. The angle is zero if the longitudinal axis of the endoscope is vertical and the angle is 90° if the longitudinal axis of the endoscope is horizontal.

The term 'tool' or 'surgical instrument' refers hereinafter to any instrument or device introducible into the human body. The term may refer to any location on the tool. For example it can refer to the tip of the same, the body of the same and any combination thereof. It should be further pointed that the following description may refer to a surgical tool/instrument as an endoscope.

The term 'region of interest' refers hereinafter to any region within the human body which may be of interest to the operator of the system of the present invention. The region of interest may be, for example, an organ to be operated on, a RESTRICTED area to which a surgical instrument is RESTRICTED to approach, a surgical instrument, or any other region within the human body.

The term 'surgical environment' refers hereinafter to any anatomical part within the human body which may be in the surroundings of a surgical instrument. The environment may comprise: organs, body parts, walls of organs, arteries, veins, nerves, a region of interest, or any other anatomical part of the human body.

The term 'prohibited area' refers hereinafter to a predetermined area to which a surgical tool (e.g., an endoscope) is prohibited to be spatially positioned in.

The term 'preferred area' refers hereinafter to predetermined area to which a surgical tool (e.g., an endoscope) is allowed and/or preferred to be spatially positioned in.

The term 'toggle' refers hereinafter to switching between one tagged surgical tool to another.

The term 'ALLOWED movement' refers hereinafter to any movement of a surgical tool which is permitted according to a predetermined set of rules.

The term 'RESTRICTED movement' refers hereinafter to any movement of a surgical tool which is forbidden according to a predetermined set of rules. For example, one rule, according to the present invention, provides a preferred volume zone rule which defines a favored zone within the surgical environment. Thus, according to the present invention an allowed movement of a surgical tool (or an endoscope) is a movement which maintains the surgical tool within the favored zone; and a RESTRICTED movement of a surgical tool (or an endoscope) is a movement which extracts (or moves) the surgical tool outside the favored zone.

The term 'time step' refers hereinafter to the working time of the system. At each time step, the system receives data from sensors and commands from operators and processes the data and commands and executes actions. The time step size is the elapsed time between time steps.

The term "about" refers hereinafter to a range of +−25% of the discussed quantity.

The following abbreviations are used throughout the disclosure:
DOF refers to degree(s) of freedom;
MOS refers to manual override system;
FTM refers to first transmission means;
STM refers to second transmission means;
TTM refers to third transmission means;
FOTM refers to fourth transmission means; and,
FTTM refers to fifth transmission means.

One of the main objects of the present invention to disclose an endoscope maneuvering device in which the working angle of the endoscope can be substantially small. Namely the physician would be able to maneuver the endoscope at angles which are tangent to the patient treated (namely about 0-30 degrees relative to the upper surface of the patient's treated organ).

Reference is now made to FIG. 1, which shows in a non-limiting manner, a first part 100 of a system for maneuvering an endoscope 200.

The system comprises a first mechanism for maneuvering an endoscope in one DOF. The first mechanism comprises: (i) At least one first transmission means (FTM) 101, where the FTM is characterized by a first axis of rotation and a first plane substantially orthogonal to the first axis of rotation. (ii) At least one second transmission means (STM) 102, where the STM is characterized by a second axis of rotation and a second plane substantially orthogonal to the second axis of rotation 141. Additionally, the STM is rotatably connected to the FTM. (iii) At least one first means 106 (especially a motor) adapted to rotate FTM 101 around a first axis of rotation. The FTM 101 transmits the rotation to the STM 102. Additionally, the system also comprises a second mechanism for maneuvering an endoscope 200 at a second DOF. The second mechanism comprises: (i) At least one third transmission means (TTM) 103, where the TTM 103 is characterized by a third axis of rotation and a third plane substantially orthogonal to the third axis of rotation. (ii) At least one fourth transmission means (FOTM) 104, where the FOTM is characterized by a fourth plane, and a fourth axis of rotation substantially orthogonal to the fourth plane, and the FOTM is rotatably connected to the TTM 103. The connection is such that the fourth plane is substantially orthogonal to the third plane. (iii) At least one fifth transmission means (FTTM) 105. The FTTM 105 defines a fifth plane and a fifth axis of rotation 142 substantially orthogonal to the fifth plane, and the FTTM 105 is rotatably connected to the FOTM 104. The connection is such that the fifth plane is substantially orthogonal to the fourth plane. (iv) At least one second means 107 (especially a motor) adapted to rotate TTM 103 around the third axis of rotation. The TTM 103 transmits rotation to FOTM 104, the FOTM 104 than transmits rotation to the FTTM 105. The system then maneuvers the endoscope 200 by adapting the first mechanism to rotate the endoscope 200 in one DOF substantially orthogonal to the second plane (i.e. second axis of rotation 141), and adapting the second mechanism to rotate the endoscope 200 in a second DOF substantially orthogonal to the fifth plane (i.e. fifth axis of rotation 142). The two DOF define two axes of rotation with angle A between them. The angle A is in the range of 0 to 180 degrees.

In some embodiments, at least some of the FTM, STM, TTM, FOTM and FTTM are coaxial, so that at least two transmission means share the same axis of rotation. A non-limiting example of coaxial transmission means would be transmission means linked by a universal joint, where the two transmission means transmit rotations in two perpendicular directions.

In other embodiments, at least one of the FTM, STM, TTM, FOTM and FTTM comprises a plurality of coaxial transmission means.

In the best embodiment, both the first means 106 and the second means 107 are static, in that both are mounted in fixed positions. The system has been designed so that the transmission means, especially FOTM and FTTM, can be driven by said means (106 and 107) with the means 106 and 107 in fixed positions.

This reduces the number of moving parts in the system, thereby improving its reliability. It is also more difficult for the system to get out of alignment, and for the gears to jam, as the main between alignments between the FTM, STM, TTM, FOTM and FTTM are fixed at the time of manufacture and do not vary during use. It also enables the system to be more compact, as there is no need to allow space for a mechanism to move within.

In preferred embodiments of the current invention, the second plane defines in a non-limiting manner angle θ and the fifth plane defines in a non-limiting manner the angle ψ. The angle θ varies between about 0 and about 360 degrees, preferably between about 0 and about 160 degrees, when system 100 is in automatic configuration or in manual configuration. Additionally, angle w varies between about 0 and about 360 degrees, preferably between about 0 and about 140 degrees, when system 100 is in automatic configuration or in manual configuration.

Figure 2A:
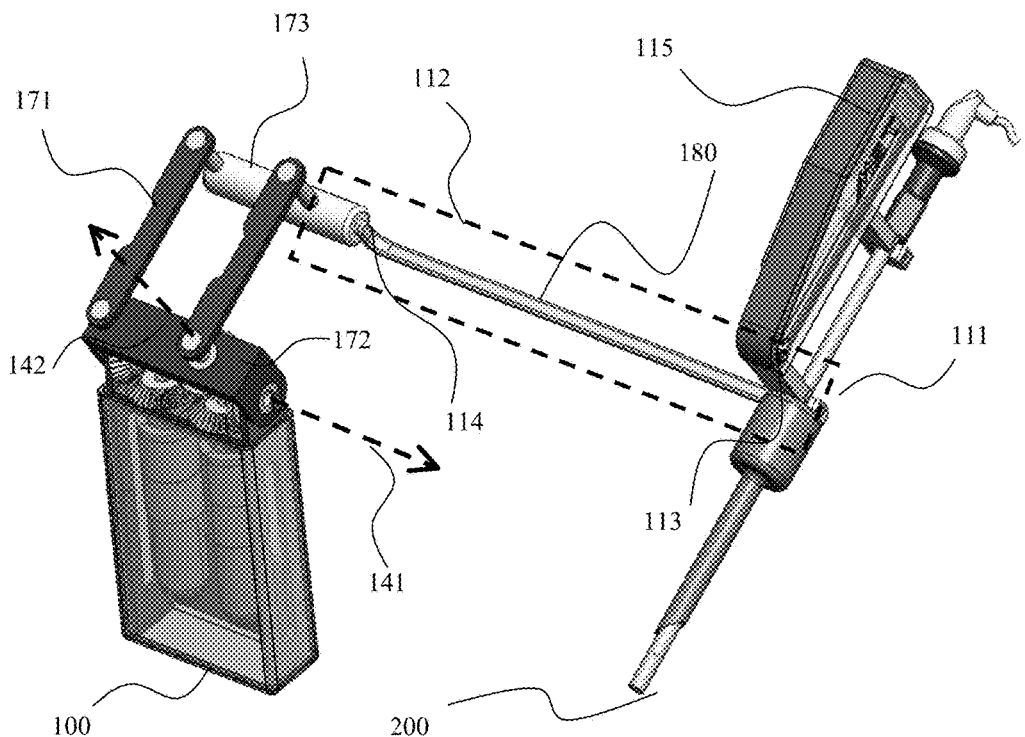
FIGS. 2a and 2b shows two configurations of the system for maneuvering an endoscope attached to a rotating means.
Figure 2B:
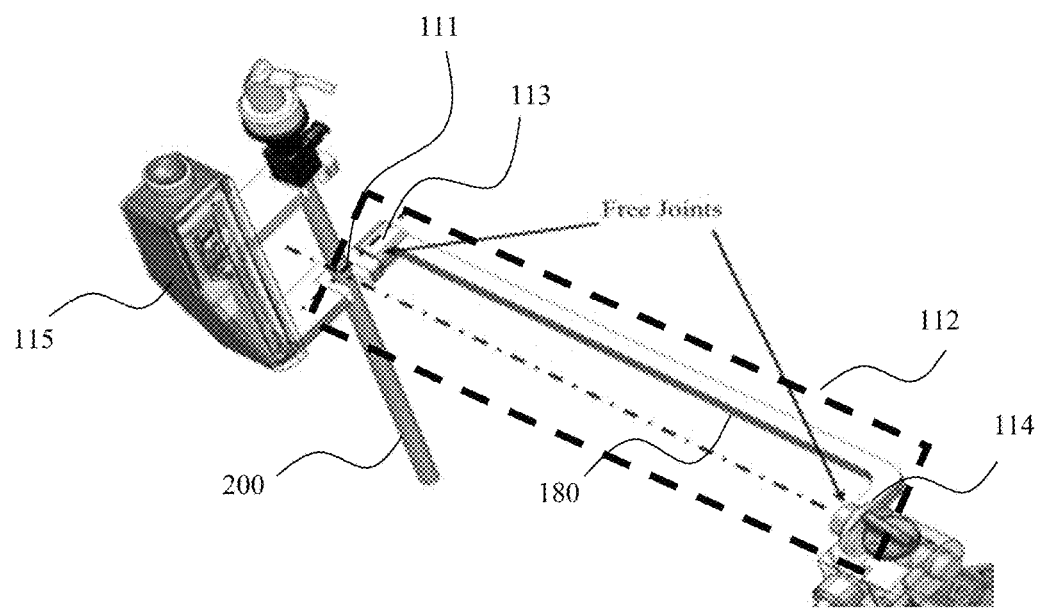

Reference is now made to FIGS. 2a and 2b, which present in a non-limiting manner a rotating means in communication with the first mechanism and the second mechanism. The rotating means comprises (i) at least one pivoting support 111 adapted to be pivotally attached to endoscope 200, pivoting support 111 is adapted to enable endoscope 200 to pivot around pivoting support 111; (ii) least one third mechanism 112 for rotating the endoscope 200 independently around two orthogonal axes; the third mechanism 112 mechanically connected to pivoting support 111, thereby enabling endoscope 200 to rotate around an insertion point in the body of a subject.

The third mechanism 112 (will also be referred to as connecting arm 612) comprising at least one pivoting support 111; and at least one second joint 114 (namely, a second pivoting support or gimbal) in communication with first pivoting support 111 and coupled to a mechanism selected from a group consisting of the first mechanism, the second mechanism and any combination thereof.

Said second pivoting support 114 is coupled to said first pivoting support 111 by means of a rod, an arm, n joints (n being an integer number greater than or equals to 1).

Each of the joints is adapted to provide rotation to pivoting support 111 in at least one of the orthogonal axes; wherein second joint 114 is located at a predetermined distance 180 from first joint 113.

In the best embodiment, gimbals or other joint mechanisms at first joint 113 and second joint 114 enable endoscope 200 to pivot about its insertion point in the body of the patient without applying force on the patient at the insertion point, especially if the line of application of force to move the endoscope is not completely collinear with the axis of the endoscope.

The pair of gimbals or other joint mechanisms at joints 113 and 114 enable sufficient flexibility that the insertion point can remain fixed without the application of force by the body of the patient.

It should be emphasized that the addition of the pair of joint mechanisms 113 and 114 ensure that no force is applied on the penetration point when the system's center of movement is misaligned with the penetration point.

It should be emphasized that according to a preferred embodiment of the present invention, joint mechanisms 113 and 114 are gimbals.

In one embodiment, each of joint mechanisms 113 and 114 has one DOF, preferably rotations about axes substantially perpendicular to each other. A non-limiting example of such a pair of rotations is shown in FIGS. 2a and 2b, where joint mechanism 114 rotates about an axis parallel to second axis of rotation 141 and joint mechanism 113 rotates about an axis of rotation perpendicular to this and parallel to the base of zoom mechanism 115. However, this embodiment is less preferred because of the possibility of pressure on the penetration point in a direction perpendicular to the third axis of rotation.

In preferred embodiments, one of joint mechanism 113 and joint mechanism 114 is enabled to rotate about two substantially perpendicular axes of rotation, while the other joint mechanism rotates about a third axis of rotation, substantially perpendicular to both of the other axes of rotation. In some variants, joint mechanism 113 can rotate about two substantially perpendicular axes of rotation, while joint mechanism 114 rotates about the third axis of rotation, substantially perpendicular to the other two, thereby enabling rotation of the endoscope about all three axes of rotation and preventing pressure on the penetration point. In other variants, joint mechanism 114 can rotate about two perpendicular axes of rotation, while joint mechanism 113 rotates about the third axis of rotation, substantially perpendicular to the other two, thereby enabling rotation of the endoscope about all three axes of rotation and preventing pressure on the penetration point. It should be further emphasized that while moving (rotating) the first mechanism (which comprises the first transmission means 101 and the second transmission means 102), the second mechanism (which comprises the third transmission means 103, the fourth transmission means 104 and the fifth transmission means 105) is moved (rotated) in the opposite direction and vice versa. Such reverse movement is highly important to compensate any unwanted/parasitic movement that would be created when moving only one mechanism.

Zoom mechanism 115 is connected to endoscope 111.

Reference is now made again to FIG. 2a which demonstrates in a non-limiting manner another object of the present invention.

In this figure a mechanism with sides forming a parallelogram for transforming the rotational movement to the endoscope is presented. As can be seen in the figure the parallelogram comprises rods 171 and 172. Rod 172 is adapted to transform rotation around the second axis of rotation 141 to the endoscope and two rods 171 are adapted to transform rotation around fifth axis of rotation 142, wherein the two rods 171 are connected to rod 172.

Rods 171, 172 and 173 form a parallelogram.

Figure 3A:
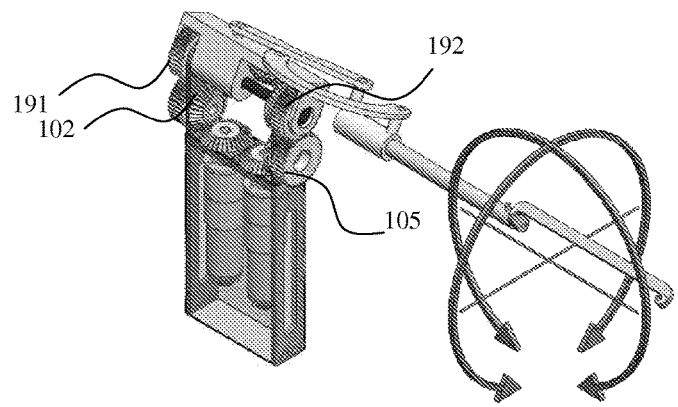
FIGS. 3a-c, 4a-b and 5a-b demonstrate more configurations of a system for maneuvering an endoscope.
Figure 3B:
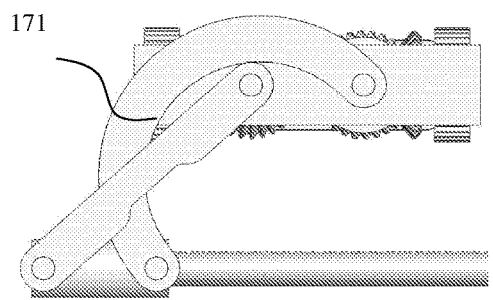
Figure 3C:
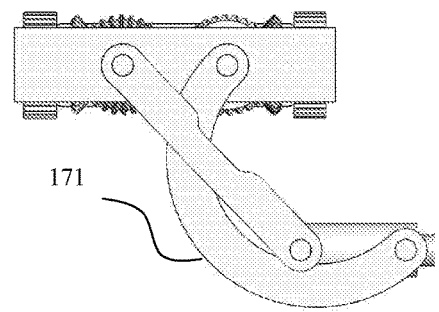

Reference is now made to FIGS. 3a, 3b and 3c, which illustrate in a non-limiting manner a parallelogram adapted to communicate between the different transmission means and the endoscope.

In the figures, the above mentioned parallelogram is characterized by having at least one non-straight rib. As can be seen, at least one rib is shaped as an arced rod.

It is within the core concept of the present invention to provide an arc shaped parallelogram, namely one characterized by at least one arc-shaped side. According to one embodiment of the present invention, the arc shaped parallelogram provides the endoscope with a wide range of angular movements and maneuverability when compared to a parallelogram with all sides straight, a non-arc shaped parallelogram.

In addition, FIG. 3a describes two additional (and 'intermediate') means 191, 192 constructed upon second transmission means 102 and fifth transmission means.

It is within the core concept of the present invention to provide the first and second mechanisms having at least one first transmission 101 (but there could be several interconnected transmissions); at least one second transmission 102 (but there could be several communicating transmissions); at least one third transmission 103 (but there could be several communicating transmissions); at least one second fourth transmission 104 (but there could be several communicating transmissions); at least one fifth transmission 105 (but there could be several communicating transmissions) and any combination thereof.

Figure 4A:
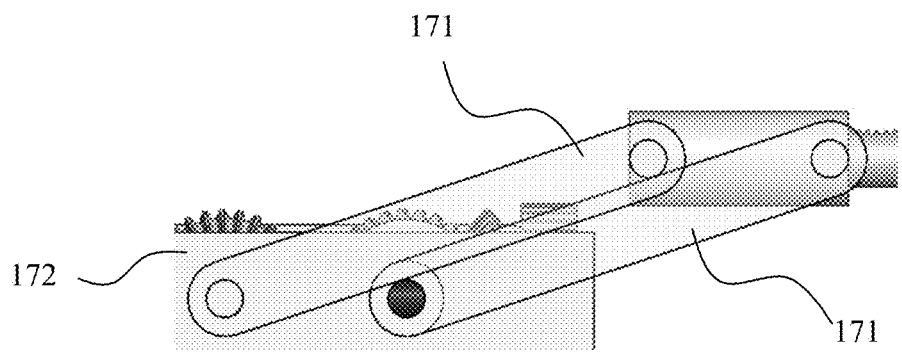
Figure 4B:
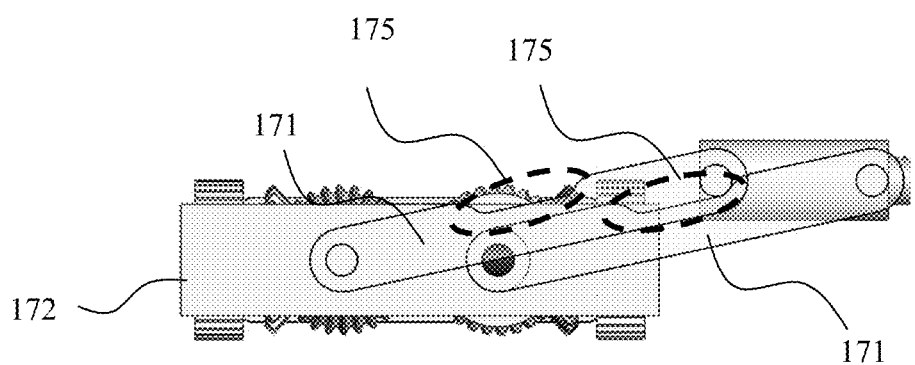

Reference is now made to FIGS. 4a, and 4b, which illustrate in a non-limiting manner another embodiment of the parallelogram described above. The figures illustrate an embodiment in which ribs 171 comprise a dent (i.e., groove) 175 and an embodiment in which ribs 171 are not provided with dent 175.

FIG. 4a demonstrates the failure of rods 171 to achieve a maximum 180 degrees angle with respect to rod 172. Such a failure is the result of the collision of ribs 171 with each other.

In FIG. 4b a solution is suggested in a form of a dent 175 in rods 171 which enables a larger angular movement of ribs 171. By providing the dent (i.e., groove) 175, a further angular movement is achieved.

Figure 5A:
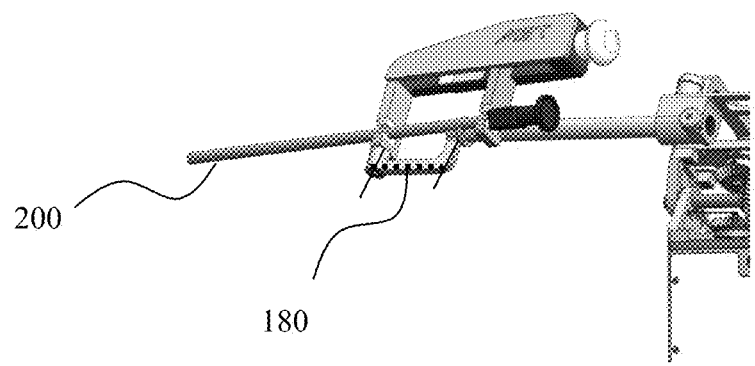
Figure 5B:
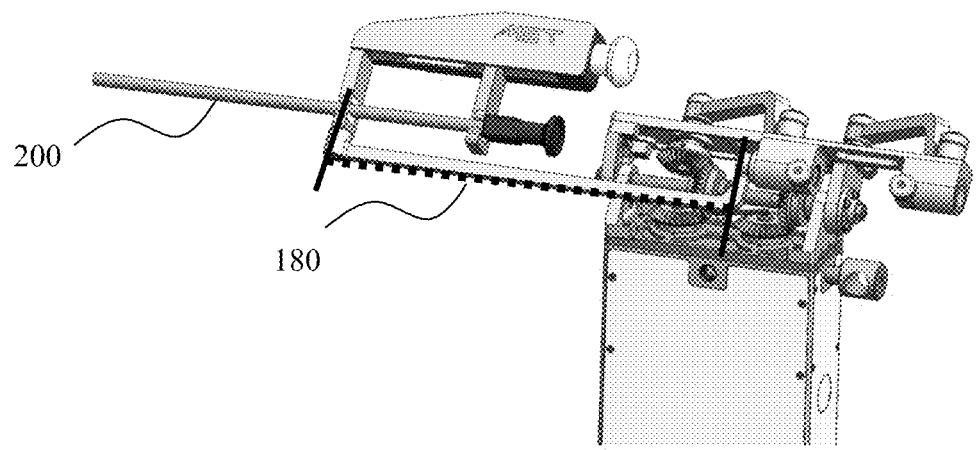

Reference is now made to FIGS. 5a and 5b, which illustrate in a non-limiting manner the predetermined distance 180 at 2 different lengths.

FIG. 5a illustrates a relatively small predetermined distance 180, such that the same limits the range of motion of the endoscope 200; FIG. 5b illustrates a larger predetermined distance 180, such that the same enables the full range of motion of the endoscope 200.

In other embodiments of the present invention, system 100 is characterized in a non-limiting manner by at least two configurations: an automatic configuration, in which system 100 is motorized; and a manual configuration in which system 100 is maneuvered manually by an endoscope user via a manual control mechanism, preferably a joystick. The system can also be characterized by a third configuration, a wholly manual configuration, in which a human endoscope assistant maneuvers the endoscope without mechanical assistance.

In other embodiments of the present invention, system 100 additionally comprises in a non-limiting manner a rotating means as described in FIG. 2 without a pivoting support such as 111.

Figure 6:
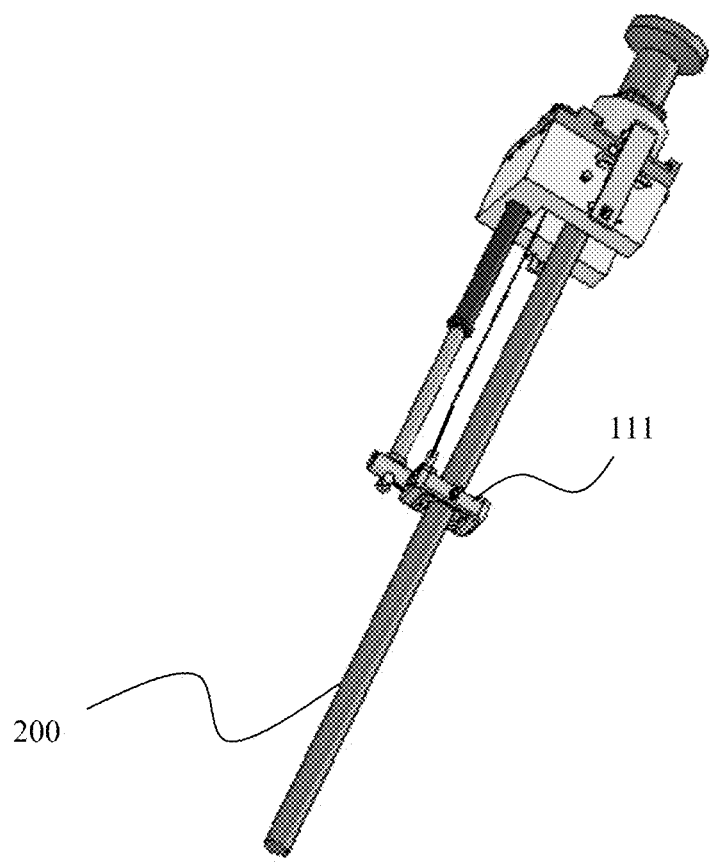
FIG. 6 presents an endoscope attached to a pivoting support.

Reference is now made to FIG. 6 which illustrates, in a non-limiting manner, pivoting support 111 as a gimbal coupled to endoscope 200.

As described above, according to one embodiment, the zoom mechanism 115 (which enables the endoscope 200 to zoom along its main longitudinal axis) can be coupled to the pivoting support 111 (see for example FIGS. 2a-2b).

Figures 7A, 7B:
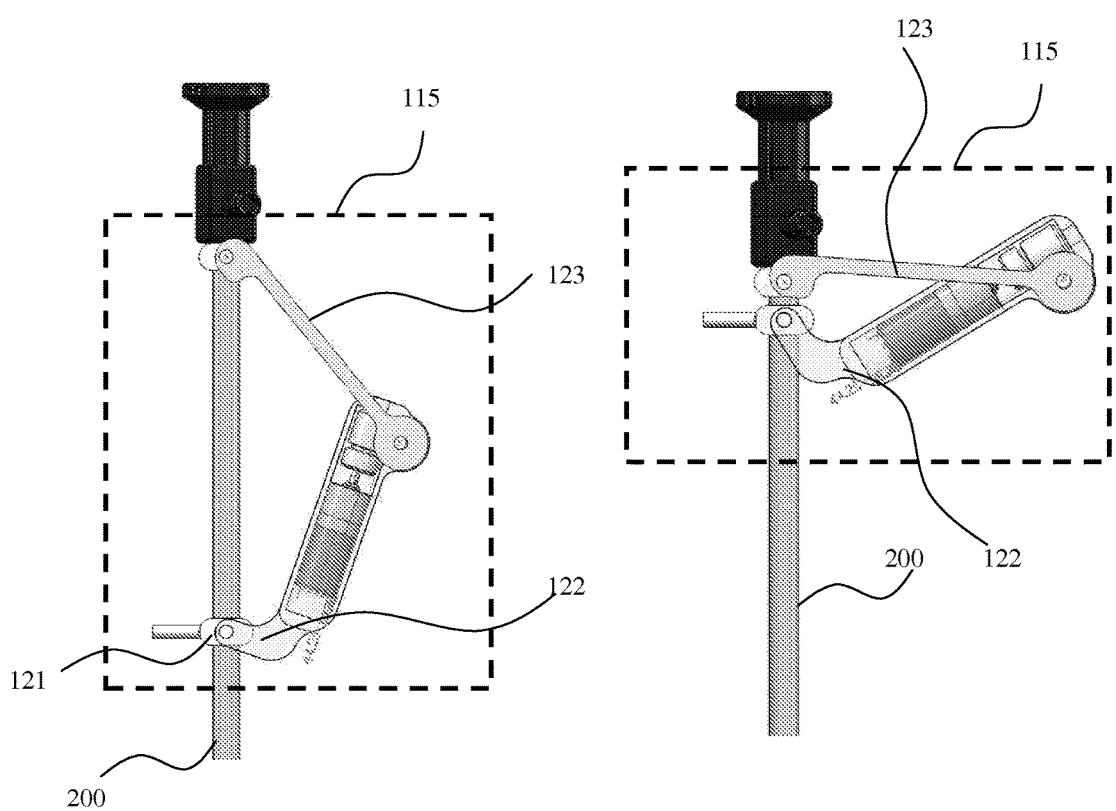
FIGS. 7a and 7b depict a zoom mechanism in two configurations.

Reference is now made to FIG. 7a which illustrates a closer view of the zoom mechanism 115. according to this embodiment, the zoom mechanism 115 comprises (i) at least one first coupling means 121 clasped to endoscope 200; (ii) at least one first connecting means 122 reversibly coupled to endoscope 200 at a first coupling position; (iii) at least one second connecting means 123 reversibly coupled to first coupling means 122 at a second coupling position. Coupling between first connecting means 122, second connecting means 123 and endoscope 200 enables the first 122 and second 123 connecting means to (i) pivot around the main longitudinal axis of the endoscope 200; and, (ii) move along the longitudinal axis of the endoscope 200.

Reference is now made to FIGS. 7a-7b which illustrate, in a non-limiting manner, the zoom mechanism 115 as described above in two different positions of the first 122 and second 123 connecting means.

In some embodiments of the current invention, first connecting means 122 and second connecting means 123 are connected to one another via a joint.

In some embodiments of the current invention, zoom mechanism 115 comprises clasping means adapted to enable reversible reciprocating movement along the main longitudinal axis of endoscope 200.

In other embodiments of the current invention, zoom mechanism 115 further comprises, in a non-limiting manner, m coupling means adapted to couple first connecting means 122 to second connecting means 123; where m is an integer greater than or equal to one.

In some embodiments of the current invention, m coupling means are rotatably coupled to each other.

In some embodiments of the current invention, coupling means are selected in a non-limiting manner from a group consisting, for example, of joints, rods, other zoom mechanisms and any combination thereof.

In other embodiments of the current invention, coupling of first connecting means 122 or second connecting means 123 to endoscope 200 is obtained by means selected in a non-limiting manner from a group consisting, for example, of mechanical means, magnetic means and any combination thereof.

In some embodiments of the current invention, the mechanical means are selected in a non-limiting manner from a group consisting, for example, of a clip, a fastening element, tape, adhesive tape, a snap fastener, a button and any combination thereof.

In some embodiments of the current invention, the magnetic means comprises in a non-limiting manner at least one magnet and at least one ferromagnet or at least one paramagnet.

According to some embodiments of the present invention, the zoom mechanism may be operated manually or automatically.

According to some embodiments of the present invention, the zoom mechanism may be operated by means of at least one motor. Such an embodiment is illustrated in FIG. 8. As can be seen from the figure, the zoom mechanism 115 is operable by motor 121.

We will now refer to the third mechanism 112. According to some embodiments of the current invention, the third mechanism 112 additionally comprises in a non-limiting manner a plurality of second joints 114, wherein each of the second joints 114 in each of third mechanisms 112 is located at a substantially different distance from first joint 113.

In other embodiments of the current invention, third mechanism 112 additionally comprises in a non-limiting manner a plurality of q joints, at least one of which is coupled to pivoting support 111 and at least one of which is coupled to the second mechanism, where q is an integer greater than or equal to one.

In some embodiments of the current invention, third mechanism 112 without the gimbal also additionally comprises in a non-limiting manner a plurality of q joints, at least one of which is coupled to pivoting support 111 and at least one of which is coupled to the second mechanism, where q is an integer greater than or equal to one.

In some embodiments of the current invention, FTM 101, STM 102, TTM 103, FOTM 104 and FTTM 105 are selected in a non-limiting manner from a group consisting, for example, of gearwheels, wheels, crown gears, bevel gears, spur gears, belts, and any combination thereof.

In some embodiments of the current invention, the second plane defines in a non-limiting manner angle $\theta$ and the fifth plane defines in a non-limiting manner the angle $\psi$. The angle $\theta$ varies between about 0 and about 360 degrees, preferably between about 0 and about 160 degrees, when system 100 is in automatic configuration or in manual configuration. Additionally, angle w varies between about 0 and about 360 degrees, preferably between about 0 and about 140 degrees, when system 100 is in automatic configuration or in manual configuration.

Figure 8A:
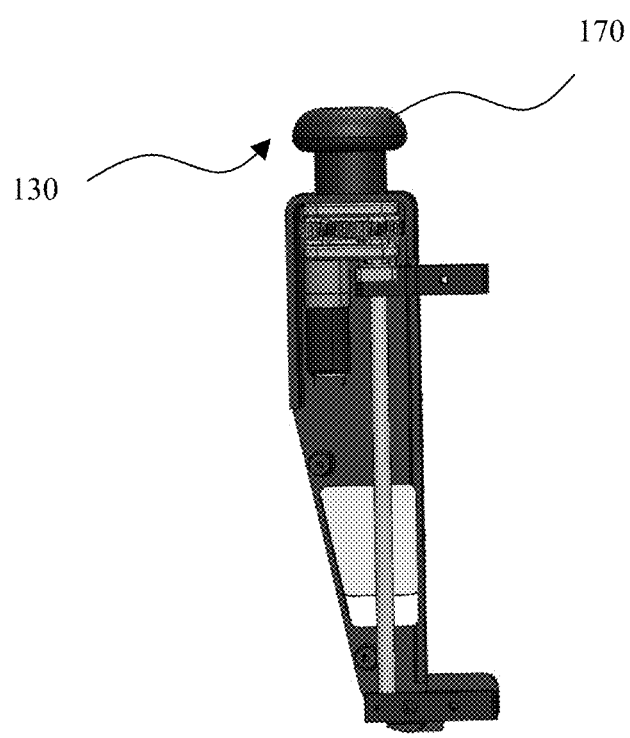
FIGS. 8a-8b present the MOS system 130.
Figure 8B:
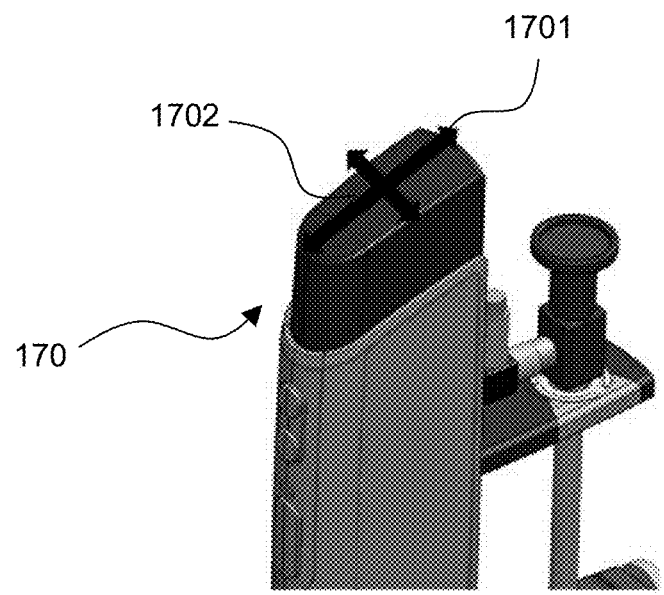

Reference is now made to FIGS. 8a-8b, which present the manual override system (MOS) 130, which is adapted, upon activation, to switch reversibly between manual configuration of the system and automatic configuration of the system. In some embodiments, the MOS has a third setting, which enables the operator to switch reversibly between automatic, manual and wholly manual operation.

MOS 130 comprises an activation means and a joystick 170 coupled to endoscope 200, used to manually maneuver endoscope 200 in any direction defined by either one of $\psi$ and $\theta$ as defined above and any combination thereof.

In the manual configuration the physician maneuvers the endoscope (and controls the movement of the same) by means of joystick 170. According to one embodiment of the present invention, the movement of the joystick is translated into movement of the endoscope.

FIG. 8b illustrates a closer view of joystick 170. Upon pressing on the joystick 170 in the directions of arrow 1701, the endoscope moves forward or backward. Upon pressing on the joystick 170 in the directions of arrow 1702 the endoscope moves left or right.

The transformation of system form the automatic configuration to the manual configuration, or to the wholly manual means, is obtained by the activation means.

Figure 9A:
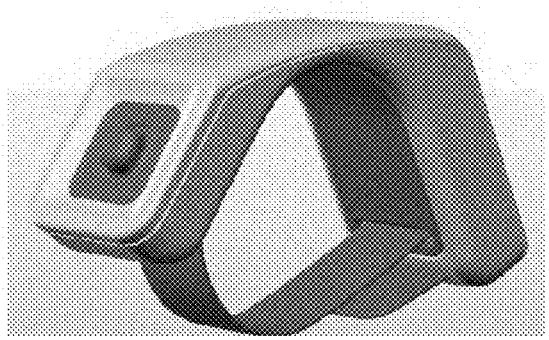
FIGS. 9a and 9b present wearable manual override systems.
Figure 9B:
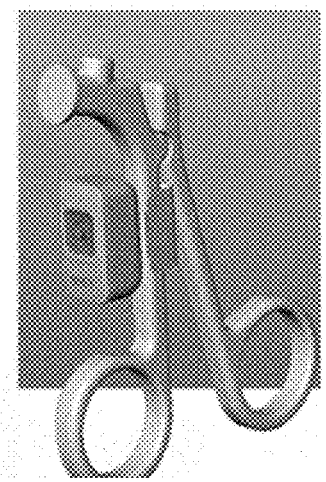

According to some embodiments of the present invention, the MOS 130 may be wearable by the user. Reference is now made to FIGS. 9a and 9b, which depict, in a non-limiting manner, activation means wearable by a user.

In other embodiments of the current invention, any one of MOS 130, joystick 170 and activation means are wearable by user.

In some embodiments of the current invention, the activation means are selected in a non-limiting manner from a group consisting, for example, of a pressing button, a rotatable knob, a knob, and any combination thereof.

In some embodiments of the current invention, MOS 130 additionally comprises in a non-limiting manner means for controlling movement of endoscope 200, adapted to restrain angular velocity in the $\theta$ and $\psi$ directions.

In some embodiments of the current invention, MOS 130 additionally comprises in a non-limiting manner n sensors, where n is an integer greater than or equal to one. Sensors are selected in a non-limiting manner from a group consisting, for example, of motion sensors, heat sensors, electric sensors, sound sensors, pressure sensors, optical sensors and any combination thereof. Sensors are adapted to activate in case of power failure or when connected to power.

In some embodiments of the current invention, joystick 170 is characterized in a non-limiting manner by an external surface.

In some embodiments of the current invention, motion sensors detect motion of joystick 170. Furthermore, motion detection of joystick 170 is used for deactivation of motion of endoscope 200 if the motion's speed is above a predetermined threshold.

In some embodiments of the current invention, motion sensors detect in a non-limiting manner motion upon the external surface of the joystick. Furthermore, motion upon the joystick's external surface is used to operate endoscope 200 in accordance with the motion. Additionally, detection of motion along the joystick is used for deactivation of the motion of endoscope 200 if the speed of the motion along the joystick is above a predetermined threshold.

In some embodiments of the current invention, heat sensors are adapted in a non-limiting manner to sense temperatures in the range of about 35 to about 42 degrees. Said heat sensors are adapted to sense whether a human hand/fingers are activating (i.e., touching) the joystick.

Furthermore, heat sensors enable in a non-limiting manner the activation of MOS 130 when the heat sensors sense temperature is in the range of about 35 to about 42 degrees.

Additionally, heat sensors are adapted in a non-limiting manner to provide a thermal image, where heat sensors are coupled to a processing unit adapted to provide the endoscope user with a thermal image, and the processing unit enables the activation of MOS 130 upon analysis of the image and detection of human hand.

In some embodiments of the current invention, electric sensors are adapted in a non-limiting manner to detect, for example, any of power failure, the electrical conductivity of a human body and any combination thereof. Additionally, human body conductivity sensed by electric sensors enables the activation of the MOS.

In some embodiments of the current invention, sound sensors are adapted in a non-limiting manner to sense predetermined sound patterns. Furthermore, predetermined sound patterns sensed by sound sensors enable the activation of the MOS 130. Additionally, sound sensors are used to operate endoscope 200 according to predetermined sound patterns (e.g., human voice, predetermined movement commands).

In some embodiments of the current invention, pressure sensors are adapted in a non-limiting manner to sense pressure applied to MOS 130.

Additionally, when pressure sensed by the pressure sensors is above a predetermined threshold, MOS 130 is either activated or de-activated, and, when the pressure sensed by pressure sensors is below a predetermined threshold, MOS 130 is either activated or de-activated.

In some embodiments of the current invention, optical sensors are adapted in a non-limiting manner to sense visual changes according to predetermined visual patterns. Furthermore, optical sensors enable the activation of MOS 130 according to predetermined visual patterns.

Additionally, optical sensors are used to operate endoscope 200 according to predetermined visual patterns.

Figure 10:
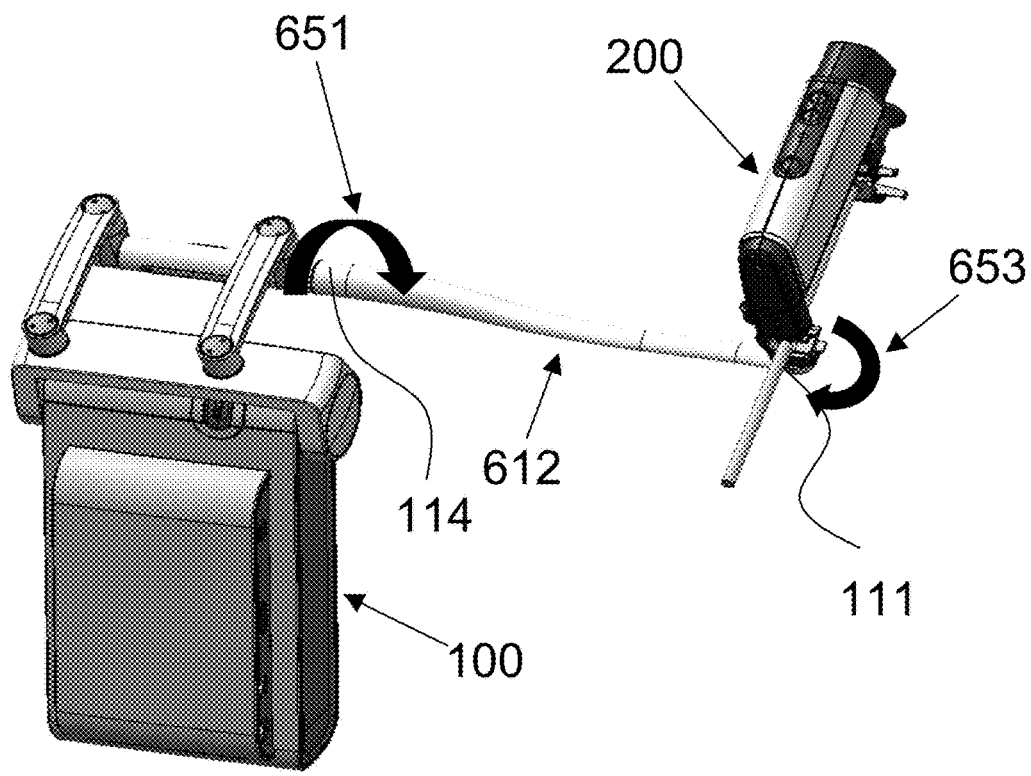
FIG. 10 presents the axes of rotation for rotation of the endoscope about the joints.

In reference to FIG. 10, an embodiment of the endoscope is shown where the third mechanism connecting the laparoscopic unit (200) to the control unit (100) is a connecting arm (612). Joint 113 connecting the endoscope, here a laparoscopic unit (200), to the connecting arm (612) allows a first passive DOF (653) and joint 114 (e.g., gimbal) connecting the control unit (100) to the connecting arm (612) allows a second passive DOF. These passive DOF reduce the forces applied by the laparoscopic unit on the penetration point.

It should be pointed that according to this embodiment, joint (or gimbal) 114 allows the connecting arm 612 (and thus, endoscope 200) to rotate around said arm's 612 main longitudinal axis.

Figure 11:
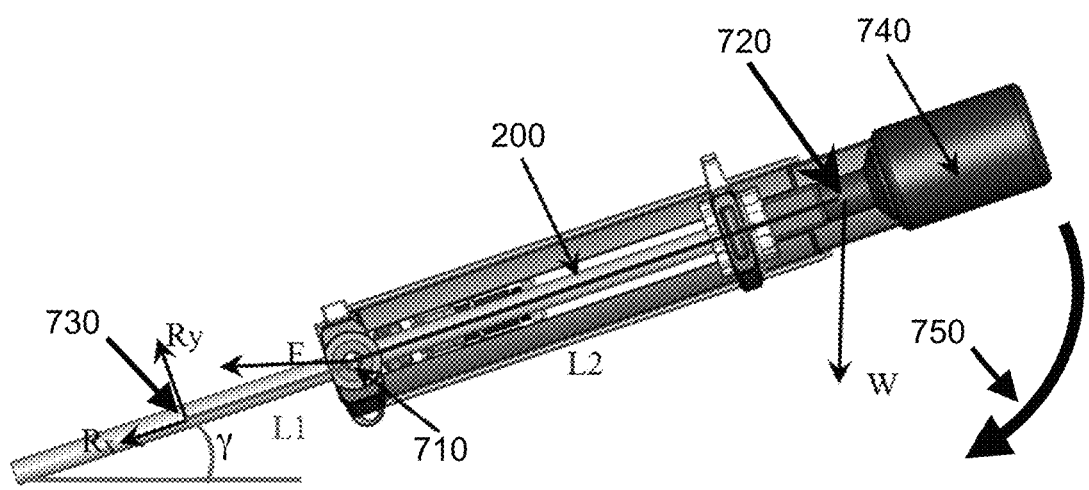
FIG. 11 illustrates the forces and torques on an endoscope attached to a pivoting support.

In reference to FIG. 11, a method of calculating the force on the penetration point is shown. An embodiment of the endoscope (200) is shown, comprising a laparoscopic unit, a laparoscopic camera unit (740) and a light cable (not shown). The laparoscopic unit (200) comprises a zoom mechanism (not shown) and is attached to the connecting arm (612) via joint 114, (not shown) at gimbal point 710. The penetration point (730) is also shown.

The weight of the endoscope 200 is W. Weight W, applied through the center of gravity of the unit (720), will tend to rotate the endoscope 200 about pivot point 710 in the direction of arrow 750, with the magnitude of the torque being $$\tau_w = L_2 \times W = L_2 W \cos \alpha,$$

where $\alpha$ is the angle between the axis of the endoscope and the vertical. This will cause a counter-torque on the penetration point 730

$$\tau_P = L_1 \times R = L_1 R_y$$

When the system is in equilibrium, $\tau_W = \tau_P$, so that $$R_y = L_2 W \cos \alpha / L_1 \qquad (1)$$

It should be noted that, in the above calculation, it is assumed that the force F applied by the control unit to the penetration point is small and has been neglected in these calculations.

As a non-limiting example, a typical laparoscopic unit has a weight of about 700 gm, while the laparoscopic camera unit, including its cable, weighs about 650 gm, for a total weight W of about 1350 gm. The distance L1 between the penetration point 730 and the pivoting point 710 is about 5 cm. The angle $\alpha$ varies between about 0 and about 90°, while $L_2$, the distance between the center of gravity 720 and the pivot point 710 varies between about 8 and about 13 cm.

Figure 12:
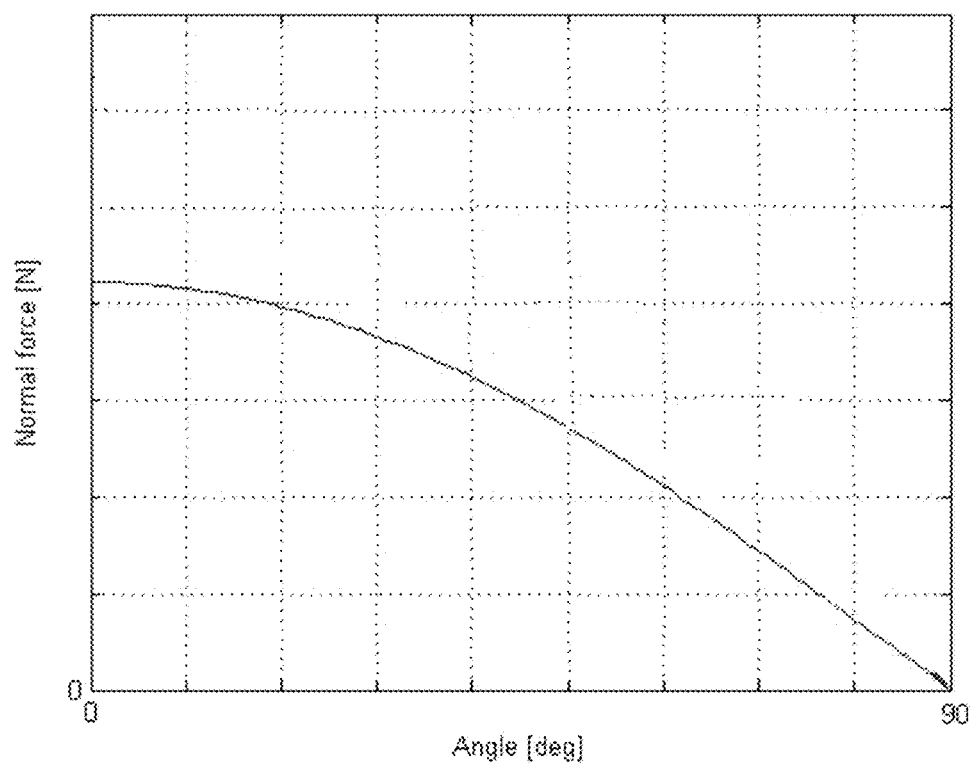
FIG. 12 schematically illustrates the normal force on the penetration point due to the endoscope.

In reference FIG. 12, an exemplary plot is shown of the magnitude of the normal force $R_y$ on the pentration point as a function of angle $\alpha$ for different zoom positions $L_2$. The normal force $R_y$ is a maximum for the maximal zoom out position and a vertical endoscope (angle $\alpha=90°$). The minimal force curve occurs for maximal zoom-in ($L_2$ a minimum).

The pressure on the penetration point depends on the force on the penetration point, $R_y$, and also on the area A over which it is applied, since $P=F/A=R_y/A$.

it should be pointed that the area over which the force is applied depends on the diameter of the trocar (D) and the thickness of the skin (t). The force is applied over the lower half-cylinder of skin in contact with the trocar. The area of skin in contact with the trocar is $$A_c = (2\pi r)t$$

where $2\pi r$ is the circumference of the cylinder and t is its height. Therefore, the area over which the pressure is applied is half that, $$A = \pi rt$$

and the pressure on the penetration point is $$P = R_y/A = R_y/\pi rt \qquad (2)$$

Basically, as is expected, when the endoscope is position vertically to the ground (floor) the center of mass of the same applies the maximum force (and thus, torque).

It should be pointed that in order to maintain control over the endoscope position and to minimize the effect of differing endoscope weights and angles on the controllability of the endoscope positioning system, at least one of joint mechanisms 113 and 114 includes a mechanism adapted to modify movement of the gimbal. In preferred embodiments, this mechanism to modify movement is a controller adapted to apply a torque to the joint mechanism, the torque being a function of the angle θ, so that the endoscope 200 plus zoom mechanism 115 remains in dynamic equilibrium about at least one of axes 651 and 653. The dynamic equilibrium is such that the torque $L_2 W \cos \alpha$ is substantially equal to the torque supplied by the controller.

The controller can supply torque to the system passively or actively, or a combination thereof. A passive means of supplying torque is one that requires no external input in order to operate; the action of a passive mechanism depends only on the physical properties of the mechanism itself. A non-limiting example of a passive mechanism is a device comprising a spring or springs.

An active means of supplying torque, on the other hand, requires external input, such as, but not limited to, a source of power, input from sensors or a control mechanism in order to operate. An active mechanism can have more flexibility than a passive mechanism but can also be more prone to unwanted side-effects such as oscillation. A non-limiting example of an active mechanism comprises a motor and at least one sensor.

A non-limiting example of a combined device comprises at least one spring with at least one motor.

Figure 13A:
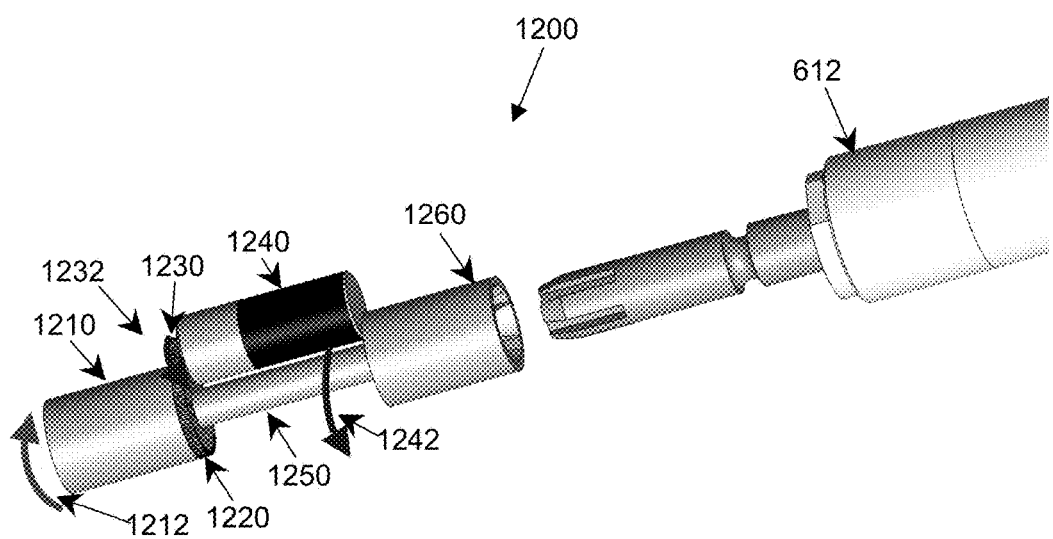
FIG. 13a-b and 14 presents a pivoting support with a controller.
Figure 13B:
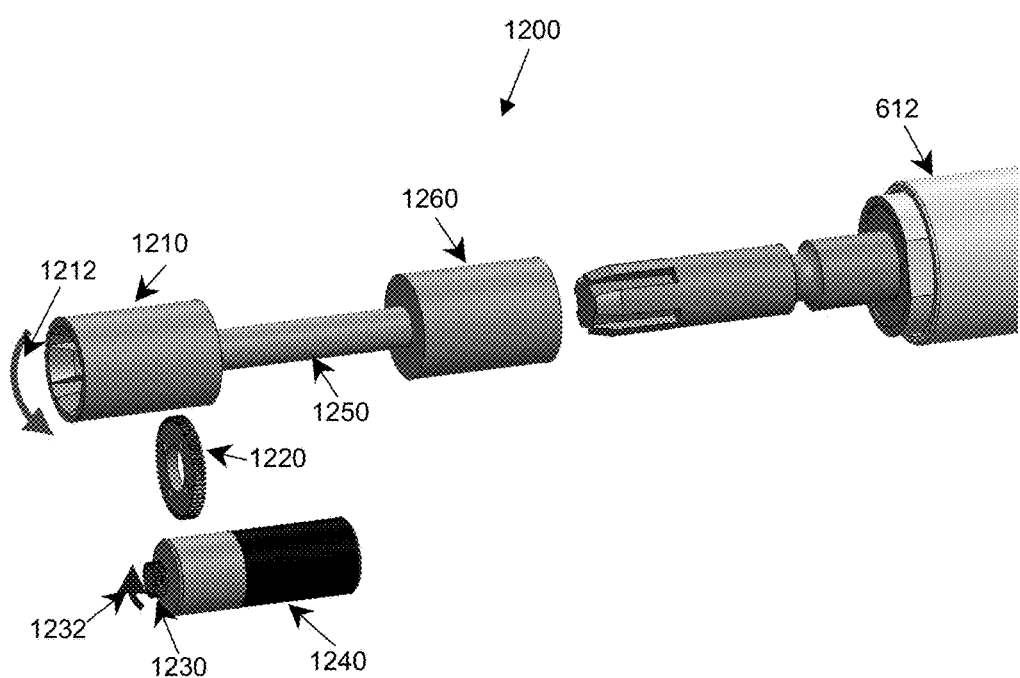

In reference to FIG. 13, an embodiment of an active controller is shown. In FIG. 13a, the controller is shown assembled and in FIG. 13b, it is shown disassembled to make more clear the connections between the parts. Similar numbers are used for similar parts in both figures. The controller is connectable via distal connector 1260 to the proximal end of connecting arm 612 (shown disengaged) and, at its proximal end, the controller is connectable via proximal connector 1210 to rods 171 (not shown) of the control unit.

Distal connector 1260 is fixed to narrow section 1250, which fixedly connected to large gear 1220. Large gear 1220 is fixedly connected to proximal connector 1210. Large gear 1220 is meshed with small gear 1230, which is fixedly connected to motor 1240. The distal end of motor 1240 rests slidably on the proximal end of distal connector 1260, while the proximal end of motor 1240 rests slidably on the distal end of proximal connector 1210, fixing motor 1240 in place.

Figure 14:
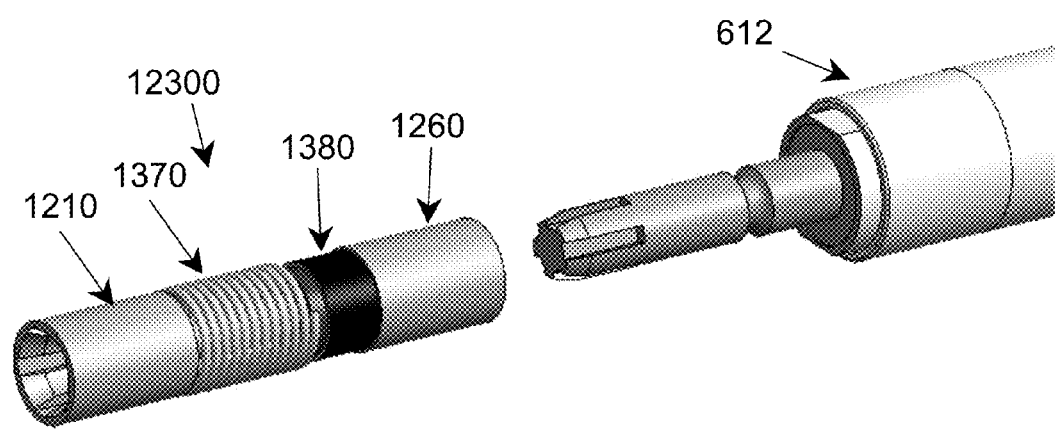

As an example of the functioning of the mechanism, if motor 1240 rotates gear 1230 counterclockwise (CCW) (arrow 1232), then the motor moves CCW around narrow section 1250 (arrow 1242) and large gear 1210 rotates clockwise (CW), causing proximal connector 1210 to rotate CW. Since the controller is substantially frictionlessly connected to arms 171, CW rotation of the connectors 1210 and 1260 causes arm 612 to rotate CW, thereby rotating the endoscope unit 200, In reference to FIG. 14, an embodiment of a passive controller 1200 is shown. In this embodiment, motor 1240 has been replaced by spring 1370 and damping mechanism 1380 and proximal connector 1210 is rotatably connected to narrow section 1250 (not seen)

Spring 1370 is fixedly connected to damping mechanism 1380 and is fixedly connected to proximal connector 1210. Damping mechanism 1380 is fixedly connected to distal connector 1260, which is removably connected to arm 612. Rotation of arm 612 CCW tightens spring 1370, thereby tending to oppose rotation of arm 612.

The damping mechanism does at least one of the following: reduces oscillatory motion of the endoscope head; and reduces acceleration of the endoscope head, especially at the beginning and the end of the motion.

In one variant, damping mechanism 1290 comprises a fluid-filled cylinder and a perforated plunger which hugs the inner walls of the fluid-filled cylinder tightly but movably, so that there is little leakage of fluid between the edges of the cylinder and the inner walls of the cylinder. The plunger can move because the fluid can flow through the perforations in it. However, because of the size of the holes and the viscosity of the fluid, the damping mechanism prevents large accelerations of the system and also damps out oscillatory motion in the system.

Figure 15:
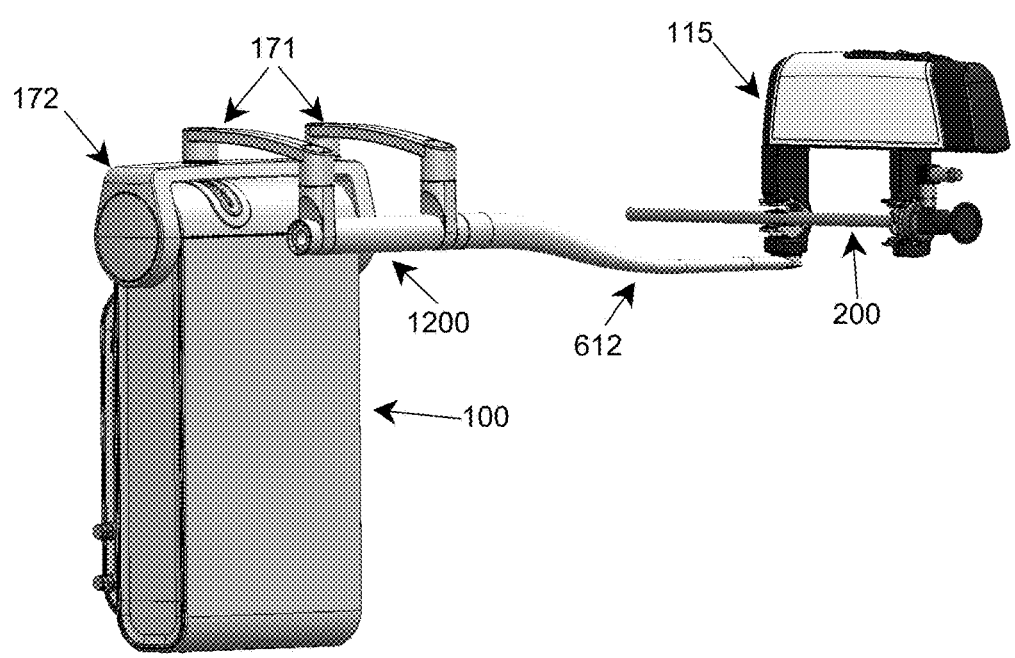
FIG. 15 presents a system for maneuvering an endoscope with pivoting supports comprising controllers.

In reference to FIG. 15, illustrating another embodiment of the system, the first part 100 of the system is connected, as disclosed above, to rods 172 and 171. Rods 171 are connected to the proximal end of connecting arm 612 via controller 1200, and the distal end of connecting arm 612 is connected to zoom mechanism 115 and endoscope 200.

Figure 16:
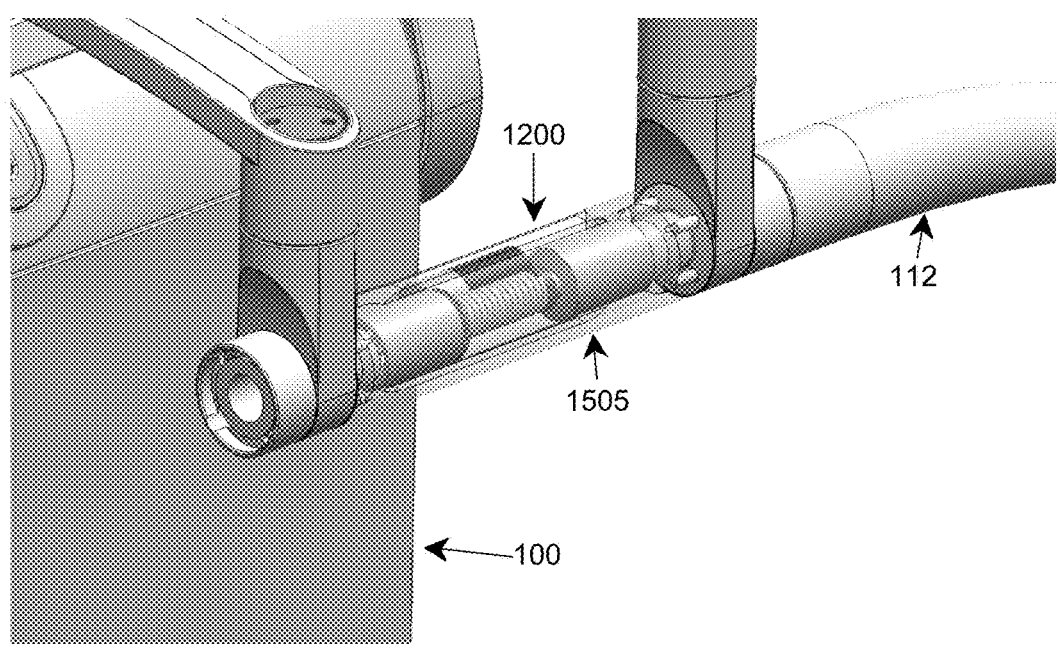
FIG. 16 presents a pivoting support and controller with transparent cover.
Figure 17:
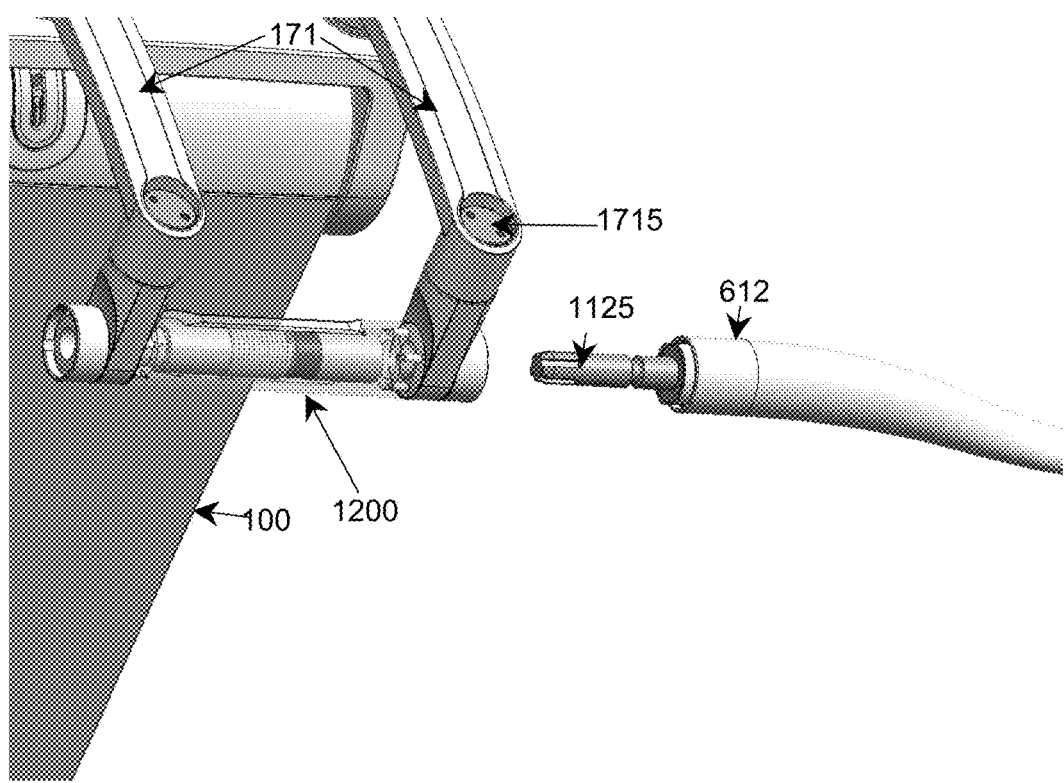
FIG. 17 presents the pivoting support, showing a connector adapted to join the pivoting supports to the connecting arm linking the pivoting supports to the endoscope.

In reference to FIG. 16, a combined device (1200) is shown, which combines the spring (1270) of the passive controller with the motor (1240) of the active controller. Also shown FIG. 16 is cover 1505, which protects the mechanism and prevents objects, such as the garments of the operating personnel, from interfering with the working of the mechanism. Cover 1505 can also be sterilizable and thereby enable the external portion of the controller to be sterile. In reference to FIG. 17, another view of the controller of FIG. 17 is shown, showing first part 100 of the system, rods 171, the proximal end of connecting arm 612, and controller 1200. The connector 1125 at the proximal end of connecting arm 612 connects to controller 1200, which passes through and is supported by rods 171. Fasteners 1715, which fix controller 1200 to rods 171, are also shown.

In some embodiment (e.g., FIG. 17) the controller is attached to pivoting support 114; in other embodiments a controller is attached to or part of pivoting support 113; in yet other embodiments, a controller is attached to or part of each of the pivoting supports 114 and 113. In preferred variants of embodiments with two controllers, the controllers are in communication with each other.

In some embodiments, the controller is activated at all times and continually affects movement of at least one of the pivoting supports.

In other embodiments, the controller is activated only if the torque induced by the weight of the endoscope head is large, for example, if the angle θ between the endoscope and the vertical is large, so that the endoscope approaches being parallel to the floor.

In yet other embodiments, the controller is activated if the torque is larger than a predetermined value, so that, for a lightweight enough endoscope, the controller will not be activated at all while, with a large and heavy endoscope, the controller will be activated for most working angles.

In preferred embodiments, the system additionally comprises an automatic assistant in communication with the endoscope which is adapted to maneuver the endoscope.

In preferred embodiments, the system additionally comprises an alignment mechanism adapted to instruct the automatic assistant to align the endoscope.

In some embodiments of the current invention, FTM 101, STM 102, TTM 103, FOTM 104 and FTTM 105 are selected in a non-limiting manner from a group consisting, for example, of gearwheels, wheels, crown gears, bevel gears, spur gears, belts, and any combination thereof.

In some embodiments of the current invention, system 100 additionally comprises in a non-limiting manner a quick release handle adapted to disassemble endoscope 200 from system 100 when system 100 is in automatic configuration or in manual configuration In some embodiments of the current invention, the first mechanism additionally comprises in a non-limiting manner locking means adapted to maintain in a predetermined orientation upon power failure at least one selected from a group consisting, for example, of: FTM 101, STM 102 and any combination thereof; and to prevent any rotational movement of the same upon power failure.

In some embodiments of the current invention, the second mechanism additionally comprises in a non-limiting manner locking means adapted to maintain in a predetermined orientation upon power failure at least one selected from a group consisting, for example, of: TTM 103, FOTM 104, FTTM 105 and any combination thereof; and to prevent any rotational movement of the same upon power failure.

MOS 130 comprises an activation means and a joystick 170 coupled to endoscope 200, used to manually maneuver endoscope 200 in any direction defined by either one of $\psi$ and $\theta$ as defined above and any combination thereof.

In the manual configuration the physician maneuvers the endoscope (and controls the movement of the same) by means of joystick 170. According to one embodiment of the present invention, the movement of the joystick is translated into movement of the endoscope.

Upon pressing on the joystick 170 in the directions of arrow 1702 the endoscope moves left or right.

The transformation of system form the automatic configuration to the manual configuration, or to the wholly manual means, is obtained by the activation means.

In some embodiments of the current invention, the activation means are selected in a non-limiting manner from a group consisting, for example, of a pressing button, a rotatable knob, a knob, and any combination thereof.

In some embodiments of the current invention, MOS 130 additionally comprises in a non-limiting manner means for controlling movement of endoscope 200, adapted to moderate angular velocity in the $\theta$ and $\psi$ directions.

In some embodiments of the current invention, MOS 130 additionally comprises in a non-limiting manner n sensors, where n is an integer greater than or equal to one. Sensors are selected in a non-limiting manner from a group consisting, for example, of motion sensors, heat sensors, electric sensors, sound sensors, pressure sensors, optical sensors and any combination thereof. Sensors are adapted to activate in case of power failure or when connected to power.

In some embodiments of the current invention, joystick 170 is characterized in a non-limiting manner by an external surface.

In some embodiments of the current invention, motion sensors detect motion of joystick 170. Furthermore, motion detection of joystick 170 is used for deactivation of motion of endoscope 200 if the motion's speed is above a predetermined threshold.

In some embodiments of the current invention, motion sensors detect in a non-limiting manner motion upon the external surface of the joystick. Furthermore, motion upon the joystick's external surface is used to operate endoscope 200 in accordance with the motion. Additionally, detection of motion along the joystick is used for deactivation of the motion of endoscope 200 if the speed of the motion along the joystick is above a predetermined threshold.

In some embodiments of the current invention, heat sensors are adapted in a non-limiting manner to sense temperatures in the range of about 35 to about 42 degrees. Said heat sensors are adapted to sense whether a human hand/fingers are activating (i.e., touching) the joystick.

Furthermore, heat sensors enable in a non-limiting manner the activation of MOS 130 when the heat sensors sense that the temperature is in the range of about 35 to about 42 degrees.

Additionally, heat sensors are adapted in a non-limiting manner to provide a thermal image, where heat sensors are coupled to a processing unit adapted to provide the endoscope user with a thermal image, and the processing unit enables the activation of MOS 130 upon analysis of the image and detection of human hand.

In some embodiments of the current invention, electric sensors are adapted in a non-limiting manner to detect, for example, any of power failure, the electrical conductivity of a human body and any combination thereof. Additionally, human body conductivity sensed by electric sensors enables the activation of the MOS.

In some embodiments of the current invention, sound sensors are adapted in a non-limiting manner to sense predetermined sound patterns. Furthermore, predetermined sound patterns sensed by sound sensors enable the activation of the MOS 130. Additionally, sound sensors are used to operate endoscope 200 according to predetermined sound patterns (e.g., human voice, predetermined movement commands).

In some embodiments of the current invention, pressure sensors are adapted in a non-limiting manner to sense pressure applied to MOS 130.

Additionally, when pressure sensed by the pressure sensors is above a predetermined threshold, MOS 130 is either activated or de-activated, and, when the pressure sensed by pressure sensors is below a predetermined threshold, MOS 130 is either activated or de-activated.

In some embodiments of the current invention, optical sensors are adapted in a non-limiting manner to sense visual changes according to predetermined visual patterns. Furthermore, optical sensors enable the activation of MOS 130 according to predetermined visual patterns. Additionally, optical sensors are used to operate endoscope 200 according to predetermined visual patterns.

Figures 18A, 18B:
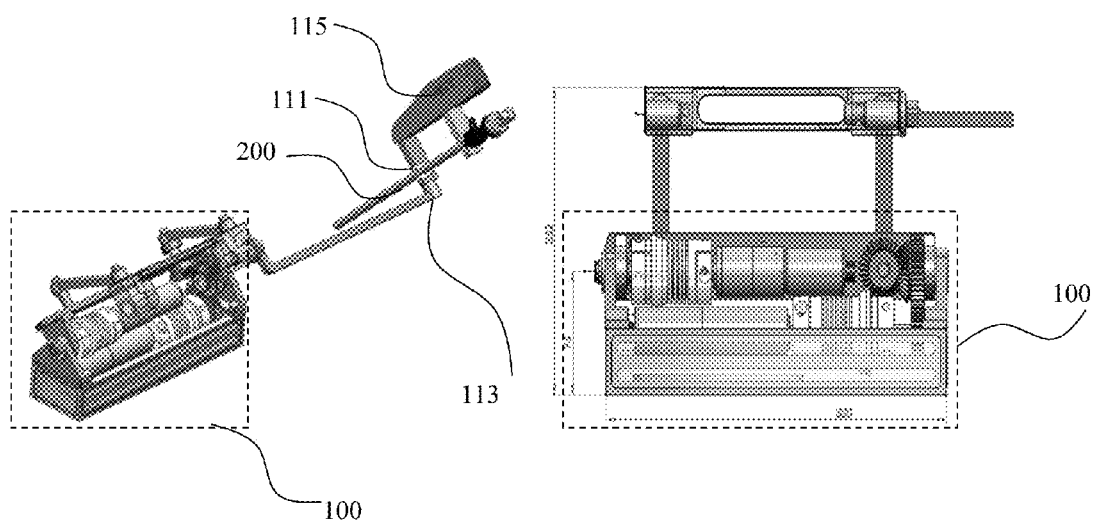

Reference is now made to FIGS. 18*a* and 18*b*, illustrating in a non-limiting manner, from different points of view, the first mechanism and the second mechanism assembled in a horizontal configuration.

Figure 19A:
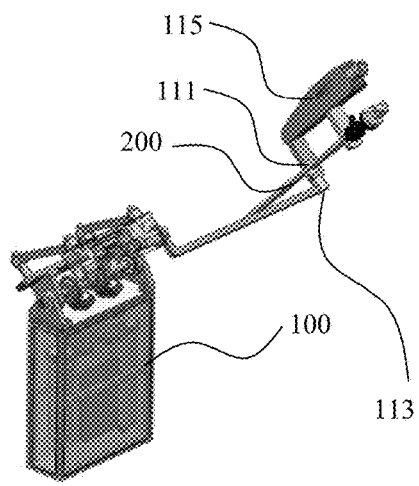
Figure 19B:
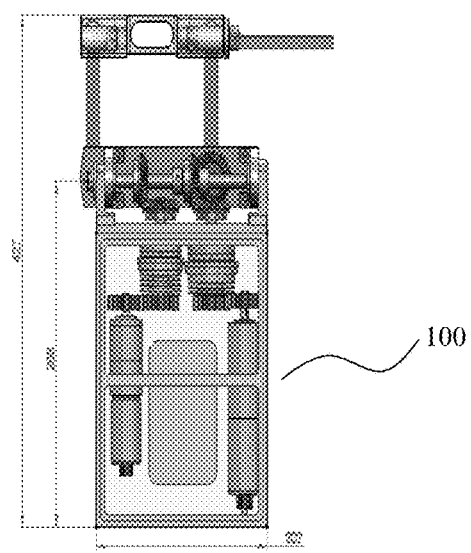

Reference is now made to FIGS. 19*a* and 19*b*, illustrating in a non-limiting manner different points of view of the first mechanism and the second mechanism assembled in a vertical configuration.

Reference is now made to FIGS. 20*a* and 20*b*, illustrating in a non-limiting manner, from different points of view, the first mechanism and the second mechanism assembled in a compact vertical configuration.

Figure 21:
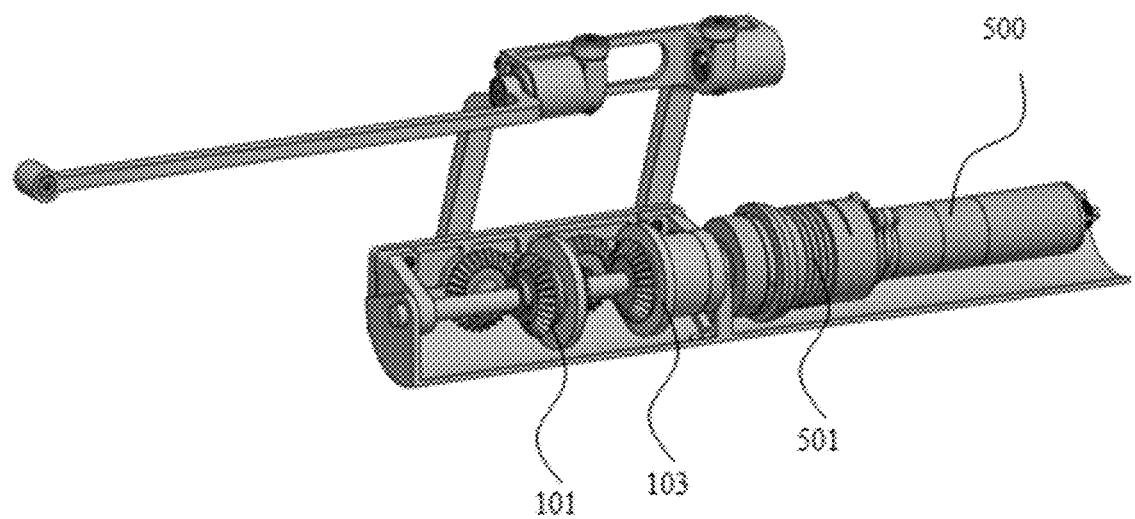

Reference is now made to FIG. 21 which depicts, in a non-limiting manner, one configuration of the first mechanism and the second mechanism, where first rotation means 106 and second rotation means 107 (shown in FIG. 1) are unified to a single rotation means 500.

Said single rotation means 500 is provided with means adapted to switch between rotating first transmission means 101 and third transmission means 103 by a clutch 501.

In some embodiments of the current invention, the endoscope is adapted in a non-limiting manner to acquire real-time images of a surgical environment within human body.

In some embodiments of the current invention, system 100 additionally comprises in a non-limiting manner a surgical tracking system (STS) for assisting an operator to perform laparoscopic surgery on a human body, the surgical tracking system comprising (i) a maneuvering subsystem adapted to control the spatial position of endoscope 200 during laparoscopic surgery; and (ii) a tracking subsystem in communication with the maneuvering subsystem, adapted to controlling the maneuvering subsystem so as to direct and modify the spatial position of endoscope 200 to a region of interest. The tracking subsystem comprises a data processor that is adapted to perform real-time image processing of the surgical environment and modify the spatial position of endoscope 200 according to a rule based approach. The rule based approach comprises a maneuvering function f(t) which is calculated according to at least two instructing functions $g_i(t)$, where i is 1, . . . , n and n≥2; where t is time.

In some embodiments of the current invention, the rule based approach of the maneuvering function f(t) is a function of $a_i(t)*g_i(t)$ i=1, . . . , n where $g_i(t)$ are the instructing functions, $a_i(t)$ are weighting functions of each $g_i(t)$, and n is the total number of instruction functions, n≥2.

In some embodiments of the current invention, each of the instructing functions $g_i(t)$ is selected in a non-limiting manner from a group consisting of: most used tool function, a right tool function, left tool function, field of view function, no fly zone function, a tool detection function, movement detection function, organ detection function, collision detection function, operator input function, prediction function, past statistical analysis function, and any combination thereof.

In some embodiments of the current invention, weighting functions $a_i(t)$ are, for example, time-varying functions, the value of which is determined by the operator or the output of the instructing functions $g_i(t)$.

In some embodiments of the current invention, the tool detection function is adapted in a non-limiting manner to detect surgical tools in the surgical environment and to classify the detected tools as prohibited areas and preferred areas. The surgical tools are selected in a non-limiting manner from a group consisting of: the tip of a surgical instrument, a grasper, a surgical instrument, a non-surgical instrument, and any combination thereof.

In some embodiments of the current invention, the tip of a surgical instrument is classified in a non-limiting manner as a preferred area and the grasper is classified as a prohibited area.

In some embodiments of the current invention, the movement detection function is adapted in a non-limiting manner to detect physiological or a non-physiological movements in the surgical environment and to classify the detected movements as prohibited areas and preferred areas.

In some embodiments of the current invention, the organ detection function is adapted in a non-limiting manner to detect physiological organs in the surgical environment and to classify the detected organs as prohibited areas and preferred areas.

In some embodiments of the current invention, the right tool function is adapted in a non-limiting manner to constantly track the movement of the right tool.

In some embodiments of the current invention, the left tool function is adapted in a non-limiting manner to constantly track the movement of the left tool.

In some embodiments of the current invention, the field of view function is adapted in a non-limiting manner to maintain a constant field of view of the endoscope.

In some embodiments of the current invention, the no fly zone function is adapted in a non-limiting manner to instruct the maneuvering subsystem to prevent movement of the endoscope into a no fly zone.

In some embodiments of the current invention, the most used tool function is adapted in a non-limiting manner to instruct the maneuvering subsystem to constantly position the endoscope to track the movement of the most moved tool.

In some embodiments of the current invention, the collision detection function is adapted in a non-limiting manner to detect prohibited areas within the surgical environment so as to prevent collisions between the endoscope and the prohibited areas.

In some embodiments of the current invention, the operator input function is adapted in a non-limiting manner to receive an input from the operator. The input is selected in a non-limiting manner from a group consisting, for example, of: an input regarding prohibited areas in the surgical environment, an input regarding allowed areas in the surgical environment, and input regarding the region of interest.

In some embodiments of the current invention, the operator input function further comprises in a non-limiting manner a selection algorithm for selection of areas, where the areas are selected in a non-limiting manner from a group consisting, for example, of: prohibited areas, allowed areas, region of interest, and any combination thereof.

In some embodiments of the current invention, image processing comprises algorithms selected in a non-limiting manner from a group consisting, for example, of: image stabilization algorithms, image improvement algorithms, image compilation algorithms, image enhancement algorithms, image detection algorithms, image classification algorithms, smoke detection algorithms, vapor detection algorithms, steam detection algorithms, algorithms to reduce steam from the endoscope and any combination thereof.

In some embodiments of the current invention, the endoscope comprises in a non-limiting manner an image acquisition device selected in a non-limiting manner from a group consisting, for example, of: a camera, a video camera, an electromagnetic sensor, a computer tomography imaging device, a fluoroscopic imaging device, an ultrasound imaging device, and any combination thereof.

In some embodiments of the current invention, the system additionally comprises a display adapted in a non-limiting manner to provide input or output to the operator regarding the operation of the STS.

In some embodiments of the current invention, the display is adapted in a non-limiting manner to output the acquired real-time images of the surgical environment with augmented reality elements.

In some embodiments of the current invention, the STS further comprises in a non-limiting manner an endoscope controller adapted to control the operation of the endoscope by performing operations selected from a group consisting, for example, of: acquire real-time images, zoom-in to a predetermined area, and any combination thereof.

In some embodiments of the current invention, the STS additionally comprises in a non-limiting manner means adapted to apply a preliminary tag to at least one of the surgical tools.

In some embodiments of the current invention, the STS additionally comprises means adapted in a non-limiting manner to apply a constant tag at least one of the surgical tools.

In some embodiments of the current invention, the STS additionally comprises means adapted in a non-limiting manner to re-tag at least one of the surgical tools until a desired tool is selected.

In some embodiments of the current invention, the STS additionally comprises means adapted in a non-limiting manner to toggle between the surgical tools.

In some embodiments of the current invention, toggling is performed manually or automatically.

In some embodiments of the current invention, the STS additionally comprises a surgical controlling system (SCS), comprising (i) at least one location estimating means adapted to estimate the location of the at least one surgical tool; and (ii) a controller having a processing means communicable with a database, the controller adapted to control the spatial position of the at least one surgical tool. The database is adapted to store a predetermined set of rules according to which ALLOWED and RESTRICTED movements of at least one surgical tool are determined, such that the spatial position of at least one surgical tool is controlled by the controller according to the ALLOWED and RESTRICTED movements.

In some embodiments of the current invention, the predetermined set of rules is selected in a non-limiting manner from a group consisting, for example, of: most used tool, right tool rule, left tool rule, field of view rule, no fly zone rule, route rule, environment rule, operator input rule, proximity rule; collision prevention rule, history based rule, tool-dependent ALLOWED and RESTRICTED movements rule, and any combination thereof.

In some embodiments of the current invention, the route rule comprises in a non-limiting manner a predefined route in which the at least one surgical tool is adapted to move within the surgical environment; the ALLOWED movements are movements in which the at least one surgical tool is located within the borders of the predefined route, and the RESTRICTED movements are movements in which the at least one surgical tool is located outside of the borders of the predefined route.

In some embodiments of the current invention, the environment rule is adapted in a non-limiting manner to determine the ALLOWED and RESTRICTED movements according to hazards or obstacles in the surgical environment as received from an endoscope or other sensing means.

In some embodiments of the current invention, the operator input rule is adapted in a non-limiting manner to receive an input from operator of the SCS regarding the ALLOWED and RESTRICTED movements of the at least one surgical tool.

In some embodiments of the current invention, the operator input rule is adapted in a non-limiting manner to convert an ALLOWED movement to a RESTRICTED movement and a RESTRICTED movement to an ALLOWED movement.

In some embodiments of the current invention, the proximity rule is adapted in a non-limiting manner to define a predetermined distance between the at least one surgical tool and at least one other surgical tool; the ALLOWED movements are movements which are within the range or out of the range of the predetermined distance, and the RESTRICTED movements are movements which are within the range or out of the range of the predetermined distance; the ALLOWED movements and RESTRICTED movements are defined according to different ranges.

In some embodiments of the current invention, the collision prevention rule is adapted to, in a non-limiting manner, define a predetermined distance between the at least one surgical tool and an anatomical element within the surgical environment; the ALLOWED movements are movements which are in a range that is larger than the predetermined distance, and the RESTRICTED movements are movements which are in a range that is smaller than the predetermined distance.

In some embodiments of the current invention, the anatomical element is selected in a non-limiting manner from a group consisting for example of: tissue, an organ, another surgical tool and any combination thereof.

In some embodiments of the current invention, the surgical tool is an endoscope.

In some embodiments of the current invention, the right tool rule is adapted in a non-limiting manner to determine the ALLOWED movement of the endoscope according to the movement of the right tool.

In some embodiments of the current invention, the left tool rule is adapted in a non-limiting manner to determine the ALLOWED movement of the endoscope according to the movement of the left tool.

In some embodiments of the current invention, the field of view rule is adapted in a non-limiting manner to determine the ALLOWED movement of the endoscope so as to maintain a constant field of view.

In some embodiments of the current invention, the no fly zone rule is adapted in a non-limiting manner to define a movement as a RESTRICTED movement if the movement is within the no fly zone and as an ALLOWED movement if the movement is outside the no fly zone.

In some embodiments of the current invention, the most used tool function is adapted in a non-limiting manner to instruct the maneuvering subsystem to constantly position the endoscope to track the movement of the most moved tool.

In some embodiments of the current invention, the SCS is adapted in a non-limiting manner to alert the physician of a RESTRICTED movement of the at least one surgical tool.

In some embodiments of the current invention, the alert is selected in a non-limiting manner from a group consisting, for example, of audio signaling, voice signaling, light signaling, flashing signaling and any combination thereof.

In some embodiments of the current invention, an ALLOWED movement is permitted in a non-limiting manner by the SCS and a RESTRICTED movement is denied by the SCS.

In some embodiments of the current invention, the history based rule is adapted in a non-limiting manner to determine ALLOWED and RESTRICTED movements according to historical movements of the at least one surgical tool in at least one previous surgery.

In some embodiments of the current invention, the tool-dependent ALLOWED and RESTRICTED movements rule is adapted in a non-limiting manner to determine the ALLOWED and RESTRICTED movements according to predetermined characteristics of the surgical tool; the predetermined characteristics of the surgical tool are selected from a group consisting, for example, of: physical dimensions, structure, weight, sharpness, and any combination thereof.

In some embodiments of the current invention, the maneuvering subsystem is adapted in a non-limiting manner to spatially reposition at least one surgical tool during surgery according to the predetermined set of rules.

Figure 22:
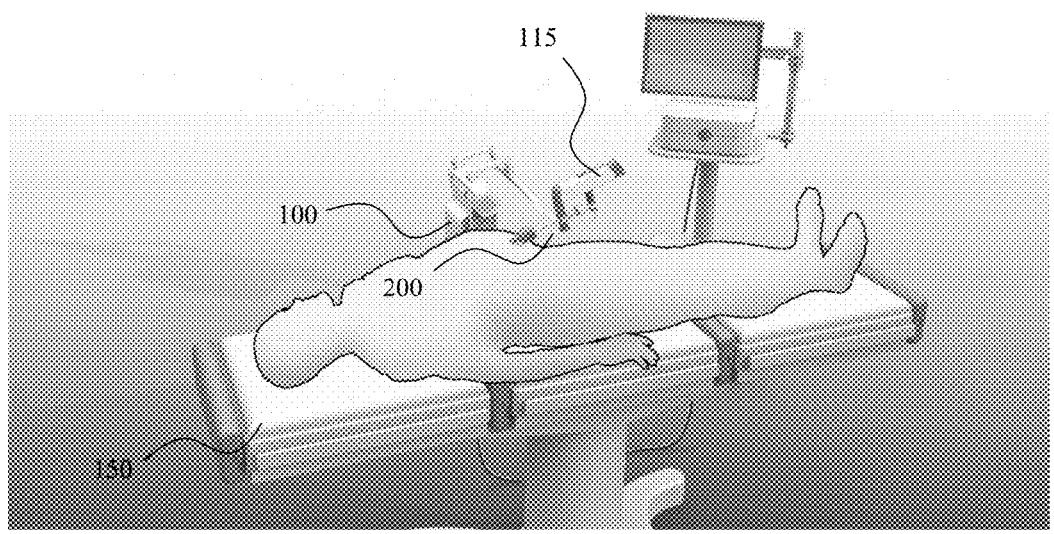
FIG. 22 shows an examining room configuration adapted to use a system for maneuvering an endoscope.

Reference is now made to FIG. 22 which presents, in a non-limiting manner, a possible configuration of system 100, endoscope 200, zoom mechanism 115, and hospital bed 150.

Figure 23:
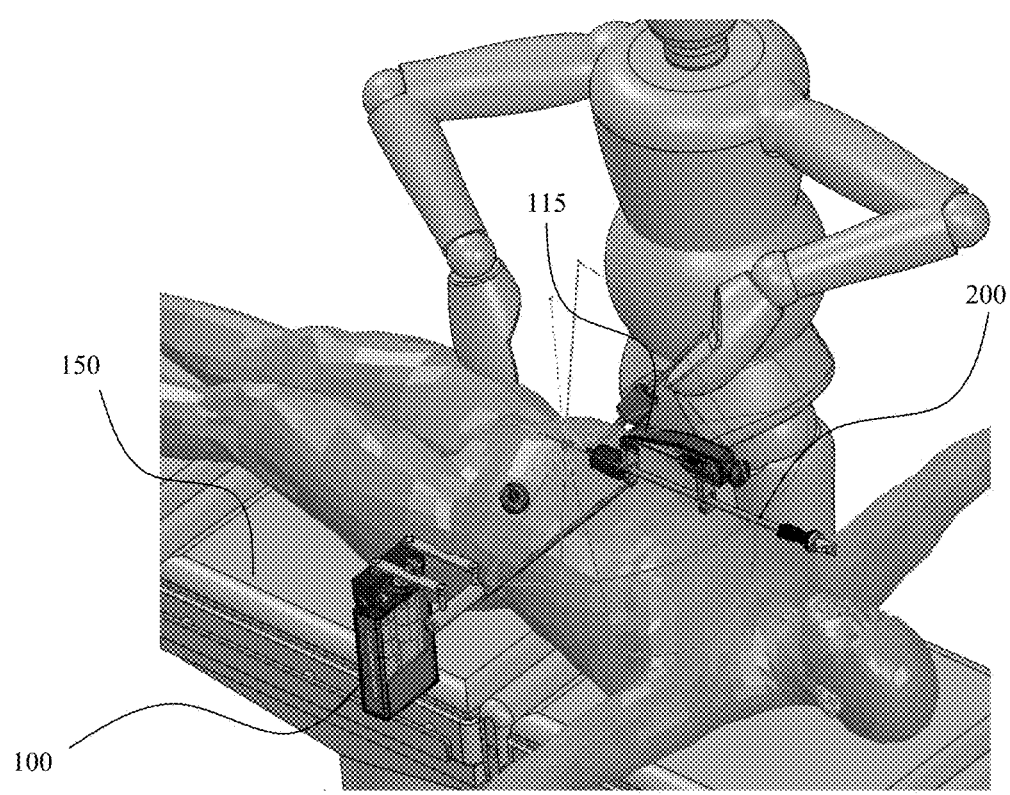
FIG. 23 presents a configuration of system with a hospital bed and an endoscope.

Reference is now made to FIG. 23, which presents, in a non-limiting manner, attaching means adapted to reversibly couple system 100 to a hospital bed 150. Attaching means are selected in a non-limiting manner from a group consisting, for example, of mechanical means as defined above, magnetic means as defined above and any combination thereof. FIG. 23 also illustrates a main core concept of the invention, which enables the utilization of the endoscope substantially tangential to the upper surface of the treated organ (e.g. the abdominal cavity).

Figure 24:
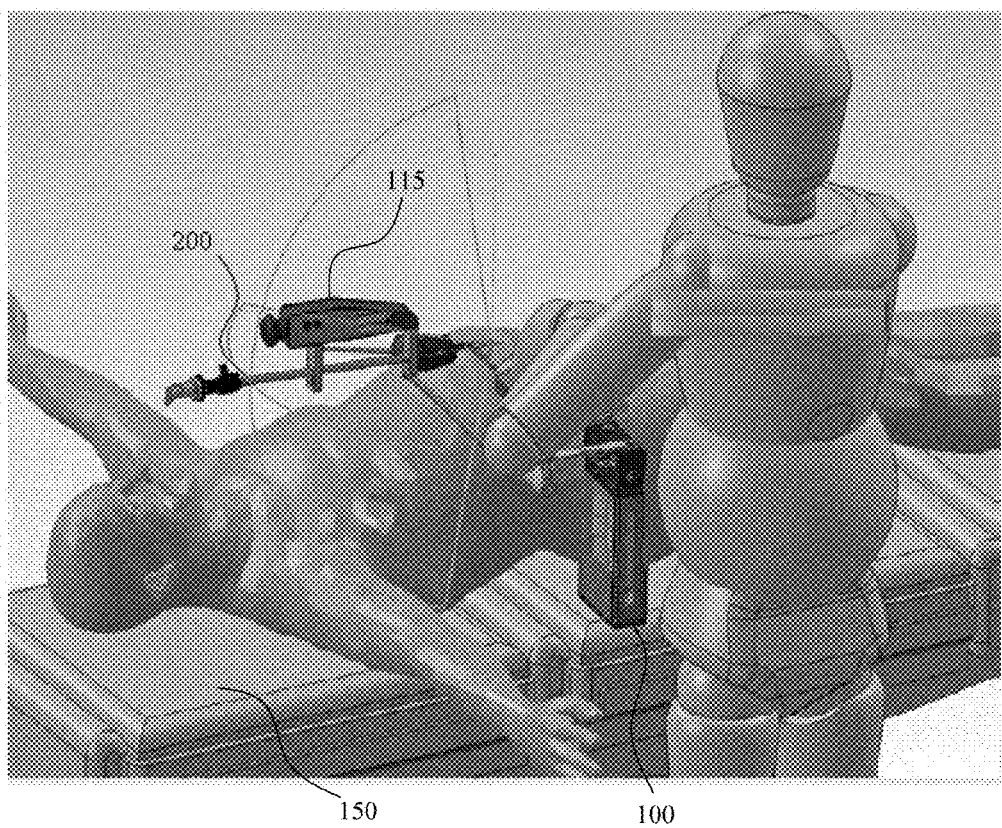
FIG. 24 depicts another configuration of the system in an operating room, with an emphasis on movement range.

Reference is now made to FIG. 24 which presents, in a non-limiting manner, a possible configuration of system 100, endoscope 200, zoom mechanism 115, and hospital bed 150. As illustrated in both FIGS. 23 and 24, the system of the present invention enables the operation of the endoscope while the same is substantially parallel to the upper surface of the treated organ (e.g., the abdominal cavity) and, therefore, almost parallel to hospital bed.

Figure 25:
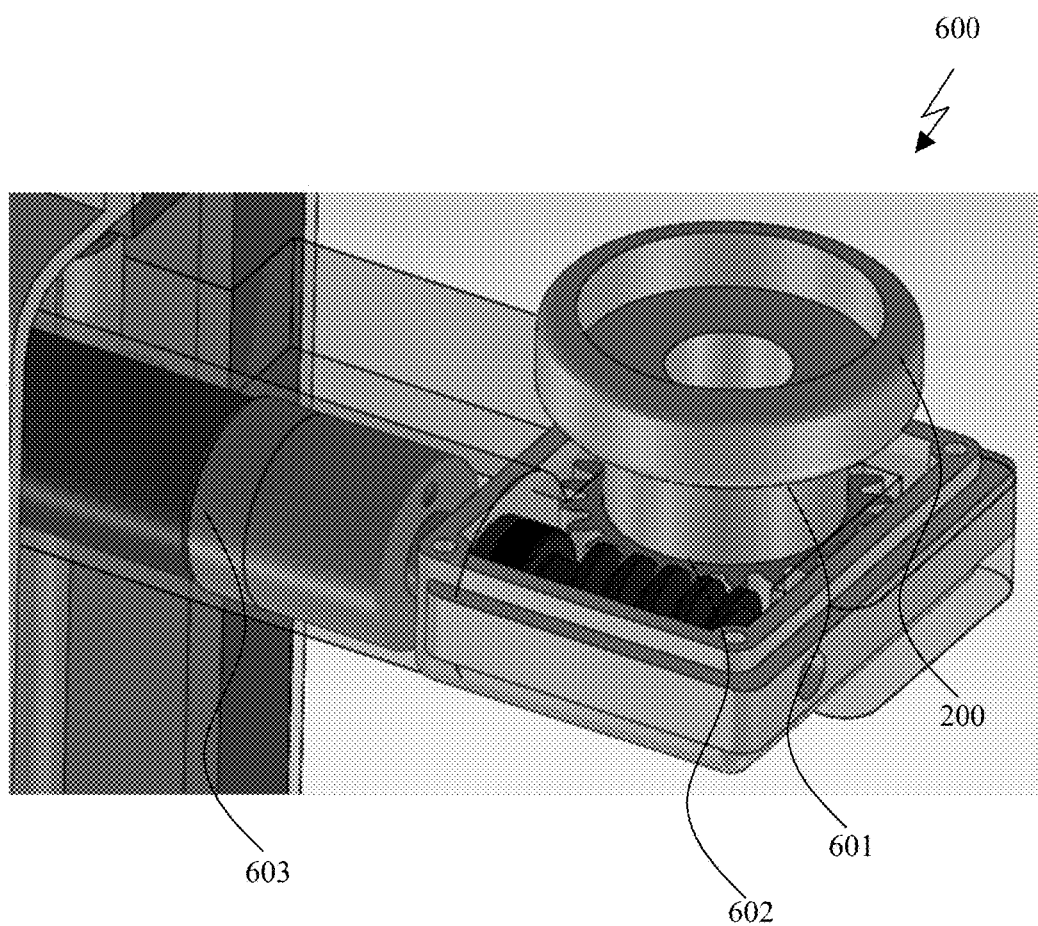
FIG. 25 presents a means adapted to rotate the endoscope around its longitudinal axis.

Reference is now made to FIG. 25, which illustrates, in a non-limiting manner, means 600 adapted to rotate an endoscope around the endoscope's main longitudinal axis.

Means 600 comprises at least one transmission means 601 in communication with the endoscope 200; a transmission means 602 in communication with transmission means 601, and a motor 603 in communication with transmission means 602, adapted to activate the transmission means 602.

Once motor 603 is activated, transmission means 602 is actuated; and transmission means 601 is rotated. Once transmission means 601 is activated, the endoscope is rotated around its main longitudinal axis.

It will be apparent to one skilled in the art that there are several embodiments of the invention that differ in details of construction, without affecting the essential nature thereof, and therefore the invention is not limited by that which is illustrated in the figures and described in the specification, but only as indicated in the accompanying claims, with the proper scope determined only by the broadest interpretation of the claims.

EXAMPLES

Examples are given in order to prove the embodiments claimed in the present invention. The example, which is a clinical test, describes the manner and process of the present invention and set forth the best mode contemplated by the inventors for carrying out the invention, but are not to be construed as limiting the invention.

In the examples below, similar numbers refer to similar parts in all of the figures.

Example 1—Tracking System with Collision Avoidance System

One embodiment of such a rule-based system will comprise the following set of commands:
Detection (denoted by Gd):
 Gd1 Tool location detection function
 Gd2 Organ (e.g. Liver) detection function
 Gd3 Movement (vector) calculation and estimation function
 Gd4 Collision probability detection function
Tool Instructions (denoted Gt):
 Gt1 Move according to manual command
 Gt2 Stop movement
The scenario—manual move command by the surgeon:
Locations Gd1(t) and Gd2(t) are calculated in real time at each time step (from an image or location marker).

Tool movement vector Gd3(t) is calculated from Gd1(t) as the difference between the current location and at least one previous location (probably also taking into account previous movement vectors).

The probability of collision—Gd4(t)—is calculated, for example, from the difference between location Gd1 and location Gd2 (the smaller the distance, the closer the proximity and the higher the probability of collision), from movement vector Gd3(t) indicating a collision, etc.

Weight function $a_1(t)=1$ If $Gt1(t)<a$ predetermined threshold and 0 otherwise    Tool Instructions Gt1

Weight function $a_2(t)=1$ If $Gt2(t)>a$ predetermined threshold and 0 otherwise    Tool Instructions Gt2

Tool Instructions=$a_1(t)*Gt1+a_2(t)*Gt2(t)$;

In reference to FIG. 26, which shows, in a non-limiting manner, an embodiment of a tracking system and collision avoidance system. The system tracks a tool 1810 and the liver 1820, in order to determine whether a collision between the tool 1810 and the liver 1820 is possible within the next time step. FIGS. 26a and 26b show how the behavior of the system depends on the distance 1830 between the tool 1810 and the liver 1820, while FIGS. 26c and 26d show how movement of the tool 1810 affects the behavior. In FIG. 26a, the distance 1830 between the tool 1810 and the liver 1820 is large enough that a collision is not possible in that time step. Since no collision is possible, no movement of the tool is commanded. In FIG. 26b, the distance 1830 between the tool 1810 and the liver 1820 is small enough that a collision is likely. In the embodiment illustrated, a movement 1840 is commanded to move the tool 1810 away from the liver 1820. In other embodiments, the system prevents movement 1850, but does not command movement 1840; in such embodiments, the tool 1810 will remain close to the liver 1820. In yet other embodiments, the system warns/signals the operator that the move is RESTRICTED, but does not restrict movement 1850 or command movement 1840 away from the liver. Such a warning/signaling can be visual or aural, using any of the methods known in the art.

Figure 26A:
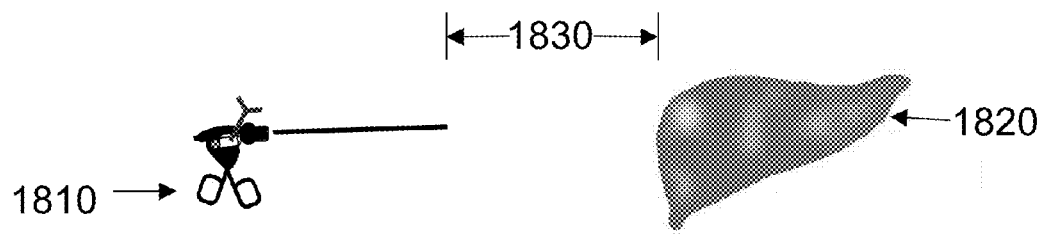
FIG. 26a-26d schematically illustrates operation of an embodiment of a tracking system with collision avoidance system.
Figure 26B:
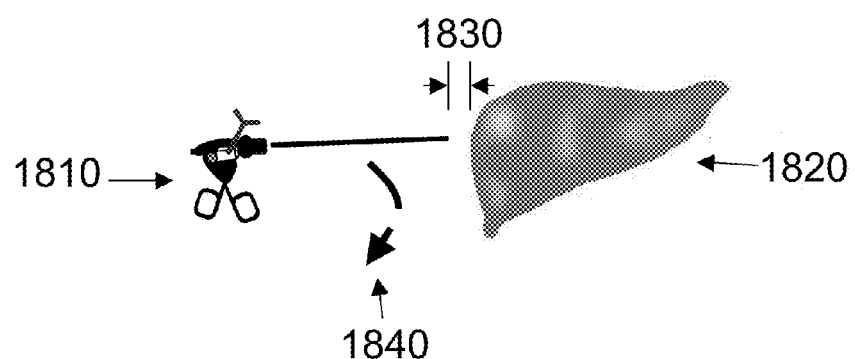
Figure 26C:
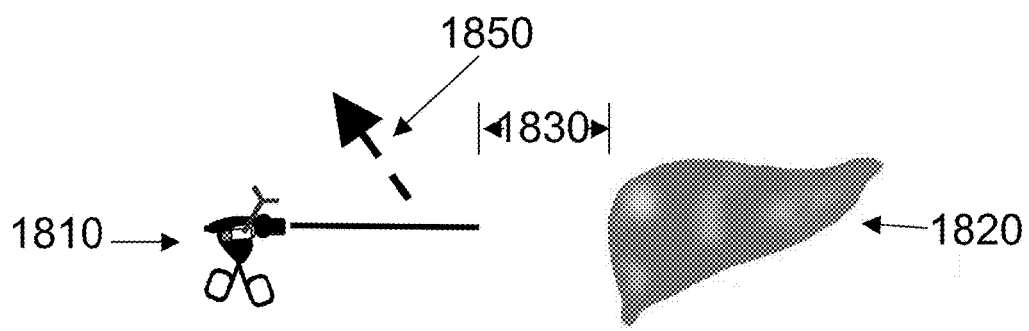
Figure 26D:
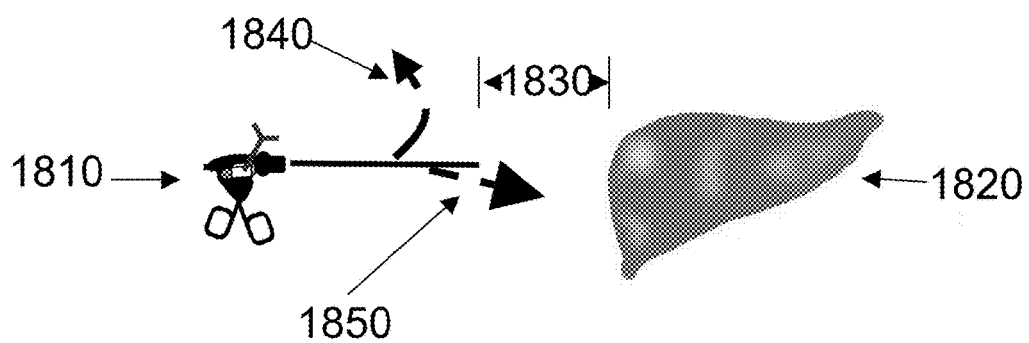

FIGS. 26c and 26d illustrate schematically the effect of the movement of tool 1810 on the collision avoidance system. In FIGS. 26c and 26d, the tool 1810 is close enough to the liver 1820 that a collision between the two is possible. If the system tracked only the positions of the tool 1810 and the liver 1820, then motion of the tool 1810 away from the liver 1820 would be commanded. FIG. 26c illustrates the effect of a movement 1850 that would increase the distance between tool 1810 and liver 1820. Since the movement 1850 is away from liver 1820, no collision is possible in this time step and no movement of the tool 1810 is commanded.

In FIG. 26d, tool 1810 is the same distance from liver 1820 as in FIG. 26c. However, in FIG. 26d, the movement 1850 of the tool 1810 is toward the liver 1820, making a collision between tool 1810 and liver 1820 possible. In some embodiments, a movement 1840 is commanded to move the tool 1810 away from the liver 1820. In other embodiments, the system prevents movement 1850, but does not command movement 1840; in this embodiment the tool 1810 will remain close to the liver 1820. In yet other embodiments, the system warns the operator that move is RESTRICTED, but does not restrict movement 1850 or command movement 1840 away from the liver. Such a warning can be visual or aural, using any of the methods known in the art.

As a non-limiting example, in an operation on the liver, the collision detection function can warn the operator that a collision between a tool and the liver is likely but not prevent the collision. In an operation on the gall bladder, the collision detection function can prevent a collision between the tool and the liver, either by preventing the movement or by commanding a movement redirecting the tool away from the liver, Example 2—Tracking System with Soft Control—Fast Movement when Nothing is Nearby, Slow Movement when Something is Close One embodiment of such rule-based system comprises the following set of commands:
Detection (denoted by Gd):
Main Tool location detection function (denoted by GdM);
Gd-tool1-K—Tool location detection function;
Gd-organ2-L—Organ (e.g. Liver) detection function;
Gd3 Main Tool Movement (vector) calculation and estimation function;
Gd4 Proximity probability detection function;
Tool Instructions (denoted Gt):
Gt1 Movement vector (direction and speed) according to manual command The scenario—manual move command by the surgeon:
Locations GdM(t), Gd-tool1-K(t) and Gd-organ2-L(t) are calculated in real time at each time step (from image or location marker).

Main Tool Movement Vector Gd3(t) is calculated per GdM (t) as the difference between the current location and at least one previous location (probably also taking into account previous movement vectors)

The proximity of the main tool to other tools—Gd4(t)—is calculated, for example, as the smallest of the differences between the main tool location and the other tools' locations.

Tool Instructions Gt1 Weight function $a_1(t)$ is proportional to tool proximity function Gd4(t), the closer the tool the slower the movement so that, for example $a_2(t) = Gd4/\text{maximum}(Gd4)$ or $a_2(t) = \log(Gd4/\text{maximum}(Gd4))$ where maximum(Gd4) is the maximum distance which is likely to result in a collision given the distances, the speed of the tool and the movement vector.

Tool Instructions=$a_1(t)*Gt1$.

Example 3—Tracking System with No-Fly Rule/Function

In reference to FIG. 27, which shows, in a non-limiting manner, an embodiment of a tracking system with no-fly rule. The system tracks a tool 1810 with respect to a no-fly zone (1960), in order to determine whether the tool will enter the no-fly zone (1960) within the next time step. In this example, the no-fly zone 1960 surrounds the liver.

Figure 27A:
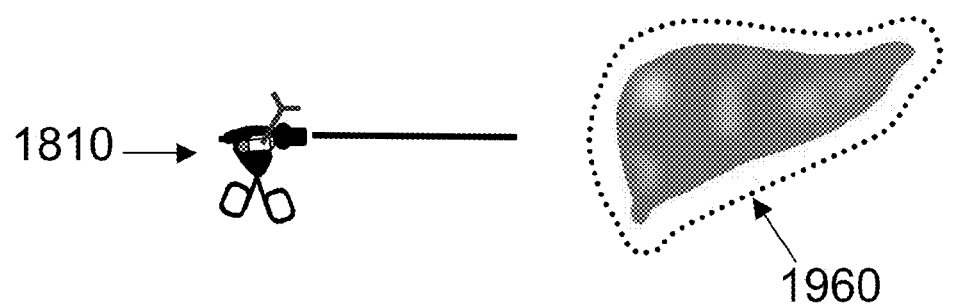
FIG. 27a-27d schematically illustrates operation of an embodiment of a tracking system with no fly zone rule/function.
Figure 27B:
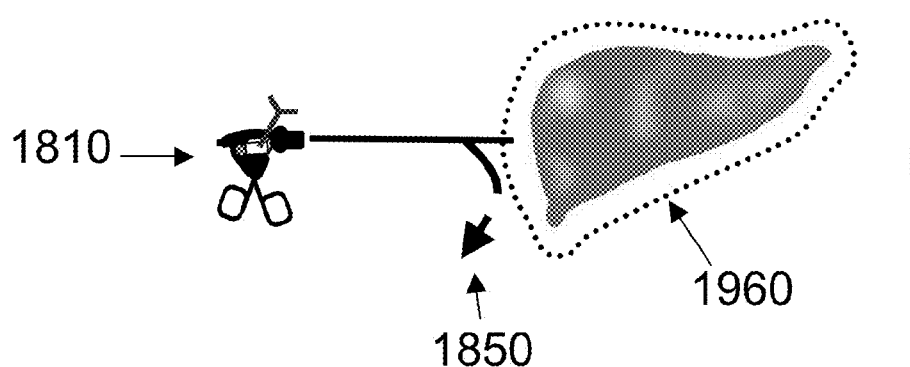
Figure 27C:
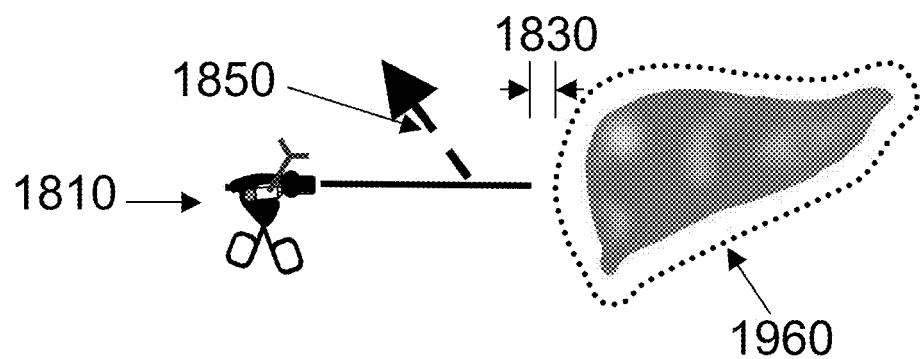
Figure 27D:
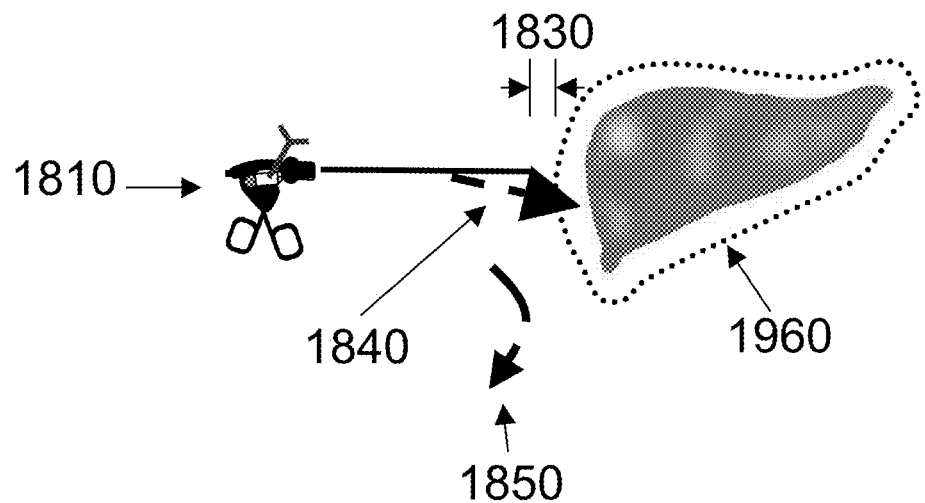

FIGS. 27*a* and 27*b* show how the behavior of the system depends on the location of the tool tip with respect to the no-fly zone, while FIGS. 27*c* and 27*d* show how movement of the tool affects the behavior.

In FIG. 27*a*, the tool 1810 is outside the no-fly zone rule/function 1960 and no movement of the tool is commanded. In FIG. 27*b*, the tool 1810 is inside the no-fly zone 1960.

The no-fly zone rule/function performs as follows:
In the embodiment illustrated, a movement 1850 is commanded to move the tool 1810 away from the no-fly zone 1960. In other embodiments, the system prevents movement further into the no-fly zone (refers as movement 1840, see FIG. 27*c*), but does not command movement 1840; in such embodiments, the tool 1810 will remain close to the no-fly zone 1960.

In yet other embodiments, the system warns/signals the operator that the move is RESTRICTED, but does not restrict movement further into the no-fly zone or command movement 1840 away from the no-fly zone 1960. Such a warning/signaling can be visual or aural, using any of the methods known in the art.

FIGS. 27*c* and 27*d* illustrate schematically the effect of the tool's movement on operation of the no-fly zone rule/function. In FIGS. 27*c* and 27*d*, the tool 1810 is close enough to the no-fly zone 1960 (distance 1830 is small enough) that it is possible for the tool to enter the no-fly zone during the next time step. FIG. 27*c* illustrates the effect of a movement 1840 that would increase the distance between tool 1810 and no-fly zone 1960. Since the movement 1840 is away from no-fly zone 1960, no collision is possible in this time step and no movement of the tool 1810 is commanded.

In FIG. 27*d*, tool 1810 is the same distance from no-fly zone 1960 as in FIG. 27*c*. However, in FIG. 27*d*, the movement 1840 of the tool is toward no-fly zone 1960, making it possible for tool 1810 to enter no-fly zone 1960. In the embodiment illustrated, a movement 1850 is commanded to move the tool 1810 away from the no-fly zone 1960. In other embodiments, the system prevents movement 1840, but does not command movement 1850; in such embodiments, the tool 1810 will remain close to the no-fly zone 1960. In yet other embodiments, the system warns/signals the operator that the move is RESTRICTED, but does not restrict movement 1840 or command movement 1850 away from the no-fly zone rule/function 1960. Such a warning/signaling can be visual or aural, using any of the methods known in the art.

Example 4—Tracking System with Preferred Volume Zone Rule/Function

In reference to FIG. 28, which shows, in a non-limiting manner, an embodiment of a tracking system with a preferred volume zone function/rule.

The system tracks a tool 1810 with respect to a preferred volume zone (2070), in order to determine whether the tool will leave the preferred volume (2070) within the next time step.

Figure 28A:
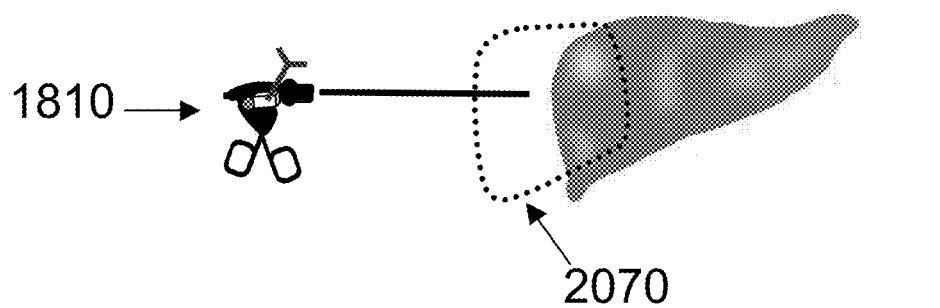
FIG. 28a-28d schematically illustrates operation of an embodiment of a tracking system with preferred volume zone rule/function.
Figure 28B:
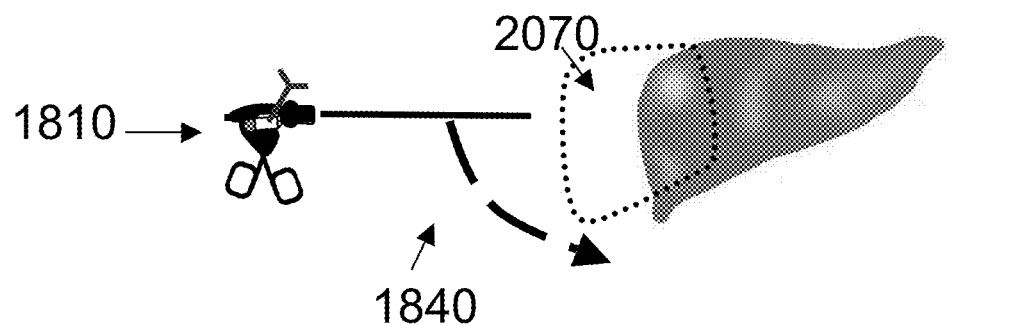

In this example, the preferred volume zone 2070 extends over the right lobe of the liver. FIGS. 28*a* and 28*b* show how the behavior of the system depends on the location of the tool tip with respect to the preferred volume zone 2070, while FIGS. 28*c* and 28*d* show how movement of the tool affects the behavior (i.e., the preferred volume zone rule/function).

In FIG. 28a, the tool 1810 is inside the preferred volume zone 2070 and no movement of the tool is commanded. In FIG. 28b, the tool 1810 is outside the preferred volume zone 2070.

In the embodiment illustrated, a movement 1840 is commanded to move the tool 1810 away from the preferred volume zone 2070. In other embodiments, the system prevents movement 1840; in such embodiments, the tool 1810 will remain close to the preferred volume zone 2070. In yet other embodiments, the system warns/signals the operator that the move 1840 is RESTRICTED. Such a warning/signaling can be visual or aural, using any of the methods known in the art.

Figure 28C:
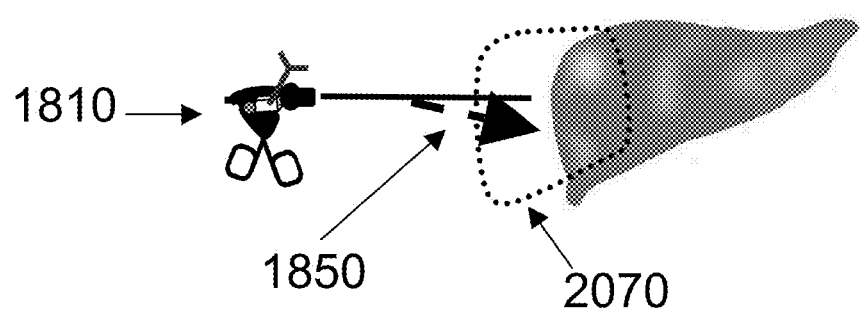
Figure 28D:
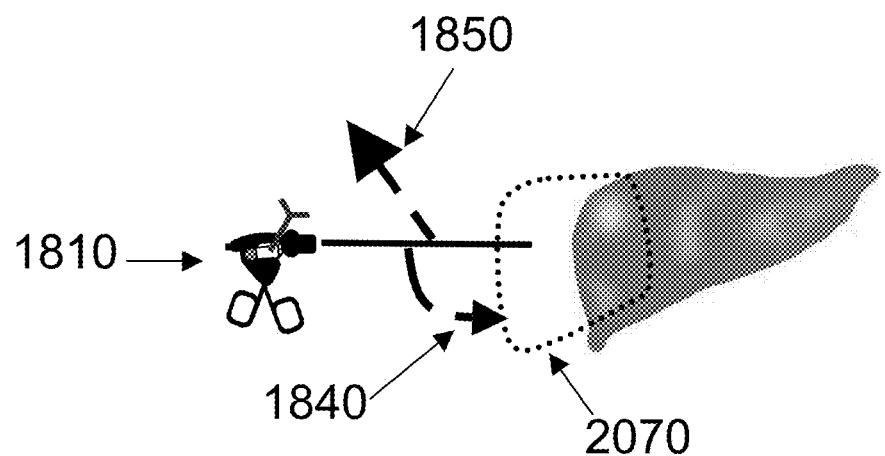

FIGS. 28c and 28d illustrate schematically the effect of the tool's movement on operation of the preferred volume rule/function. In FIGS. 28c and 28d, the tool 1810 is close enough to the edge of preferred volume zone 2070 that it is possible for the tool to leave the preferred volume zone during the next time step.

FIG. 28c illustrates the effect of a movement 1850 that would take the tool 1810 deeper into preferred volume zone 2070. Since the movement 1850 is into preferred volume 2070, said movement is an allowed movement.

In FIG. 28d, the movement 1850 of the tool is out of the preferred volume 2070, making it possible for tool 1810 to leave preferred volume 2070.

According to one embodiment illustrated, a movement 1840 is commanded to move the tool 1810 into the preferred volume zone 2070. In other embodiments, the system prevents movement 1850, but does not command movement 1840; in such embodiments, the tool 1810 will remain close to the preferred volume zone 2070. In yet other embodiments, the system warns/signals the operator that the move is RESTRICTED, but does not restrict movement 1850 or command movement 1840 away from the preferred volume zone 2070. Such a warning/signaling can be visual or aural, using any of the methods known in the art.

Example 5—Organ/Tool Detection Function

Figure 29:
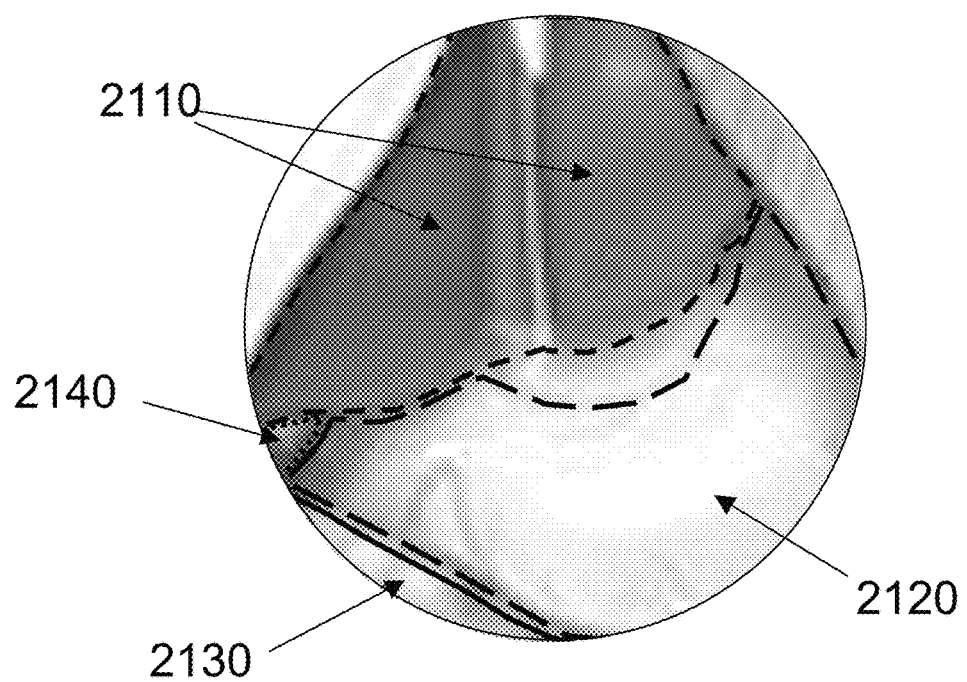
FIG. 29 schematically illustrates operation of an embodiment of the organ detection function/rule.

In reference to FIG. 29, which shows, in a non-limiting manner, an embodiment of an organ detection system (however, it should be noted that the same is provided for detection of tools, instead of organs).

For each organ, the 3D spatial positions of the organs stored in a database. In FIG. 29, the perimeter of each organ is marked, to indicate the edge of the volume of 3D spatial locations stored in the database.

In FIG. 29, the liver 2110 is labeled with a dashed line. The stomach 2120 is labeled with a long-dashed line, the intestine 2130 with a solid line and the gall bladder 2140 is labeled with a dotted line.

In some embodiments, a label or tag visible to the operator is also presented. Any method of displaying identifying markers known in the art can be used. For non-limiting example, in an enhanced display, colored or patterned markers can indicate the locations of the organs, with the marker either indicating the perimeter of the organ or the area of the display in which it appears.

Example 6—Tool Detection Function

Figure 30:
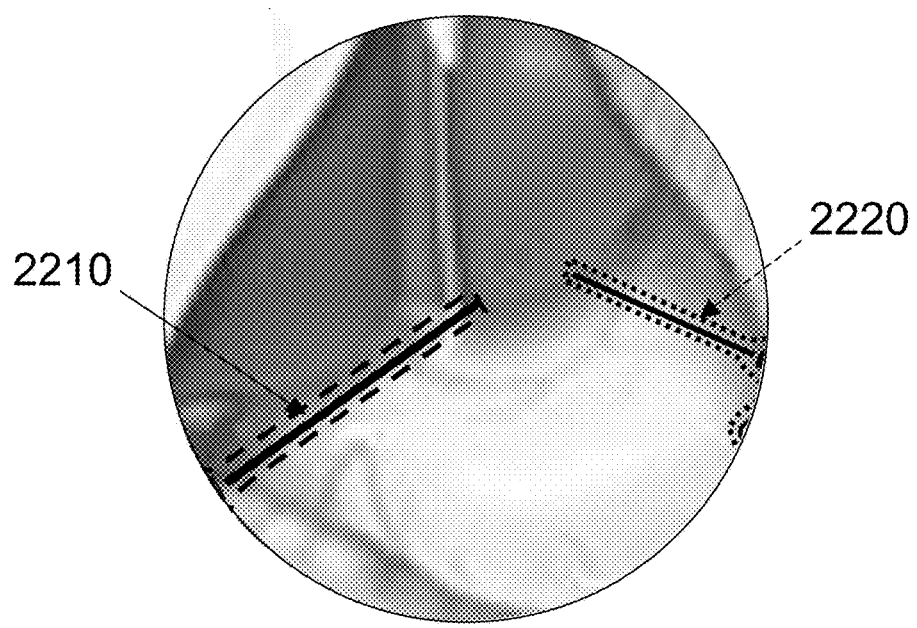
FIG. 30 schematically illustrates operation of an embodiment of the tool detection function/rule.

In reference to FIG. 30, which shows, in a non-limiting manner, an embodiment of a tool detection function. For each tool, the 3D spatial positions of the tools stored in a database. In FIG. 30, the perimeter of each tool is marked, to indicate the edge of the volume of 3D spatial locations stored in the database. In FIG. 30, the left tool is labeled with a dashed line while the right tool is labeled with a dotted line.

In some embodiments, a label or tag visible to the operator is also presented. Any method of displaying identifying markers known in the art can be used. For non-limiting example, in an enhanced display, colored or patterned markers can indicate the locations of the tools, with the marker either indicating the perimeter of the tool or the area of the display in which it appears.

Example 7—Movement Detection Function/Rule

Figure 31A:
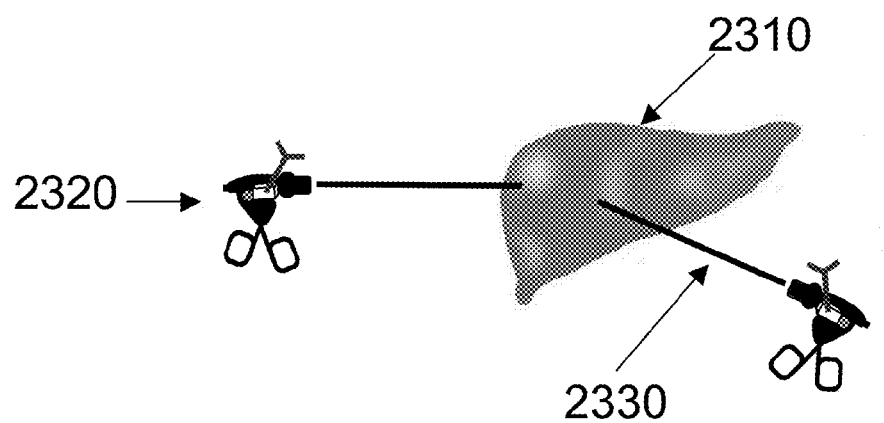
FIG. 31a-31b schematically illustrates operation of an embodiment of the movement detection function/rule.
Figure 31B:
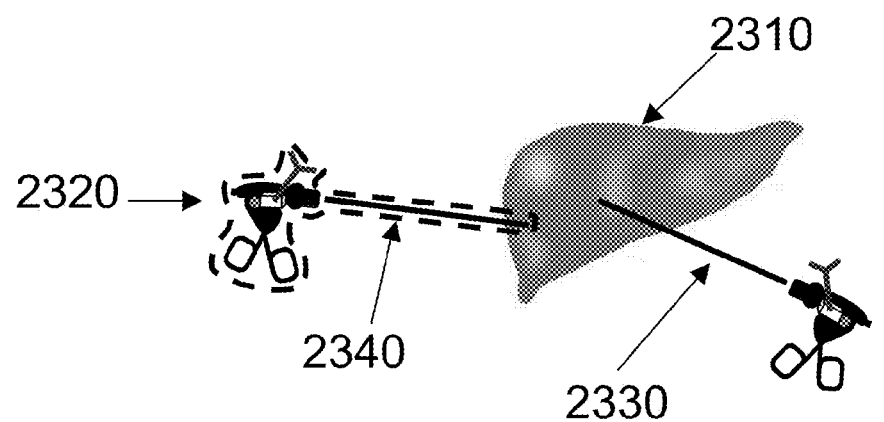

In reference to FIG. 31, which shows, in a non-limiting manner, an embodiment of a movement detection function/rule. FIG. 31a schematically illustrates a liver 2310, a left tool 2320 and a right tool 2330 at a time t. FIG. 31b schematically illustrates the liver 2310, left tool 2320 and right tool 2330 at a later time t+$\Delta$t, where $\Delta$t is a small time interval. In this example, the left tool 2320 has moved downward (towards the direction of liver 2310) in the time interval $\Delta$t.

The system has detected movement of left tool 2320 and labels it. This is illustrated schematically in FIG. 31b by a dashed line around left tool 2320.

Example 8—Prediction Function

In reference to FIG. 32, which shows, in a non-limiting manner, an embodiment of the above discussed prediction function.

Figure 32A:
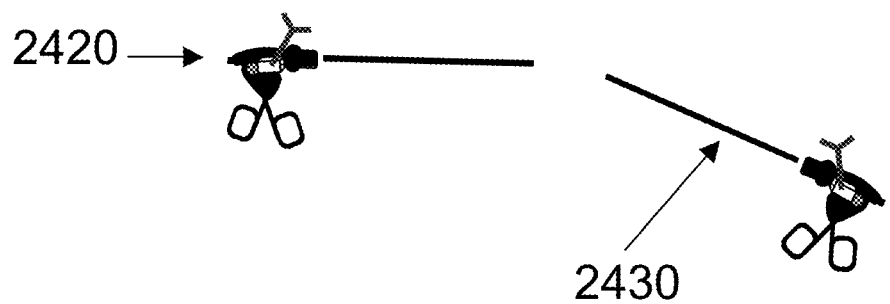
FIG. 32a-32d schematically illustrates operation of an embodiment of the prediction function/rule.

FIG. 32a shows a left tool 2420 and a right tool 2430 at a time t.

Figure 32B:
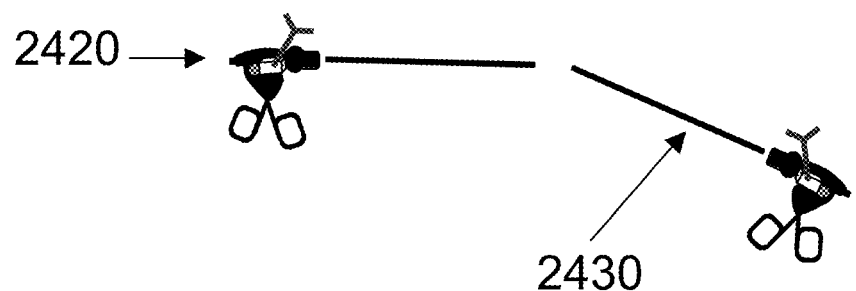
Figure 32C:
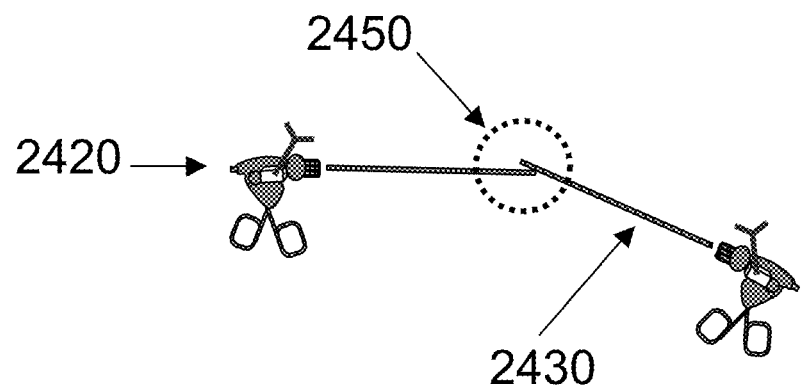
Figure 32D:
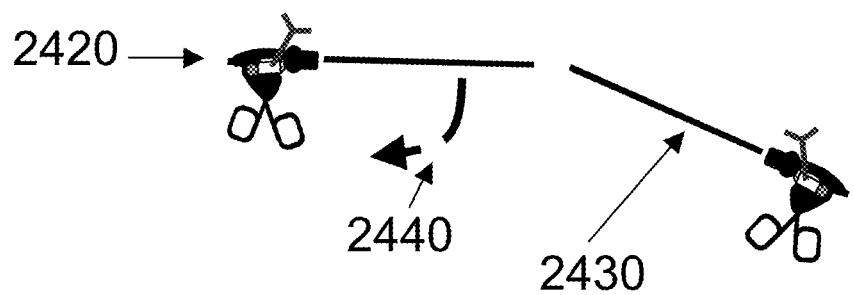

FIG. 32b shows the same tools at a later time t+$\Delta$t, where $\Delta$t is a small time interval. Left tool 2420 is moving to the right and downward, while right tool 2430 is moving to the left and upward. If the motion continues (shown by the dashed line in FIG. 32c), then by the end of the next time interval, in other words, at some time between time t+$\Delta$t and time t+2$\Delta$t, the tools will collide, as shown by tool tips within the dotted circle 2450 in FIG. 32c.

In this embodiment, the system automatically prevents predicted collisions and, in this example (FIG. 32d), the system applies a motion 2440 to redirect left tool 2420 so as to prevent the collision.

In other embodiments, the system warns/signals the operator that a collision is likely to occur, but does not alter the movement of any tool. Such a warning/signaling can be visual or aural, using any of the methods known in the art.

In other embodiments, the prediction function can be enabled to, for non-limiting example, alter the field of view to follow the predicted movement of a tool or of an organ, to warn of (or prevent) predicted motion into a no-fly zone, to warn of (or prevent) predicted motion out of a preferred zone.

Example 9—Right Tool Function/Rule

Figure 33:
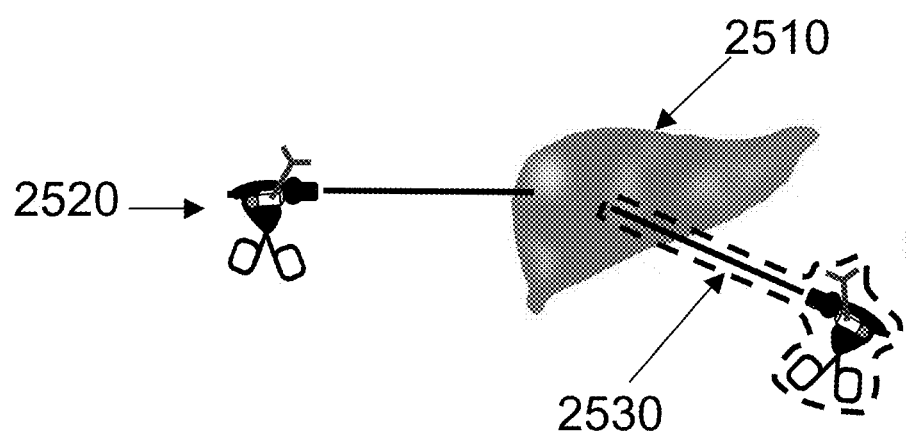
FIG. 33 schematically illustrates operation of an embodiment of the right tool function/rule.

In reference to FIG. 33, which shows, in a non-limiting manner, an embodiment of a right tool function. FIG. 33 schematically illustrates a liver 2510, a left tool 2520 and a right tool 2530. The right tool, illustrated schematically by the dashed line 2540, is labeled and its 3D spacial location is constantly and real-time stored in a database. Now, according to the right tool function/rule the endoscope constantly tracks the right tool.

It should be pointed out that the same rule/function applies for the left tool (the left tool function/rule).

Example 10—Field of View Function/Rule

In reference to FIG. 34, which shows, in a non-limiting manner, an embodiment of a field of view function/rule.

Figure 34A:
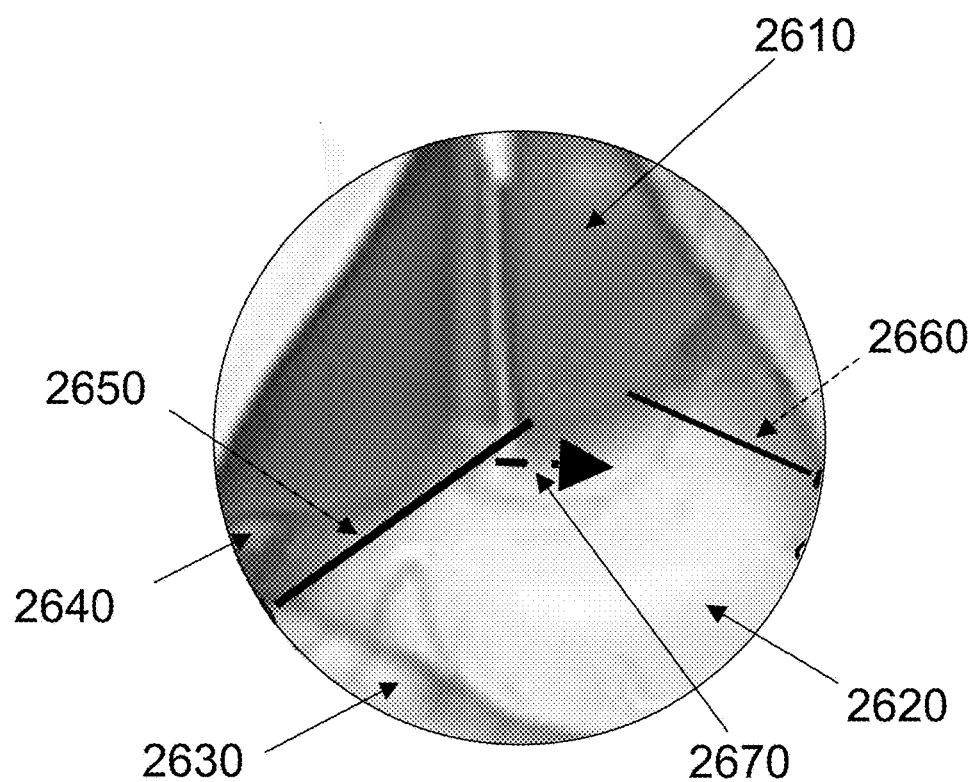
FIG. 34a-34b schematically illustrates operation of an embodiment of the field of view function/rule.

FIG. 34a schematically illustrates a field of view of the abdomen at a time t. In the field of view are the liver 2610, stomach 2620, intestines 2630 and gall bladder 2640.

The gall bladder is nearly completely visible at the left of the field of view. Two tools are also in the field of view, with their tips in proximity with the liver. These are left tool 2650 and right tool 2660. In this example, the field of view function/rule tracks left tool 2650. In this example, left tool 2650 is moving to the right, as indicated by arrow 2670.

Figure 34B:
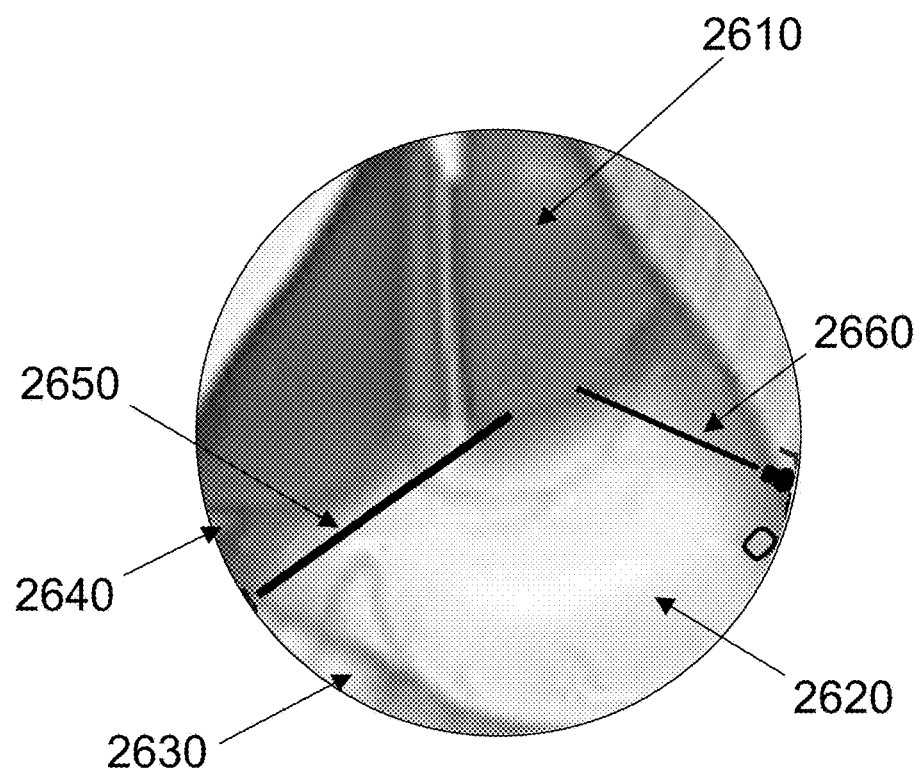

FIG. 34b shows the field of view at time t+Δt. The field of view has moved to the right so that the tip of left tool 2650 is still nearly at the center of the field of view. It can be seen that much less of gall bladder 2640 is visible, while more of right tool 2660 has entered the field of view.

The field of view function/rule can be set to follow a selected tool, as in this example, or to keep a selected organ in the center of the field of view. It can also be set to keep a particular set of tools in the field of view, zooming in or out as necessary to prevent any of the chosen tools from being outside the field of view.

Alternatively, the field of view function/rule defines n 3D spatial positions; n is an integer greater than or equal to 2; the combination of all of said n 3D spatial positions provides a predetermined field of view.

Each movement of the endoscope or the surgical tool within said n 3D spatial positions is an allowed movement and any movement of the endoscope or the surgical tool outside said n 3D spatial positions is a restricted movement.

Alternatively, said the field of view function/rule defines n 3D spatial positions; n is an integer greater than or equal to 2; the combination of all of said n 3D spatial positions provides a predetermined field of view.

According to the field of view function/rule, the endoscope is relocated if movement has been detected by said detection means, such that said field of view is maintained.

Example 11—Tagged Tool Function/Rule (or Alternatively the Preferred Tool Rule)

Figure 35:
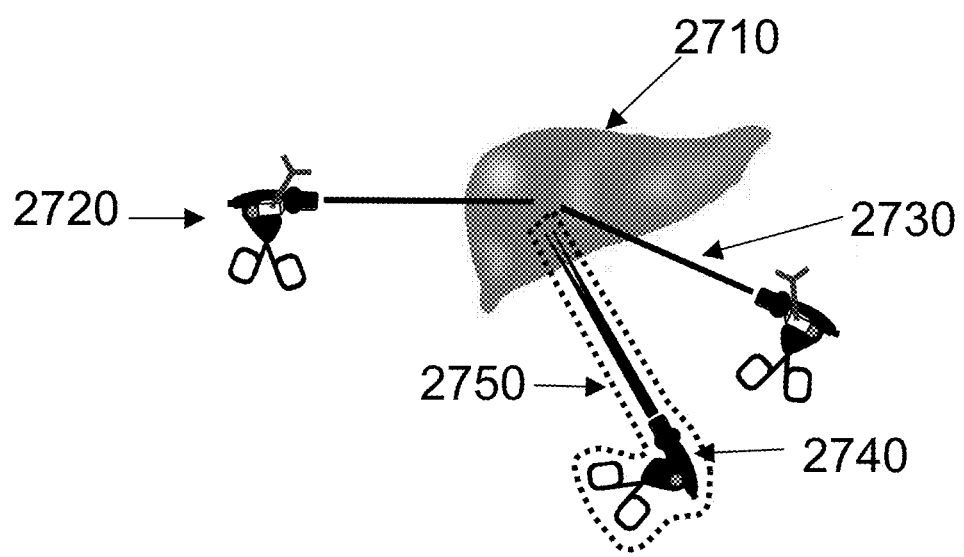
FIG. 35 schematically illustrates operation of an embodiment of the tagged tool function/rule.

In reference to FIG. 35, which shows, in a non-limiting manner, an embodiment of a tagged tool function/rule.

FIG. 35 shows three tools (2720, 2730 and 2740) in proximity to the organ of interest, in this example, the liver 2710.

The tool most of interest to the surgeon, at this point during the operation, is tool 2740. Tool 2740 has been tagged (dotted line 2750); the 3D spacial location of tool 2740 is constantly stored in a database and this spacial location has been labeled as one of interest.

The system can use this tagging for many purposes, including, but not limited to, keeping tool 2740 in the center of the field of view, predicting its future motion, keeping it from colliding with other tools or keeping other tools from colliding with it, instructing the endoscope to constantly monitor and track said tagged tool 2750 and so on.

It should be noted that in the preferred tool rule, the system tags one of the tools and performs as in the tagged tool rule/function.

Example 12—Proximity Function/Rule

In reference to FIG. 36, which shows, in a non-limiting manner, an embodiment of a proximity function/rule.

Figure 36A:
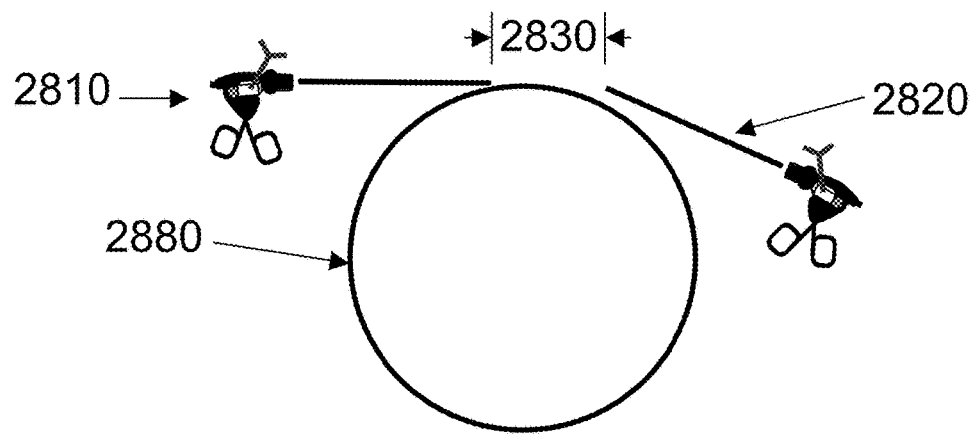
FIG. 36a-36c schematically illustrates operation of an embodiment of the proximity function/rule.

FIG. 36a schematically illustrates two tools (2810 and 2820) separated by a distance 2830 which is greater than a predefined proximity distance. Since tool 2810 is not within proximity of tool 2820, the field of view (2880) does not move.

Figure 36B:
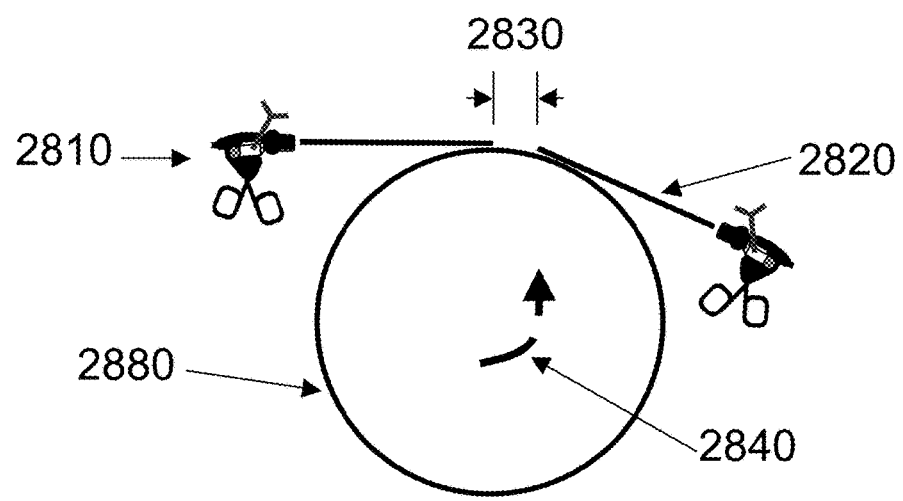

FIG. 36b schematically illustrates two tools (2810 and 2820) separated by a distance 2830 which is less than a predefined proximity distance.

Figure 36C:
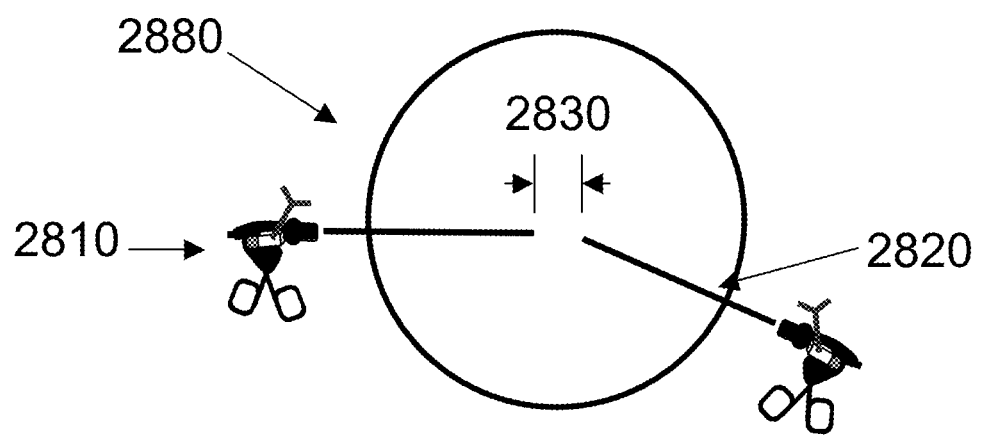

Since tool 2810 is within proximity of tool 2820, the field of view 2880 moves upward, illustrated schematically by arrow 2840, until the tips of tool 2810 and tool 2820 are in the center of field of view 2880 (FIG. 36c).

Alternatively the once the distance 2830 between the two tool 2820 and 2810 is smaller than a predetermined distance, the system alerts the user of said proximity (which might lead to a collision between the two tools). Alternatively, the system moves one of the tools away from the other one.

Example 13—Operator Input Function/Rule

In reference to FIG. 37, which shows, in a non-limiting manner, an embodiment of an operator input function/rule. According to this embodiment, input is received from the operator.

In the following example, the input received from the operator is which tool to track.

Figure 37A:
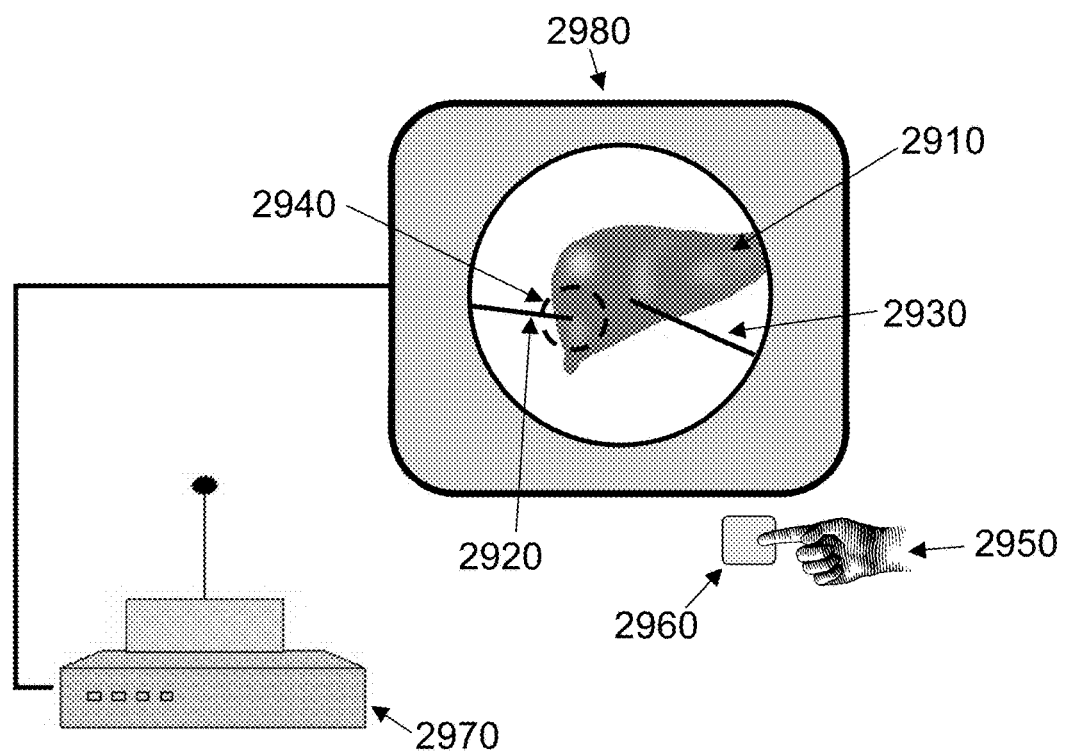
FIG. 37a-37b schematically illustrates operation of an embodiment of the operator input function/rule.

FIG. 37a schematically illustrates an endoscope with field of view 2980 showing a liver 2910 and two tools 2920 and 2930. A wireless transmitter 2960 is enabled to transmit coded instructions through receiver 2970. Operator 2950 first selects the tip of the left tool as the region of interest, causing the system to tag (2940) the tip of the left tool.

Figure 37B:
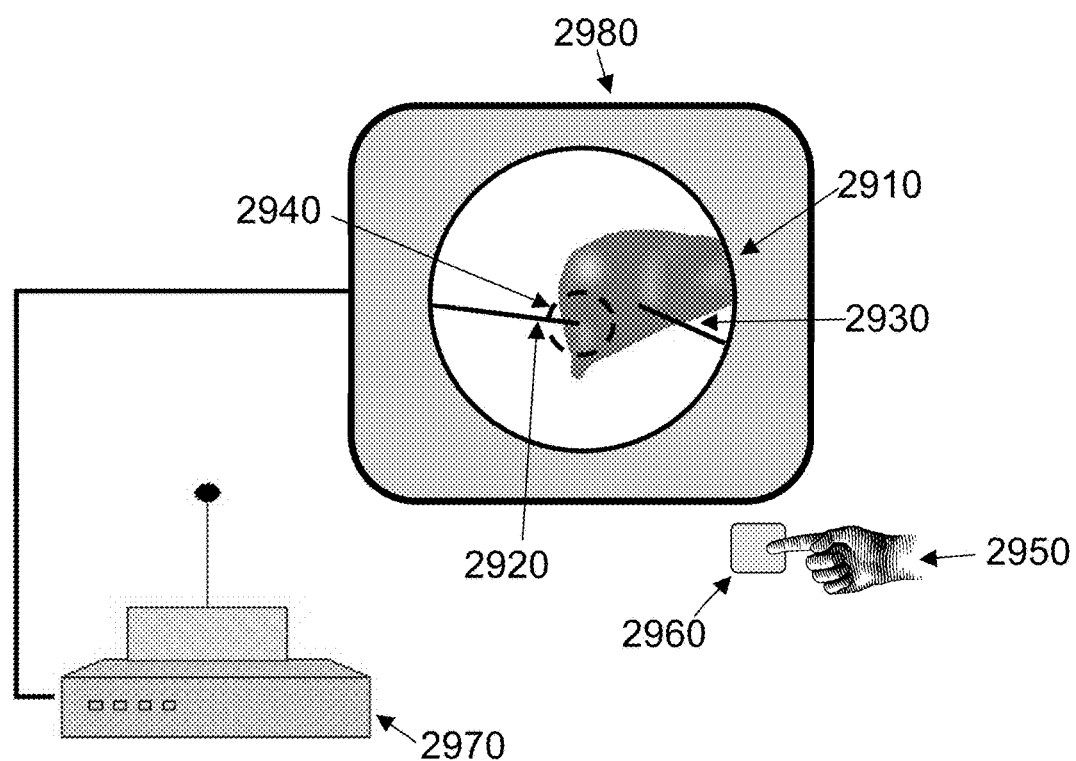

As illustrated in FIG. 37b, the system then directs and modifies the spatial position of the endoscope so that the tagged tool tip 2940 is in the center of the field of view 2980.

Another example of the operator input function/rule is the following:

If a tool has been moved closely to an organ in the surgical environment, according to the proximity rule or the collision prevention rule, the system will, according to one embodiment, prevent the movement of the surgical tool.

According to one embodiment of the present invention, once the surgical tool has been stopped, any movement of said tool in the direction is interpreted as input from the operator to continue the movement of said surgical tool in said direction.

Thus, according to this embodiment, the operator input function/rule receives input from the operator (i.e., physician) to continue the move of said surgical tool (even though it is "against" the collision prevention rule). Said input is simply in the form of the continued movement of the surgical tool (after the alert of the system or after the movement prevention by the system).

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

It will be apparent to one skilled in the art that there are several embodiments of the invention that differ in details of construction, without affecting the essential nature thereof, and therefore the invention is not limited by that which is illustrated in the figures and described in the specification, but only as indicated in the accompanying claims, with the proper scope determined only by the broadest interpretation of the claims.

The invention claimed is:

1. A system for maneuvering an endoscope, comprising:
at least one first pivoting support configured to be pivotally attached to said endoscope; said pivoting support configured to enable said endoscope to pivot around at least one first axis of rotation;
at least one second pivoting support in communication with said at least one first pivoting support, said second pivoting support configured to rotate around at least one axis being substantially orthogonal to said first axis of rotation independently of said first pivoting support; thereby enabling said endoscope to rotate around an insertion point into a body of a subject in at least two orthogonal axes;
at least one controller attached to either said first pivoting support or said second pivoting support,
wherein said controller is configured to provide a constant dynamic equilibrium between said endoscope and at least one selected from a group consisting of said first pivoting support, said second pivoting support and any combination thereof; such that pressure on an insertion point into a patient is prevented;
further wherein said at least one selected from a group consisting of said first pivoting support, said second pivoting support and any combination thereof enable said endoscope to pivot about said insertion point if a line of application of force to move said endoscope is not completely collinear with a main longitudinal axis thereof, without application of force on said pivoting point.

2. The system according to claim 1, wherein at least one of said pivoting supports is configured to moderate said pivoting of said endoscope around either said first axis of rotation or said second axis of rotation.

3. The system according to claim 1, wherein said system further comprises at least one connecting means configured to connect said endoscope to at least one of said pivoting supports.

4. The system according to claim 3, wherein at least one of said pivoting supports is configured to constantly apply a counter torque to oppose the torque induced by said endoscope and said connecting means; further wherein said counter torque varies as said torque varies such that there is provided a constant dynamic equilibrium between said endoscope and at least one of said first pivoting support and said second pivoting support.

5. The system according to claim 1, wherein said first pivoting support is configured to enable said endoscope to pivot around one first axis of rotation and said second pivoting support is configured to enable said endoscope to pivot around a second and third axis of rotation, each of said first axis of rotation, said second axis of rotation and said third axis of rotation being substantially perpendicular to the other two axes of rotation.

6. The system according to claim 1, wherein said controller further comprises at least one element selected from a group consisting of (a) damping mechanism configured to prevent oscillation of the system; (b) at least one of an active mechanism and a passive mechanism to provide said dynamic equilibrium; (c) at least one selected from a group consisting of a motor and a spring; and any combination thereof.

7. The system according to claim 1, wherein said system additionally comprises an automatic assistant in communication with said endoscope configured to maneuver said endoscope.

8. The system of claim 1, further comprising:
a first mechanism, comprising:
a) at least one first transmission means (101); said first transmission means 101 defines a first plane; said first transmission means (101) is characterized by a first axis of rotation; said first axis of rotation is substantially orthogonal to said first plane;
b) at least one second transmission means (102); said second transmission means (102) defines a second plane; said second transmission means is characterized by a second axis of rotation (141); said second axis of rotation (141) is substantially orthogonal to said second plane; said second transmission means (102) is rotatably connected to said first transmission means (101); where said first plane is substantially orthogonal to second plane; and
c) at least one first means (106) configured to rotate said first transmission means (101) around said first axis of rotation; where said first transmission means (101) transmits rotation to said second transmission means (102); and,
a second mechanism, comprising:
a) at least one third transmission means (103); said third transmission means (103) defines a third plane; said third transmission means (103) is characterized by a third axis of rotation; said third axis of rotation is substantially orthogonal to said third plane;
b) at least one fourth transmission means (104); said fourth transmission means (104) defines a fourth plane; said forth transmission means defines a fourth axis of rotation; said fourth axis of rotation is substantially orthogonal to said fourth plane; said fourth transmission means (104) is rotatably connected to said third transmission means (103); where said fourth plane is substantially orthogonal to said third plane;
c) at least one fifth transmission means (105); said fifth transmission means (105) defines a fifth plane; said fifth transmission means defines a fifth axis of rotation (142); said fifth axis of rotation (142) is substantially orthogonal to said fifth plane; said fifth transmission means (105) is rotatably connected to said fourth transmission means (104); where said fifth plane is substantially orthogonal to said fourth plane;
d) at least one second means (107) configured to rotate said third transmission means (103) around said third axis of rotation; where said third transmission means (103) transmits rotation to said fourth transmission means (104); where said fourth transmission means (104) transmits rotation to said fifth transmission means (105),
wherein said first mechanism and said second mechanism are configured to rotate said endoscope around at least one said second axis of rotation (141) being substantially orthogonal to said second plane; and around at least one said fifth axis of rotation (142) being substantially orthogonal to said fifth plane, such that said second axis of rotation (141) and said fifth axis of rotation (142) are positioned at an angle A relative to each other; said angle A between said second axis of rotation (141) and said fifth axis of rotation (142) is in the range of about 0 degrees to about 180 degrees.

9. The system according to claim 8, wherein said rotation in said second plane defines an angle θ; said angle θ varies between about 0 and about 360 degrees, preferably between about 0 and about 160 degrees, when said system is in said automatic configuration or in said manual configuration; further wherein said rotation in said fifth plane defines an angle ψ; said angle ψ varies between about 0 and about 360 degrees, preferably between about 0 and about 140 degrees, when system is in said automatic configuration or in said manual configuration.

10. The system according to claim 8, wherein at least one of the following is being held true (a) said first mechanism additionally comprises locking means configured to maintain in a predetermined orientation upon power failure at least one selected from a group consisting of: said first transmission means, said second transmission means and any combination thereof; and to prevent any rotational movement of the same upon power failure; (b) said second mechanism additionally comprises locking means configured to maintain in a predetermined orientation upon power failure at least one selected from a group consisting of: said third transmission means, said fourth transmission means, said fifth transmission means, and any combination thereof; and to prevent any rotational movement of the same upon power failure; and any combination thereof.

11. The system according to claim 8, wherein a member of a group consisting of said first transmission means (101), said second transmission means (102), said third transmission means (103), said fourth transmission means (104), fifth transmission means (105) and any combination thereof is selected from a group consisting of gearwheels, wheels, crown gears, bevel gears, spur gears, belts and any combination thereof.

12. The system according to claim 1, wherein at least one of the following is being held true (a) said system further comprising at least one zoom mechanism 115, configured to maneuver said endoscope along the main longitudinal axis of the same; (b) either one of said first or second pivoting supports (113 and 114) is a gimbal; and any combination thereof.

13. The system according to claim 1, wherein said system comprises attaching means configured to reversibly couple said system to a hospital bed, said attaching means selected from a group consisting of mechanical means, magnetic means and any combination thereof; said mechanical means is selected from a group consisting of a clip, a fastening element, tape, adhesive tape, a snap fastener, a button and any combination thereof; said magnetic means comprises a magnetic device, said magnetic device comprising at least one magnet and at least one selected from a group consisting of: a ferromagnet and a paramagnet; where said magnet is attached to at least one member of a group consisting of: a hospital bed, said system, and any combination thereof, and said member of said group consisting of a ferromagnet and a paramagnet is attached to at least one member of a group consisting of: a hospital bed, said system, and any combination thereof.

14. The system according to claim 1, wherein said system additionally comprises a quick release handle configured to disassemble said endoscope from said system.

15. The system according to claim 1, additionally comprising at least one manual override system (MOS), configured upon activation of the same to switch reversibly between a manual configuration, in which the endoscope is moved manually by an operator via a manual control mechanism and an automatic configuration, in which the endoscope is moved automatically by the system, and optionally configured to switch reversibly to a wholly manual configuration, in which the endoscope is moved wholly manually by an endoscope assistant.

16. The system according to claim 15, wherein at least one of the following is being held true (a) said system additionally comprises at least one joystick, in communication with said endoscope; (b) said system additionally comprises activation means configured to activate at least one of a group consisting of said system, said joystick and any combination thereof; (c) said activation means is configured to be worn by an operator; (d) said activation means is selected from a group consisting of a pres sable button, a rotatable knob, a knob, and any combination thereof; and (e) said MOS additionally comprises n sensors, where n is an integer greater than or equal to one; wherein said sensors are selected from of a group consisting of: motion sensors, heat sensors, electric sensors, sound sensors, pressure sensors, optical sensors and any combination thereof.

17. The system according to claim 16, wherein at least one of the following is being held true (a) said motion sensors detect motion of said joystick; wherein said motion detection of said joystick is used to deactivate said motion of said endoscope if said motion's speed is above a predetermined threshold; (b) said motion sensors detect motion upon the external surface of said joystick; wherein said motion upon the external surface of said joystick is used to operate said endoscope according to said motion upon said external surface; (c) said heat sensors are configured to sense temperature in the range of about 35 to about 42 degrees; (d) said heat sensors enable the activation of said MOS when said heat sensors sense said temperature is in the range of about 35 to about 42 degrees; (e) said heat sensors are configured to provide a thermal image, where said heat sensors are coupled to a processing unit configured to provide said endoscope user with said thermal image; (f) said electric sensors are configured to sense at least one of a group consisting of: power failure, connection to power, and electrical conductivity of a human body; (g) said sound sensors are configured to sense predetermined sound patterns; wherein said sound sensors are used to operate said endoscope according to said predetermined sound patterns; (h) said optical sensors are configured to sense visual changes according to predetermined visual patterns; wherein said optical sensors are used to operate said endoscope according to said predetermined visual patterns; (i) said pressure sensors are configured to sense pressure applied to said MOS; and any combination thereof.

18. The system according to claim 16 wherein said MOS is activated upon at least one condition selected from a group consisting of: analysis of said thermal image by said processing unit and detection of human hand, said electric sensors sense said human body conductivity, said sound sensors sense said predetermined sound patterns, and according to said predetermined visual patterns detected by said optical sensors.

* * * * *